United States Patent
Salbato et al.

(10) Patent No.: US 11,846,642 B2
(45) Date of Patent: *Dec. 19, 2023

(54) INDIRECT HOMOGENEOUS MOBILITY SHIFT ASSAYS FOR THE DETECTION OF BIOLOGICS IN PATIENT SAMPLES

(71) Applicant: Prometheus Laboratories Inc., San Diego, CA (US)

(72) Inventors: Jared Salbato, San Diego, CA (US); Stefan Westin, San Diego, CA (US); Nicholas Chi-Kwan Ling, San Diego, CA (US); Anjali Jain, San Diego, CA (US); Sharat Singh, San Diego, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 1157 days.

This patent is subject to a terminal disclaimer.

(21) Appl. No.: 16/536,777

(22) Filed: Aug. 9, 2019

(65) Prior Publication Data

US 2020/0088749 A1    Mar. 19, 2020

Related U.S. Application Data

(63) Continuation of application No. 15/603,137, filed on May 23, 2017, now Pat. No. 10,422,807, which is a continuation of application No. PCT/IB2015/059381, filed on Dec. 4, 2015.

(60) Provisional application No. 62/158,791, filed on May 8, 2015, provisional application No. 62/113,317, filed on Feb. 6, 2015, provisional application No. 62/088,465, filed on Dec. 5, 2014.

(51) Int. Cl.
| | | |
|---|---|---|
| *C07K 14/12* | (2006.01) | |
| *C07K 14/705* | (2006.01) | |
| *G01N 33/537* | (2006.01) | |
| *G01N 33/58* | (2006.01) | |
| *G01N 33/68* | (2006.01) | |
| *G01N 33/94* | (2006.01) | |
| *C07K 14/54* | (2006.01) | |
| *G01N 33/564* | (2006.01) | |

(52) U.S. Cl.
CPC .......... *G01N 33/94* (2013.01); *C07K 14/5434* (2013.01); *C07K 14/70546* (2013.01); *G01N 33/537* (2013.01); *G01N 33/564* (2013.01); *G01N 33/58* (2013.01); *G01N 33/6854* (2013.01); *C07K 2319/20* (2013.01); *C07K 2319/50* (2013.01); *G01N 2333/54* (2013.01); *G01N 2333/5434* (2013.01); *G01N 2333/70546* (2013.01); *G01N 2800/065* (2013.01); *G01N 2800/52* (2013.01)

(58) Field of Classification Search
CPC .......... C07K 14/5434; C07K 14/70546; G01N 2333/5434; G01N 2333/70546; G01N 2800/065; G01N 2800/52; G01N 33/582; G01N 33/6869
See application file for complete search history.

(56) References Cited

U.S. PATENT DOCUMENTS

| | | |
|---|---|---|
| 4,459,359 A | 7/1984 | Neurath |
| 4,857,456 A | 8/1989 | Urist |
| 4,965,069 A | 10/1990 | Quash et al. |
| 5,094,740 A | 3/1992 | Brandley et al. |
| 5,223,395 A | 6/1993 | Gero |
| 5,231,024 A | 7/1993 | Moeller et al. |
| 5,233,395 A | 8/1993 | Kohyama |
| 5,582,998 A | 12/1996 | Adolf |
| 5,698,419 A | 12/1997 | Wolpe et al. |
| 5,795,967 A | 8/1998 | Aggarwal et al. |
| 5,837,242 A | 11/1998 | Holliger et al. |
| 6,284,471 B1 | 9/2001 | Le et al. |
| 6,309,888 B1 | 10/2001 | Holvoet et al. |
| 6,444,461 B1 | 9/2002 | Knapp et al. |
| 6,903,183 B1 | 6/2005 | Stocco et al. |

(Continued)

FOREIGN PATENT DOCUMENTS

| | | |
|---|---|---|
| CN | 102695955 A | 9/2012 |
| CN | 103782172 A | 5/2014 |

(Continued)

OTHER PUBLICATIONS

Neri et al. "Enhancement of the antitumor activity of interluekin-12 by targeted delivery to neovasculature" Nature biotechnology, 20, 2002. (Year: 2002).*

(Continued)

*Primary Examiner* — Daniel E Kolker
*Assistant Examiner* — James L Rogers
(74) *Attorney, Agent, or Firm* — Greenberg Traurig LLP

(57) ABSTRACT

The present invention provides a sensitive and specific indirect homogeneous mobility shift assay using size exclusion chromatography to measure biologics such as vedolizumab and ustekinumab in a patient sample. The assays of the present invention are particularly advantageous for detecting the presence or level of biologics that target complex or large antigens including cell surface proteins, transmembrane proteins, heavily glycosylated proteins, and multimeric proteins, as well as antigens that cannot be purified, impure antigens, and partially or substantially purified antigens. The present invention also provides isolated soluble $\alpha 4\beta 7$ integrin heterodimers and isolated soluble IL-12p40 monomers that are suitable for use in the indirect assays described herein.

19 Claims, 20 Drawing Sheets

Specification includes a Sequence Listing.

(56) References Cited

U.S. PATENT DOCUMENTS

| | | | |
|---|---|---|---|
| 6,906,183 B2 | 6/2005 | Romisch et al. | |
| 7,189,515 B2 | 3/2007 | Buechler et al. | |
| 7,276,477 B2 | 10/2007 | Osslund et al. | |
| 7,524,502 B2 | 4/2009 | Hellendoorn et al. | |
| 7,542,502 B2 | 6/2009 | Steiger et al. | |
| 7,601,335 B2 | 10/2009 | McCutcheon et al. | |
| 7,611,702 B2 | 11/2009 | Fischkoff et al. | |
| 7,662,569 B2 | 2/2010 | Targan et al. | |
| 8,574,855 B2 * | 11/2013 | Singh | A61P 35/00 435/7.1 |
| 8,865,417 B2 * | 10/2014 | Singh | A61P 27/02 435/7.1 |
| 9,465,027 B2 * | 10/2016 | Hauenstein | B01D 15/34 |
| 9,506,920 B2 | 11/2016 | Singh et al. | |
| 9,784,748 B2 | 10/2017 | Wang et al. | |
| 10,386,366 B2 * | 8/2019 | Singh | G01N 33/564 |
| 10,422,807 B2 * | 9/2019 | Salbato | G01N 33/6854 |
| 10,794,906 B2 * | 10/2020 | Hauenstein | B01D 15/34 |
| 2002/0182651 A1 | 12/2002 | Patricelli | |
| 2003/0040027 A1 | 2/2003 | Ritter et al. | |
| 2003/0077246 A1 | 4/2003 | Welcher et al. | |
| 2003/0109691 A1 | 6/2003 | Arnaout et al. | |
| 2004/0022792 A1 | 2/2004 | Klinke et al. | |
| 2004/0157782 A1 | 8/2004 | Doronina et al. | |
| 2005/0054005 A1 | 3/2005 | Ellis et al. | |
| 2005/0129681 A1 * | 6/2005 | Varner | G01N 33/6893 424/143.1 |
| 2005/0181483 A1 | 8/2005 | Sawyer et al. | |
| 2006/0003384 A1 | 1/2006 | Wagner et al. | |
| 2006/0078944 A1 | 4/2006 | Kuai et al. | |
| 2006/0110407 A1 | 5/2006 | Stopera et al. | |
| 2006/0240480 A1 | 10/2006 | Curdt et al. | |
| 2006/0253263 A1 | 11/2006 | Meshkin | |
| 2007/0077249 A1 | 4/2007 | Silence et al. | |
| 2008/0280311 A1 | 11/2008 | Strohner | |
| 2008/0286774 A1 | 11/2008 | Turteltaub et al. | |
| 2009/0035216 A1 | 2/2009 | Svenson et al. | |
| 2009/0162374 A1 | 6/2009 | Geraghty et al. | |
| 2009/0234202 A1 | 9/2009 | Goix et al. | |
| 2009/0275496 A1 | 11/2009 | Baldwin et al. | |
| 2010/0130367 A1 | 5/2010 | Murthy et al. | |
| 2010/0167418 A1 * | 7/2010 | Springer | G01N 33/566 436/501 |
| 2010/0330156 A1 | 12/2010 | Liu et al. | |
| 2012/0329172 A1 | 12/2012 | Singh et al. | |
| 2013/0072433 A1 * | 3/2013 | Du | A61K 47/6909 514/13.8 |
| 2013/0266963 A1 | 10/2013 | Hauenstein et al. | |
| 2013/0295685 A1 | 11/2013 | Singh et al. | |
| 2013/0344621 A1 | 12/2013 | Wang et al. | |
| 2014/0045276 A1 | 2/2014 | Singh et al. | |
| 2014/0051184 A1 | 2/2014 | Singh et al. | |
| 2014/0057367 A1 | 2/2014 | Singh et al. | |
| 2014/0135483 A1 | 5/2014 | Seito et al. | |
| 2014/0186973 A1 | 7/2014 | Hauenstein et al. | |
| 2014/0371133 A1 * | 12/2014 | Francois | A61P 11/06 514/21.1 |
| 2015/0010563 A1 * | 1/2015 | Hamrah | A61P 37/00 424/139.1 |
| 2015/0024404 A1 | 1/2015 | Singh et al. | |
| 2016/0295685 A1 | 10/2016 | Ryu et al. | |
| 2017/0176433 A1 | 6/2017 | Hauenstein et al. | |
| 2017/0184588 A1 | 6/2017 | Singh et al. | |
| 2017/0328923 A1 | 11/2017 | Salbato et al. | |
| 2019/0024174 A1 * | 1/2019 | Begovich | C12Q 1/6883 |
| 2019/0331694 A1 | 10/2019 | Arch et al. | |
| 2019/0343425 A1 | 11/2019 | Jones et al. | |

FOREIGN PATENT DOCUMENTS

| | | |
|---|---|---|
| EP | 0440044 A1 | 8/1991 |
| EP | 0492448 A1 | 7/1992 |
| EP | 0642021 A2 | 3/1995 |
| EP | 0882984 A1 | 12/1998 |
| EP | 1237926 A1 | 9/2002 |
| EP | 1637601 A2 | 3/2006 |
| EP | 1769244 A2 | 4/2007 |
| EP | 1902320 A2 | 3/2008 |
| EP | 1237926 B1 | 6/2009 |
| EP | 2676137 B1 | 12/2014 |
| JP | H05000096 | 1/1993 |
| JP | H0566222 A | 3/1993 |
| JP | H07110331 A | 4/1995 |
| JP | H07140144 A | 6/1995 |
| JP | H11500607 A | 1/1999 |
| JP | 2001249127 A | 9/2001 |
| JP | 2007147367 A | 6/2007 |
| JP | 2011254179 A | 12/2011 |
| JP | 2013508739 A | 3/2013 |
| JP | 2013545438 A | 12/2013 |
| JP | 2014515763 A | 7/2014 |
| JP | 2014525036 A | 9/2014 |
| WO | WO-9410308 A1 | 5/1994 |
| WO | WO-9620219 A2 | 7/1996 |
| WO | WO-02081518 A2 | 10/2002 |
| WO | WO-2005019271 A1 | 3/2005 |
| WO | WO-2005072340 A2 | 8/2005 |
| WO | WO-2006004958 A2 | 1/2006 |
| WO | WO-2007009469 A2 | 1/2007 |
| WO | WO-2009012140 A2 | 1/2009 |
| WO | WO-2009012140 A3 | 3/2009 |
| WO | WO-2009091240 A1 | 7/2009 |
| WO | WO-2011056590 A1 * | 5/2011 ............... A61P 1/04 |
| WO | WO-2012032181 A2 | 3/2012 |
| WO | WO-2012054532 A1 | 4/2012 |
| WO | WO-2012151247 A2 | 11/2012 |
| WO | WO-2012154253 A1 | 11/2012 |
| WO | WO-2013006810 A1 | 1/2013 |
| WO | WO-2014083520 A2 | 6/2014 |

OTHER PUBLICATIONS

Springer et al. "Structural specializations of alpha4beta7, an integrin that mediates rolling adhesion" J. Cell. Biol. 196(1), pp. 131-146, 2012 (Year: 2012).*

Aarden et al.: Immunogenicity of anti-tumor necrosis factor antibodies—toward improved methods of anti-antibody measurement. Current Opinion in Immunology 20(4):431-435 (2008).

Arcangelo & Peterson, Pharmacotherapeutics for Advanced Practice: A Practical Approach, Philadelphia, PA, 536:18 (2006).

Apostolovic et al.: Coiled coils: attractive protein folding motifs for the fabrication of self-assembled, responsive and bioactive materials. Chemical Society Reviews. 39(9):3541 (2010).

Arends et al.: The formation of autoantibodies and antibodies to TNF-a blocking agents in relation to clinical response in patients with ankylosing spondylitis. Clinical and Experimental Rheumatology 28(5):661-668 (2010).

Aybay et al.: Demonstration of specific antibodies against infliximab induced during treatment of a patient with ankylosing spondylitis. Rheumatology International, Clin. And Exper. Invest. 26(5):473-480 (2006).

Bendtzen et al.: Individualized monitoring of drug bioavailability and immunogenicity in rheumatoid arthritis patients treated with the tumor necrosis factor α inhibitor infliximab. Arthritis & Rheumatism 54(12): 3782-3789 (2006).

Benucci et al.: No correlations between the development of specific IgA and IgM antibodies against anti-TNF blocking agents, disease activity and adverse side reactions in patients with Rheumatoid arthritis. The Open Rheumatology Journal 7:75-80 (2013).

Bourdage et al.: An affinity capture elution (ACE) assay for detection of anti-drug antibody to monoclonal antibody therapeutics in the presence of high levels of drug. J. Immunol. Methods 327(1-2):10-17 (2007).

Brekke et al.: Therapeutic antibodies for human diseases at the dawn of the twenty-first century. Nature Reviews Drug Discovery 2(1):52-62 (2003).

Cheifetz et al.: Monoclonal antibodies: immunogenicity, and associated infusion reactions. Mount Sinai J. Medicine 72(4):250-256 (2005).

(56) References Cited

OTHER PUBLICATIONS

Chernesky & Mahony, Immunoassays: principles and assay design, in Virology Methods Manuals, Mahy & Kangro (Eds.), pp. 123-124, San Diego, CA: Academic Press Inc. (1996).
Cisbio Bioassays. HTRF human kappa and lambda MAb assay: A new solution for human IgG characterisation. URL: http://www.biolab.cn/plus/view-241835-1.html, Accessed on Feb. 20, 2014 (2009).
Clark et al.: Production of recombinant soluble human integrin α4β1. FEBS Letters 471:182-186 (2000).
Deventer et al.: Anti-tumour necrosis factor therapy in Crohn's disease: Where are we now? Gut 51(3):362-363 (2002).
Elliott et al.: Repeated therapy with monoclonal antibody to tumour necrosis factor alpha (cA2) in patients with rheumatoid arthritis. Lancet 334(8930):1125-1127 (1994).
English Machine Translation of CN 103782172 A; published May 7, 2014, 47 pages.
English Machine Translation of JP 07-140144; published Jun. 2, 1995, abstract only, 1 page.
English Machine Translation of JP 2013-508739; published May 7, 2013, 53 pages.
European Patent Application No. 19163825.3 European Search Report dated Jun. 7, 2019.
Finckh et al.: Influence of anti-infliximab antibodies and residual infliximab concentrations on the occurrence of acquired drug resistance to infliximab in rheumatoid patients. Joint Bone Spine 77:313-318 (2010).
Flood: Tumor necrosis factor inhibitors in the treatment of chronic inflammatory diseases: A review of immunogenicity and potential implications. Suppl. to Managed Care 18(4):1-5 (2009).
Gisbert et al.: Loss of response and requirement of infliximab dose intensification in Crohn's disease: a review. Journal of Gastroenterology 104:760-767 (2009).
Hagg et al.: Measurement and biological correlates of antibody bioactivity during antibody immunotherapies. J. Immunol. Meth. 219(1-2): 7-21 (1998).
Harlow, E. and Lane, D.: Antibodies: A Laboratory Manual. Cold Spring Harbor Laboratory Press, Cold Spring Harbor, NY, pp. 7-10, (1988).
Harris: Quantitative Chemical Analysis, Sixth Ed., New York, W.H. Freeman Co., p. 85-86 (2003).
Harris: Quantitative Chemical Analysis, Sixth Ed., New York, W.H. Freeman Co., p. 91 (2003).
Holmskov-Nielsen et al.: Immune complex formation analysed by high-performance size exclusion chromatography (HPLC-SEC) using either 125I-labelled antigen or enzyme-linked immunosorbent assay (ELISA) for detection. Immunology 51(4):809-814 (1984).
Hosono et al.: Human-mouse chimeric antibodies show low reactivity with human anti-murine antibodies HAMA. British J. Cancer 65(2):197-200 (1992).
International Application No. PCT/IB2015/058048 International Search Report and Written Opinion dated Apr. 28, 2016.
Invitrogen: Looking on the bright side with Alexa Fluor® secondary antibodies.URL http://www.jimmunol.org/content/181/3/local/advertising.pdf, retrieved on Oct. 11, 2013 (2008).
Kawate et al.: Fluorescence-detection size-exclusion chromatography for precrystallization screening of integral membrane proteins. Structure 14:673-681 (2006).
Kim et al.: Comparative analyses of complex formation and binding sites between Human Tumor Necrosis Factor-alpha and its three antagonists elucidate their different neutralizing mechanisms. J. Mol. Biol. 374:1374-1388 (2007).
Koren et al.: Recommendations on risk-based strategies for detection and characterization of antibodies against biotechnology products. Journal of Immunological Methods 333:1-9 (2008).
Lofgren et al.: Detection of neutralizing anti-therapeutic protein antibodies in serum or plasma samples containing high levels of the therapeutic protein. J. Immunol. Meth. 308(1-2):101-108 (2006).

Maier et al.: Fluorescent HPLC assay for 20-HETE and other P-450 metabolites of arachidonic acid. A. J. Physiol. Heart Circ. Physiol. 279:H865-H871 (2000).
Molecular Probes, Inc.: BioParticles® Fluorescent Particles and Opsonizing Reagents; Product Information, Mar. 9, 2001, pp. 1-3, retrieved online from http://tools.lifetechnologies.com/content/sfs/manuals/mp02701.pdf on Aug. 12, 2014 (2001).
Murtazina et al.: Immunochemical detection of sulfamethazine in river water and medicines. Chemotherapeutic Magazine 39(8):93-97 (2005).
O'Keeffe: Residue Analysis in Food Principles and Applications, Amsterdam, Hardwood Academic Publishers, p. 20 (2000).
Palframan et al.: Use of biofluorescence imaging to compare the distribution of certolizumab pegol, adalimumab, and infliximab in the inflamed paws of mice with collagen-induced arthritis. J. Immunol. Methods. 348(1-2):36-41 (2009).
Panchuk-Voloshina et al.: Alexa dyes, a series of new fluorescent dyes that yield exceptionally bright, photostable conjugates. J Histochem Cytochem. 47(9):1179-1188 (1999).
Patton et al.: An acid dissociation bridging ELISA for detection of antibodies directed against therapeutic proteins in the presence of antigen. J. Immunol. Meth. 304(1-2):189-195 (2005).
Reynolds et al.: Anti-murine antibody response to mouse monoclonal antibodies: Clinical findings and implications. Intl. J. Radiation Applications and Instrumentation, Part B: Nuclear Medicine and Biology 16(2):121-125 (1989).
Rojas et al.: Formation, distribution, and elimination of infliximab and anti-infliximab immune complexes in cynomolgus monkeys. JPET, 313(2):578-585 (2005).
Salbato et al.: Tu1301 validation of a homogenous mobility shift assay (HMSA) for the measurement of vedolizumab (VLM) and anti-VLM antibodies in inflammatory bowel disease (IBD) patient serum. Gastroenterology 148(4):S-852 (2015).
Santora et al.: Characterization of noncovalent complexes of recombinant human monoclonal antibody and antigen using cation exchange, size exclusion chromatography, and BIAcore. Analytical Biochemistry 299:119-129 (2001).
Scallon et al.: Binding and functional comparisons of two types of tumor necrosis factor antagonists. J. Pharmacol. Exper. Ther. 301(2):418-426 (2002).
Sickert et al.: Improvement of drug tolerance in immunogenicity testing by acid treatment on Biacore. J. Immunol. Meth., 334(1-2):29-36 (2008).
Smith et al.: Detection of antibodies against therapeutic proteins in the presence of residual therapeutic protein using a solid-phase extraction with acid dissociation (SPEAD) sample treatment prior to ELISA. Regulatory Toxicology and Pharmacology 49(3): 230-237 (2007).
Steenholdt et al.: Measurement of infliximab and anti-infliximab antibody levels can help distinguish maintenance versus loss of response. Gastroenterology & Hepatology 8(2):131-134 (2012).
Svenson et al.: Monitoring patients treated with anti-TNFa biopharmaceuticals: assessing serum infliximab and anti-infliximab antibodies. Rheumatology 46:1828-1834 (2007).
Tayyab et al.: Size exclusion chromatography and size exclusion HPLC of proteins. Biochem Ed, Pergamon. 19(3):149-152 (1991).
Tiittanen et al.: Anti-insulin activity in IgG-fractions from children with newly-diagnosed type 1 diabetes and negative for insulin autoantibodies. Autoimmunity 37(1): 45-49 (2004).
U.S. Department of Health and Human Services et al.: Guidance for industry: assay development for immunogenicity testing of therapeutic proteins. Draft Guidance, retrieved from http://www.fda.gov/Drugs/GuidanceComplianceRegulatoryInformation/Guidances/UCM 192750 (2009).
U.S. Appl. No. 15/254,934 Final Office Action dated Oct. 29, 2019.
Van Der Laken et al.: Imaging and serum analysis of immune complex formation of radiolabeled infliximab and anti-infliximab in responders and non-responders to therapy for rheumatoid arthritis. Ann. Rheum. Dis. 66(2):253-256 (2007).
Van Schouwenburg et al.: A novel method for the detection of antibodies to adalimumab in the presence of drug reveals "hidden" immunogenicity in rheumatoid arthritis patients. J. Immunol. Meth. 362(1-2):82-88 (2010).

(56) References Cited

OTHER PUBLICATIONS

Wang et al.: Analysis of anti-drug antibodies (ADA) to adalimumab in patient serum using a novel homogeneous mobility shift assay. Am. J. Gastro. 105(Suppl. 1): S444-S445 (2010).

Wang et al.: Development and validation of a homogeneous mobility shift assay for the measurement of infliximab and antibodies-to-infliximab levels in patient serum. Journal of Immunological Methods 382:177-188 (2012).

Wan. et al.: Monitoring of adalimumab and antibodies-to-adalimumab levels in patient serum by the homogeneous mobility shift assay. Journal of Pharmaceutical and Biomedical Analysis 78-79:39-44 (2013).

Yu et al.: Structural specializations of [alpha] 4 [beta] 7, an integrin that mediates rolling adhesion. The Journal of Cell Biology. 196(1):131-146 (2012).

\* cited by examiner

Vedolizumab Drug Assay – Validation Specs

| Assay parameters (n=30) | Calculated (µg/ml) |
|---|---:|
| Limit of Blank (LOB) | 0.054 |
| Limit of Detection (LOD) | 0.35 |
| Lower limit of quantitation (LLOQ) | 0.625 |
| Upper limit of quantitation (ULOQ) | 14 |

FIG. 5

VLM: Validation: Intra-assay Precision & Accuracy

|  |  | Average(n=10) | SD | %CV | % Error |
|---|---|---|---|---|---|
| High Control | 16 µg/mL | 15.66 | 1.05 | 6.73 | -2.08 |
| Med Control | 4 µg/mL | 4.11 | 0.17 | 4.30 | 2.91 |
| Low Control | 1 µg/mL | 1.24 | 0.033 | 2.73 | 24.08 |

*FIG. 6*

| ATV U/mL | ST1 | ST2 | ST3 | ST4 | ST5 | ST6 | ST7 | ST8 |
|---|---|---|---|---|---|---|---|---|
| Experiment | 200 | 100 | 50 | 25 | 13 | 6 | 3.13 | 1.56 |
| 1 | 192 | 104 | 49 | 25 | 13.1 | 6.6 | 3.04 | 1.05 |
| 2 | 191 | 103 | 49 | 25 | 12.6 | 6.3 | 3.16 | 1.53 |
| 3 | 193 | 102 | 50 | 25 | 12.5 | 6.3 | 3.16 | 1.54 |
| 4 | 192 | 103 | 49 | 25 | 12.4 | 6.3 | 3.15 | 1.55 |
| AVERAGE | 192.2 | 103.1 | 49.3 | 24.8 | 12.7 | 6.4 | 3.1 | 1.4 |
| STDEV | 0.7 | 0.8 | 0.6 | 0.2 | 0.3 | 0.1 | 0.1 | 0.2 |
| %CV | 0.4 | 0.8 | 1.3 | 0.8 | 2.5 | 2.2 | 1.8 | 17.2 |
| %RECOVERY | 96.1 | 103.1 | 98.7 | 99.3 | 101.4 | 102.2 | 100.0 | 90.7 |

ATV : Validation: LOB & LOD, LLOQ & ULOQ

Limits of Detection

| | Mean (n=25) | SD | 1.65SD | Mean +1.65SD | (LOB) Interpolated Value |
|---|---|---|---|---|---|
| LOB | 0.00828 | 0.00013 | 0.00022 | 0.00850 | Too low to interpolate |
| LOD | LOB + 1.65SD (low conc sample) : could not be determined as LOB has no value | | | | |

LOD = LLOQ = 3.13

Limits of Quantitation

| | | Average (n=36) | SD | % CV | % Error |
|---|---|---|---|---|---|
| LLOQ | 3.13 (U/mL) | 3.68 | 0.08 | 2.14 | -17.57 |
| ULOQ | 150 (U/mL) | 157.93 | 2.67 | 1.69 | -5.29 |

*FIG. 9*

ATV : Validation: Inter-assay Precision

Inter-assay Precision n=4

|  |  | Average(n=4) | SD | %CV | % Error |
|---|---|---|---|---|---|
| High Control | 50 (U/mL) | 50.8 | 3.9 | 7.7 | 1.5 |
| Med Control | 25 (U/mL) | 25.2 | 1.3 | 5.3 | 0.9 |
| Low Control | 12.5 (U/mL) | 13.1 | 0.6 | 4.7 | 5.0 |

*FIG. 10*

Ustekinumab Drug Assay – Validation Specs

| Assay parameters (n=30) | Calculated (µg/ml) |
|---|---:|
| Limit of Blank (LOB) | 0.233 |
| Limit of Detection (LOD) | 0.147 |
| Lower limit of quantitation (LLOQ) | 0.625 |
| Upper limit of quantitation (ULOQ) | 8 |

FIG. 11

| Controls (n=1) | SD | %CV | %Error |
|---|---|---|---|
| 44.71 | NA | NA | -10.58 |
| 24.06 | NA | NA | -3.76 |
| 13.87 | NA | NA | -10.96 |

SEQUENCE LISTING

<160> NUMBER OF SEQ ID NOS: 13

<210> SEQ ID NO 1
<211> LENGTH: 620
<212> TYPE: PRT
<213> ORGANISM: Homo sapiens
<220> FEATURE:
<221> NAME/KEY: MISC_FEATURE
<222> LOCATION: (1)..(620)
<223> OTHER INFORMATION: Human alpha 4 integrin fragment

<400> SEQUENCE: 1

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
    275                 280                 285

Lys Glu Leu Asn Ile Leu His Glu Met Lys Gly Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
                340                 345                 350

Ala Met Glu Thr Asn Leu Val Gly Ser Asp Lys Tyr Ala Ala Arg Phe
                355                 360                 365

Gly Glu Ser Ile Val Asn Leu Gly Asp Ile Asp Asn Asp Gly Phe Glu
                370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
                420                 425                 430

Ser Ile Ser Gly Gln Ile Asp Ala Asp Asn Asn Gly Tyr Val Asp Val
                435                 440                 445

Ala Val Gly Ala Phe Arg Ser Asp Ser Ala Val Leu Leu Arg Thr Arg
                450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
                500                 505                 510

Ile Val Leu Phe Tyr Asn Met Ser Leu Asp Val Asn Arg Lys Ala Glu
                515                 520                 525

Ser Pro Pro Arg Phe Tyr Phe Ser Ser Asn Gly Thr Ser Asp Val Ile
                530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
                580                 585                 590

Thr Glu Glu Phe Pro Pro Leu Gln Pro Ile Leu Gln Gln Lys Lys Glu
                595                 600                 605

Lys Asp Ile Met Lys Lys Thr Ile Asn Phe Ala Arg
610                 615                 620

<210> SEQ ID NO 2
<211> LENGTH: 527
<212> TYPE: PRT
<213> ORGANISM: Homo sapiens
<220> FEATURE:
<221> NAME/KEY: MISC_FEATURE
<222> LOCATION: (1)..(527)
<223> OTHER INFORMATION: Human beta 7 integrin fragment

<400> SEQUENCE: 2

```
Met Val Ala Leu Pro Met Val Leu Val Leu Leu Val Leu Ser Arg
 1               5                  10                  15

Gly Glu Ser Glu Leu Asp Ala Lys Ile Pro Ser Thr Gly Asp Ala Thr
             20                  25                  30

Glu Trp Arg Asn Pro His Leu Ser Met Leu Gly Ser Cys Gln Pro Ala
         35                  40                  45

Pro Ser Cys Gln Lys Cys Ile Leu Ser His Pro Ser Cys Ala Trp Cys
 50                  55                  60

Lys Gln Leu Asn Phe Thr Ala Ser Gly Glu Ala Glu Ala Arg Arg Cys
 65                  70                  75                  80

Ala Arg Arg Glu Glu Leu Leu Ala Arg Gly Cys Pro Leu Glu Glu Leu
             85                  90                  95

Glu Glu Pro Arg Gly Gln Gln Glu Val Leu Gln Asp Gln Pro Leu Ser
         100                 105                 110

Gln Gly Ala Arg Gly Glu Gly Ala Thr Gln Leu Ala Pro Gln Arg Val
             115                 120                 125

Arg Val Thr Leu Arg Pro Gly Glu Pro Gln Gln Leu Gln Val Arg Phe
 130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                 165                 170                 175

Ala Leu Leu Val Arg Leu Gln Glu Val Thr His Ser Val Arg Ile Gly
             180                 185                 190

Phe Gly Ser Phe Val Asp Lys Thr Val Leu Pro Phe Val Ser Thr Val
 195                 200                 205

Pro Ser Lys Leu Arg His Pro Cys Pro Thr Arg Leu Glu Arg Cys Gln
 210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
             245                 250                 255

Ser Pro Glu Gly Gly Phe Asp Ala Ile Leu Gln Ala Ala Leu Cys Gln
         260                 265                 270

Glu Gln Ile Gly Trp Arg Asn Val Ser Arg Leu Leu Val Phe Thr Ser
             275                 280                 285

Asp Asp Thr Phe His Thr Ala Gly Asp Gly Lys Leu Gly Gly Ile Phe
 290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                 325                 330                 335

Leu Ser Ala Ala Asn Ile Gln Pro Ile Phe Ala Val Thr Ser Ala Ala
             340                 345                 350

Leu Pro Val Tyr Gln Glu Leu Ser Lys Leu Ile Pro Lys Ser Ala Val
         355                 360                 365

Gly Glu Leu Ser Glu Asp Ser Ser Asn Val Val Gln Leu Ile Met Asp
         370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                 405                 410                 415

Lys Arg Glu Gly Lys Ala Glu Asp Arg Gly Gln Cys Asn His Val Arg
```

-continued

```
                420             425             430
Ile Asn Gln Thr Val Thr Phe Trp Val Ser Leu Gln Ala Thr His Cys
            435                 440                 445

Leu Pro Glu Pro His Leu Leu Arg Leu Arg Ala Leu Gly Phe Ser Glu
450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
            485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys
            515                 520                 525

<210> SEQ ID NO 3
<211> LENGTH: 654
<212> TYPE: PRT
<213> ORGANISM: Homo sapiens
<220> FEATURE:
<221> NAME/KEY: MISC_FEATURE
<222> LOCATION: (1)..(654)
<223> OTHER INFORMATION: Human alpha 4 integrin fragment with acidic
      peptide

<400> SEQUENCE: 3

Met Ala Trp Glu Ala Arg Arg Glu Pro Gly Pro Arg Arg Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
        50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
            115                 120                 125

Val Thr Leu Ser Arg Gln Pro Gly Glu Asn Gly Ser Ile Val Thr Cys
130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
            195                 200                 205

Asp Leu Ile Val Met Gly Ala Pro Gly Ser Ser Tyr Trp Thr Gly Ser
        210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
```

Ala Gly His Phe Arg Ser Gln His Thr Thr Glu Val Val Gly Gly Ala
            245                 250                 255

Pro Gln His Glu Gln Ile Gly Lys Ala Tyr Ile Phe Ser Ile Asp Glu
260                 265                 270

Lys Glu Leu Asn Ile Leu His Glu Met Lys Gly Lys Lys Leu Gly Ser
    275                 280                 285

Tyr Phe Gly Ala Ser Val Cys Ala Val Asp Leu Asn Ala Asp Gly Phe
290                 295                 300

Ser Asp Leu Leu Val Gly Ala Pro Met Gln Ser Thr Ile Arg Glu Glu
305                 310                 315                 320

Gly Arg Val Phe Val Tyr Ile Asn Ser Gly Ser Gly Ala Val Met Asn
    325                 330                 335

Ala Met Glu Thr Asn Leu Val Gly Ser Asp Lys Tyr Ala Ala Arg Phe
        340                 345                 350

Gly Glu Ser Ile Val Asn Leu Gly Asp Ile Asp Asn Asp Gly Phe Glu
            355                 360                 365

Asp Val Ala Ile Gly Ala Pro Gln Glu Asp Asp Leu Gln Gly Ala Ile
370                 375                 380

Tyr Ile Tyr Asn Gly Arg Ala Asp Gly Ile Ser Ser Thr Phe Ser Gln
385                 390                 395                 400

Arg Ile Glu Gly Leu Gln Ile Ser Lys Ser Leu Ser Met Phe Gly Gln
    405                 410                 415

Ser Ile Ser Gly Gln Ile Asp Ala Asp Asn Asn Gly Tyr Val Asp Val
        420                 425                 430

Ala Val Gly Ala Phe Arg Ser Asp Ser Ala Val Leu Leu Arg Thr Arg
            435                 440                 445

Pro Val Val Ile Val Asp Ala Ser Leu Ser His Pro Glu Ser Val Asn
450                 455                 460

Arg Thr Lys Phe Asp Cys Val Glu Asn Gly Trp Pro Ser Val Cys Ile
465                 470                 475                 480

Asp Leu Thr Leu Cys Phe Ser Tyr Lys Gly Lys Glu Val Pro Gly Tyr
    485                 490                 495

Ile Val Leu Phe Tyr Asn Met Ser Leu Asp Val Asn Arg Lys Ala Glu
        500                 505                 510

Ser Pro Pro Arg Phe Tyr Phe Ser Ser Asn Gly Thr Ser Asp Val Ile
            515                 520                 525

Thr Gly Ser Ile Gln Val Ser Ser Arg Glu Ala Asn Cys Arg Thr His
530                 535                 540

Gln Ala Phe Met Arg Lys Asp Val Arg Asp Ile Leu Thr Pro Ile Gln
545                 550                 555                 560

Ile Glu Ala Ala Tyr His Leu Gly Pro His Val Ile Ser Lys Arg Ser
    565                 570                 575

Thr Glu Glu Phe Pro Pro Leu Gln Pro Ile Leu Gln Gln Lys Lys Glu
        580                 585                 590

Lys Asp Ile Met Lys Lys Thr Ile Asn Phe Ala Arg Thr Gly Gly Leu
            595                 600                 605

Ala Gln Cys Glu Lys Glu Leu Gln Ala Leu Glu Lys Glu Asn Ala Gln
610                 615                 620

Leu Glu Trp Glu Leu Gln Ala Leu Glu Lys Glu Leu Ala Gln
625                 630                 635                 640

<210> SEQ ID NO 4

```
<211> LENGTH: 578
<212> TYPE: PRT
<213> ORGANISM: Homo sapiens
<220> FEATURE:
<221> NAME/KEY: MISC_FEATURE
<222> LOCATION: (1)..(578)
<223> OTHER INFORMATION: Human beta 7 integrin fragment with the BASE-p1
      sequence of peptide Velcro containing a Cys at the "d" positions
      of the heptad repeat peptide with TEV cleavage site and His6 tag

<400> SEQUENCE: 4
```

Met Val Ala Leu Pro Met Val Leu Val Leu Leu Val Leu Ser Arg
1               5                   10                  15

Gly Glu Ser Glu Leu Asp Ala Lys Ile Pro Ser Thr Gly Asp Ala Thr
            20                  25                  30

Glu Trp Arg Asn Pro His Leu Ser Met Leu Gly Ser Cys Gln Pro Ala
        35                  40                  45

Pro Ser Cys Gln Lys Cys Ile Leu Ser His Pro Ser Cys Ala Trp Cys
    50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
                85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
    210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
        275                 280                 285

Asp Asp Thr Phe His Thr Ala Gly Asp Gly Lys Leu Gly Gly Ile Phe
    290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                325                 330                 335

Leu Ser Ala Ala Asn Ile Gln Pro Ile Phe Ala Val Thr Ser Ala Ala
            340                 345                 350

Leu Pro Val Tyr Gln Glu Leu Ser Lys Leu Ile Pro Lys Ser Ala Val

```
                355                 360                 365
Gly Glu Leu Ser Glu Asp Ser Ser Asn Val Val Gln Leu Ile Met Asp
        370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Gly
        515                 520                 525

Gly Leu Glu Asn Gly Tyr Phe Gln Gly Gly Lys Asn Ala Gln Cys Lys
    530                 535                 540

Lys Lys Leu Gln Ala Leu Lys Lys Asn Ala Gln Leu Lys Trp Lys
545                 550                 555                 560

Leu Gln Ala Leu Lys Lys Leu Ala Gln Gly Gly His His His
                565                 570                 575

His His

<210> SEQ ID NO 5
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IL-12p40 wild-type

<400> SEQUENCE: 5

Met Cys His Gln Gln Leu Val Ile Ser Trp Phe Ser Leu Val Phe Leu
1               5                  10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
    115                 120                 125
```

```
Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Ala Pro Ala Ala Glu Glu Ser Leu Pro Ile
                195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Ala Val Gln Val Gln Gly Lys Ser Lys Arg Glu Lys Lys Asp Arg
                275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys
                325

<210> SEQ ID NO 6
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IL-12p40 variant (C199A, C274A)

<400> SEQUENCE: 6

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
                35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
                115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160
```

```
145                 150                 155                 160
Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Ala Pro Ala Ala Glu Ser Leu Pro Ile
                195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Ala Val Gln Val Gln Gly Lys Ser Lys Arg Glu Lys Lys Asp Arg
                275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys
                325

<210> SEQ ID NO 7
<211> LENGTH: 333
<212> TYPE: PRT
<213> ORGANISM: Homo sapiens
<220> FEATURE:
<221> NAME/KEY: MISC_FEATURE
<222> LOCATION: (1)..(333)
<223> OTHER INFORMATION: Human IL-12p40 variant (C199A, C274A) with
      hexahistidine tag

<400> SEQUENCE: 7

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65              70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
```

```
                      165                 170                 175

Ala Glu Arg Val Arg Gly Asp Asn Lys Glu Tyr Glu Tyr Ser Val Glu
            180                 185                 190

Cys Gln Glu Asp Ser Ala Ala Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Ala Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys His His His His His
            325                 330

<210> SEQ ID NO 8
<211> LENGTH: 30
<212> TYPE: PRT
<213> ORGANISM: Artificial Sequence
<220> FEATURE:
<223> OTHER INFORMATION: ACID peptide with cysteine residue (3)

<400> SEQUENCE: 8

Ala Gln Cys Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln
            20                  25                  30

<210> SEQ ID NO 9
<211> LENGTH: 51
<212> TYPE: PRT
<213> ORGANISM: Artificial Sequence
<220> FEATURE:
<223> OTHER INFORMATION: BASE peptide with cysteine residue (16), TEV
      cleavage site (3-9), and hexahistidine tag (46-51)

<400> SEQUENCE: 9

Gly Gly Leu Glu Asn Gly Tyr Phe Gln Gly Gly Lys Asn Ala Gln Cys
1               5                   10                  15

Lys Lys Lys Leu Gln Ala Leu Lys Lys Asn Ala Gln Leu Lys Trp
            20                  25                  30

Lys Leu Gln Ala Leu Lys Lys Lys Leu Ala Gln Gly Gly His His His
        35                  40                  45

His His His
    50

<210> SEQ ID NO 10
<211> LENGTH: 7
<212> TYPE: PRT
<213> ORGANISM: Artificial Sequence
<220> FEATURE:
<223> OTHER INFORMATION: TEV cleavage site
<220> FEATURE:
```

```
-continued

<221> NAME/KEY: VARIANT
<222> LOCATION: (2)..(3)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid

<400> SEQUENCE: 10

Glu Xaa Xaa Tyr Xaa Gln Ser
1               5

<210> SEQ ID NO 11
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IL-12p40 variant(C199S, C274S)

<400> SEQUENCE: 11

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Ser Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Ser Val Gln Val Gln Gly Lys Ser Lys Arg Glu Lys Lys Asp Arg
        275                 280                 285
```

```
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys
                325

<210> SEQ ID NO 12
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IL-12p40 variant(C199A, C274S)

<400> SEQUENCE: 12

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
    115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Ala Pro Ala Ala Glu Glu Ser Leu Pro Ile
    195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Ser Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
```

```
                305                 310                 315                 320
Glu Trp Ala Ser Val Pro Cys
                325

<210> SEQ ID NO 13
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IL-12p40 variant(C199S, C274A)

<400> SEQUENCE: 13

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Ser Pro Ala Ala Glu Glu Ser Leu Pro Ile
    195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Ala Val Gln Val Gln Gly Lys Ser Lys Arg Glu Lys Lys Asp Arg
    275                 280                 285
```

```
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys
                325
```

INDIRECT HOMOGENEOUS MOBILITY SHIFT ASSAYS FOR THE DETECTION OF BIOLOGICS IN PATIENT SAMPLES

CROSS-REFERENCE TO RELATED APPLICATIONS

This application is a continuation of U.S. application Ser. No. 15/603,137 filed May 23, 2017 which is a continuation of PCT/IB2015/059381, filed Dec. 4, 2015, which claims priority to U.S. Provisional Application No. 62/088,465, filed Dec. 5, 2014, U.S. Provisional Application No. 62/113,317, filed Feb. 6, 2015, and U.S. Provisional Application No. 62/158,791, filed May 8, 2015, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Aug. 8, 2019 is named 56884867302 SL.txt and is 40,507 bytes in size.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases and how these diseases will progress. The cost of IBD and IBS is compounded by lost productivity, with people suffering from these disorders missing at least 8 more days of work annually than the national average.

Despite the successes of anti-TNFα therapies in the treatment of IBD, a subpopulation of patients are refractory to treatment, highlighting an unmet medical need for new therapies. Vedolizumab is a gut-specific, α4β7 integrin-neutralizing monoclonal antibody, which does not affect peripheral blood cell counts and appears to lack systemic effects. Vedolizumab is a new anti-inflammatory treatment option for the management of therapy-refractory patients. In addition, ustekinumab is a IL12p40 monoclonal antibody, which is another novel IBD therapeutic. However, the availability of diagnostic tests to accurately measure the levels of biologics such as vedolizumab and ustekinumab is necessary for the effective use of these novel therapeutics in IBD patients.

As such, there is a need in the art for assays to detect the presence or level of biologics such as vedolizumab and ustekinumab in a patient sample to monitor drug therapy and to guide treatment decisions. Such assays are particularly useful for the therapeutic management of diseases such as ulcerative colitis and Crohn's disease using an individualized approach to monitor drug efficacy and optimize therapy accordingly, and can include assessing disease course and clinical parameters such as pharmacodynamics, disease activity indices, disease burden, and inflammatory biomarkers. The present invention satisfies this need and provides related advantages as well.

BRIEF SUMMARY OF THE INVENTION

The present invention provides novel indirect homogeneous mobility shift assays for detecting and measuring the presence or level of a biologic in a sample. The assays of the present invention are particularly advantageous for detecting and measuring the presence or level of biologics that target complex antigens including cell surface proteins, transmembrane proteins, heavily glycosylated proteins, multimeric proteins, and the like. As such, the present invention provides information for guiding treatment decisions for those subjects receiving therapy with a biologic agent and improves the accuracy of optimizing therapy, reducing toxicity, and/or monitoring the efficacy of therapeutic treatment to biologic therapy. The present invention also provides isolated soluble α4β7 integrin heterodimers and isolated soluble IL-12p40 monomers that are suitable for use in the assays described herein.

In certain aspects, the present invention provides a method for determining the presence or level of a biologic in a sample, the method comprising:
  (a) contacting the sample with an unlabeled soluble antigen that binds to the biologic to form an unlabeled complex between the antigen and the biologic in the sample;
  (b) contacting the sample from step (a) with a labeled form of the biologic to form a labeled complex between the antigen and the labeled biologic;
  (c) subjecting the unlabeled and labeled complexes to size exclusion chromatography to separate the unlabeled and labeled complexes from free labeled biologic and to detect an amount of the free labeled biologic; and
  (d) comparing the amount of the free labeled biologic detected in step (c) to a standard curve of known amounts of the biologic, thereby determining the presence or level of the biologic in the sample.

In some embodiments, the biologic includes antibodies, antibody fragments, proteins, polypeptides, peptides, fusion proteins, multivalent binding proteins, antibody-drug conjugates, vaccines, nucleic acids, sugars, recombinant forms thereof, engineered forms thereof, and combinations thereof.

In certain embodiments, the antigen is a soluble version (e.g., a soluble fragment, variant, or monomeric form) of a membrane-bound protein, a glycosylated protein, a multimeric protein, an insoluble protein, a protein that is difficult to express or purify, and/or a large protein. In certain instances, the antigen is a soluble extracellular domain of a membrane-bound protein (e.g., a soluble cytokine receptor extracellular domain). In certain other instances, the antigen is a soluble homodimer or heterodimer comprising the extracellular domains of two membrane-bound proteins (e.g., a soluble integrin heterodimer). In yet other instances, the antigen is a soluble protein that does not multimerize and remains in monomeric form once isolated and/or purified (e.g., a soluble cytokine variant with one or more cysteine residues mutated to minimize or eliminate the formation of multimers).

In other embodiments, the sample is a whole blood, serum, or plasma sample, e.g., from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In particular embodiments, the standard curve is generated by incubating the antigen and the labeled biologic with a (e.g., two-fold) serial dilution of known amounts of the biologic. In certain embodiments, the area under the curve (AUC) of the free labeled biologic is plotted against (e.g., the logarithm of) known amounts of the biologic obtained from the standard curve, and the level of the biologic in the sample is calculated by interpolation, e.g., based upon the size of the peak area of the free labeled biologic. In other embodiments, free label added to a stock solution of labeled biologic is used as a labeled biologic loading control. The ratio of the free labeled biologic to free label is plotted against known amounts of biologic.

In one particular embodiment, the presence and/or level of an anti-α4β7 integrin drug (e.g., vedolizumab) is determined with an indirect homogeneous mobility shift assay using size exclusion chromatography as described herein.

In another particular embodiment, the presence and/or level of an anti-IL12p40 drug (e.g., ustekinumab) is determined with an indirect homogeneous mobility shift assay using size exclusion chromatography as described herein.

In other embodiments, the presence and/or level of anti-drug antibodies (ADA) (e.g., autoantibodies including HACA, HAHA, etc.) that are generated against anti-α4β7 integrin drugs and anti-IL12p40 drugs as well as other biologics is determined with a homogeneous mobility shift assay as described in, e.g., U.S. Pat. Nos. 8,574,855 and 8,865,417, and U.S. Patent Publication Nos. 2014/0051184 and 2014/0141983, the disclosures of which are hereby incorporated by reference in their entirety for all purposes.

In other aspects, the present invention provides an isolated soluble α4 integrin polypeptide comprising an amino acid sequence having at least 80% identity to SEQ ID NO:1 or SEQ ID NO:3. In yet other aspects, the present invention provides an isolated soluble β7 integrin polypeptide comprising an amino acid sequence having at least 80% identity to SEQ ID NO: 2 or SEQ ID NO:4.

In particular embodiments, the present invention provides an isolated soluble α4β7 integrin heterodimer comprising:
(a) an α4 integrin polypeptide having an amino acid sequence that has at least 80% identity to SEQ ID NO:1, wherein the α4 integrin polypeptide is linked to a first member of a binding pair (e.g., SEQ ID NO:3), and
(b) a β7 integrin polypeptide having an amino acid sequence that has at least 80% identity to SEQ ID NO:2, wherein the β7 integrin polypeptide is linked to a second member of the binding pair (e.g., SEQ ID NO:4).

In certain other aspects, the present invention provides an isolated soluble IL-12p40 polypeptide comprising an amino acid sequence having at least 80% identity to SEQ ID NOS:6, 7, 11, 12, or 13.

In particular embodiments, the unlabeled soluble antigen used in the indirect homogeneous mobility shift assays of the present invention comprise the isolated soluble α4β7 integrin heterodimers or isolated soluble IL-12p40 polypeptides described herein.

In further aspects, the present invention provides expression vectors encoding the soluble polypeptides described herein, host cells comprising the expression vectors, and methods for generating the soluble polypeptides described herein.

Other objects, features, and advantages of the present invention will be apparent to one of skill in the art from the following detailed description and figures.

Using vedolizumab ("VLM" or "Vedo") as a non-limiting example, in the first step, serum is added to a 96 well plate along with integrin α4β7 and diluent buffer. In the second step, labeled VLM (e.g., Vedo Alexa 488) is added. The samples are then injected sequentially on an HPLC size exclusion column.

Figure 2:
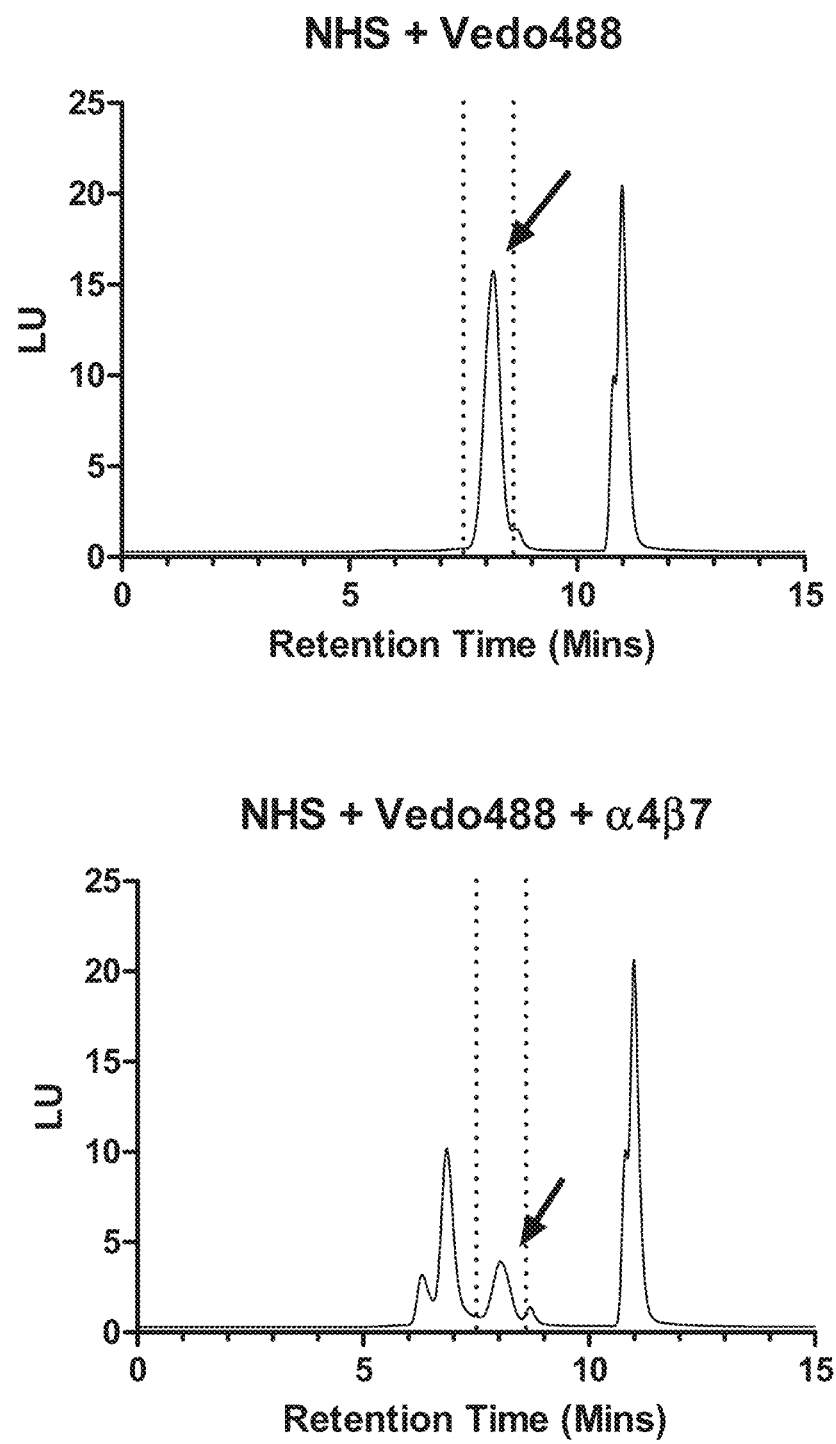

FIG. 2 shows the chromatograms of Vedo Alexa 488 (left) and Vedo Alexa 488 plus integrin α4β7 antigen (right) with retention times (x-axis) and light units (y-axis) of one embodiment of the present invention. Both are in 4% normal human serum. Note that the antigen binds up the majority of the labeled VLM.

Figure 3:
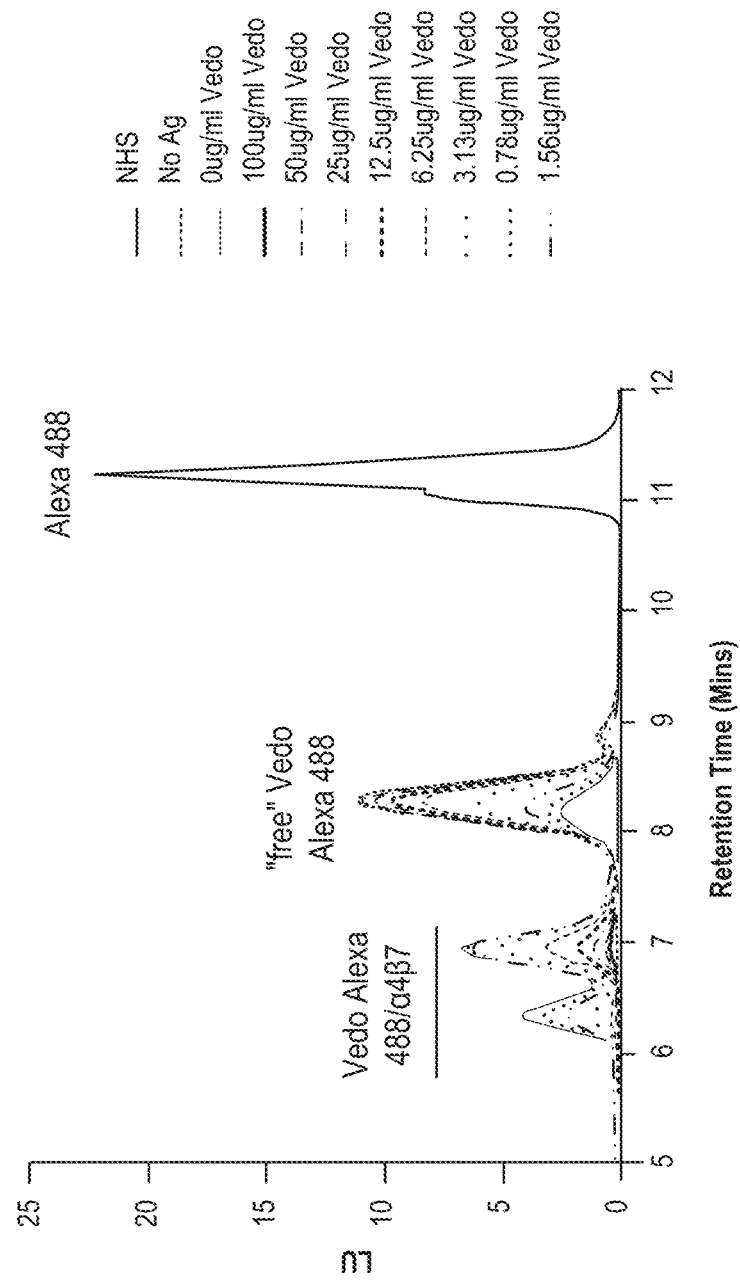

FIG. 3 shows the chromatograms from standard curve overlays with the retention time (x-axis) and light units (y-axis) of the various components of a VLM assay in one embodiment of the present invention. "Vedo Alexa 488/α4β7"=Alexa Fluor® 488-labeled VLM bound to a soluble α4β7 heterodimer. "Alexa 488"=Blocked (e.g., inactivated) Alexa Fluor® 488 loading control." Note that the free Vedo Alexa 488 peak area gets larger when there is more therapeutic VLM present.

Figure 4:
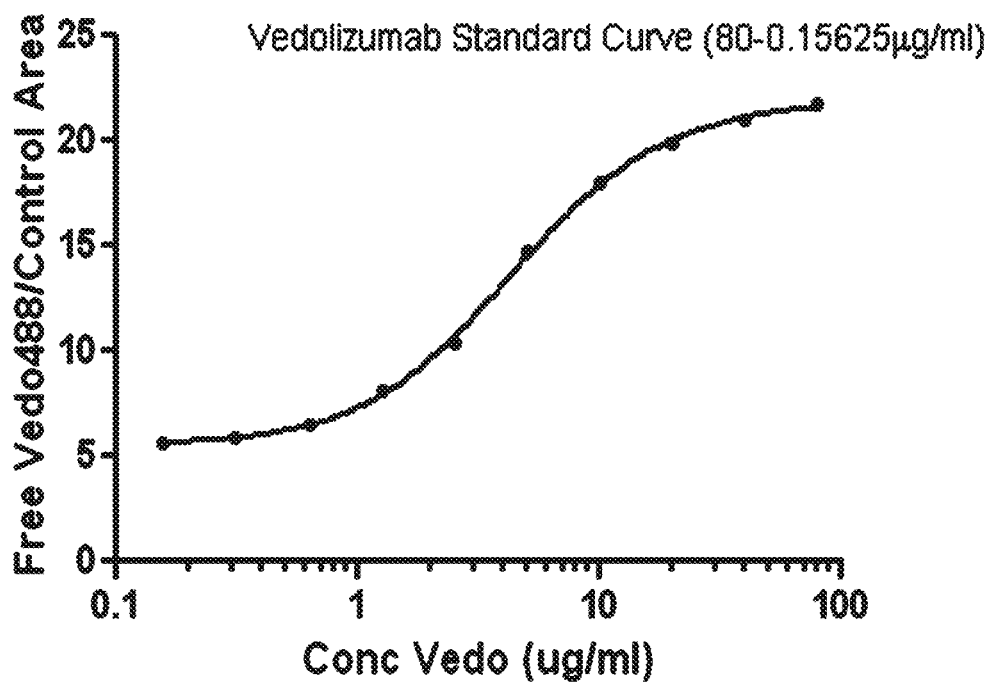

FIG. 4 shows a VLM standard curve in one embodiment of the present invention. The standard curve was generated using a serial dilution of VLM with a concentration range of between 0.15625 µg/ml and 80 µg/ml.

FIG. 5 shows a VLM drug assay validation in one embodiment of the present invention. The limit of blank (LOB), limit of detection (LOD), lower limit of quantitation (LLOQ), and upper limit of quantitation (ULOQ) were calculated using a standard curve generated from a serial dilution of VLM with a concentration range of between 0.15625 µg/ml and 80 µg/ml.

FIG. 6 shows the intra-assay precision and accuracy of the VLM drug assay in one embodiment of the present invention.

Figure 7:
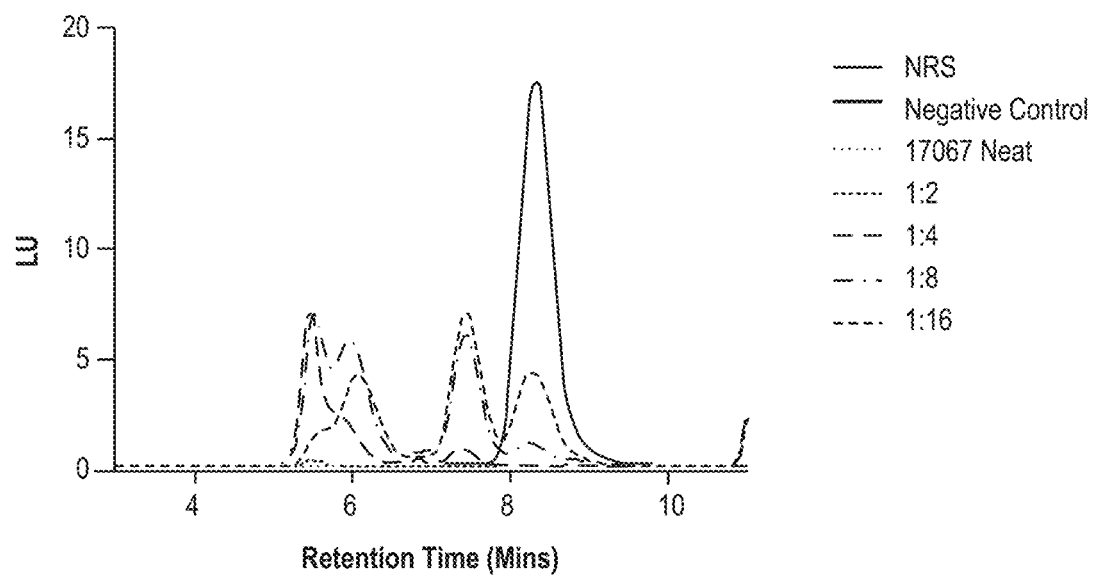
Figure 7:
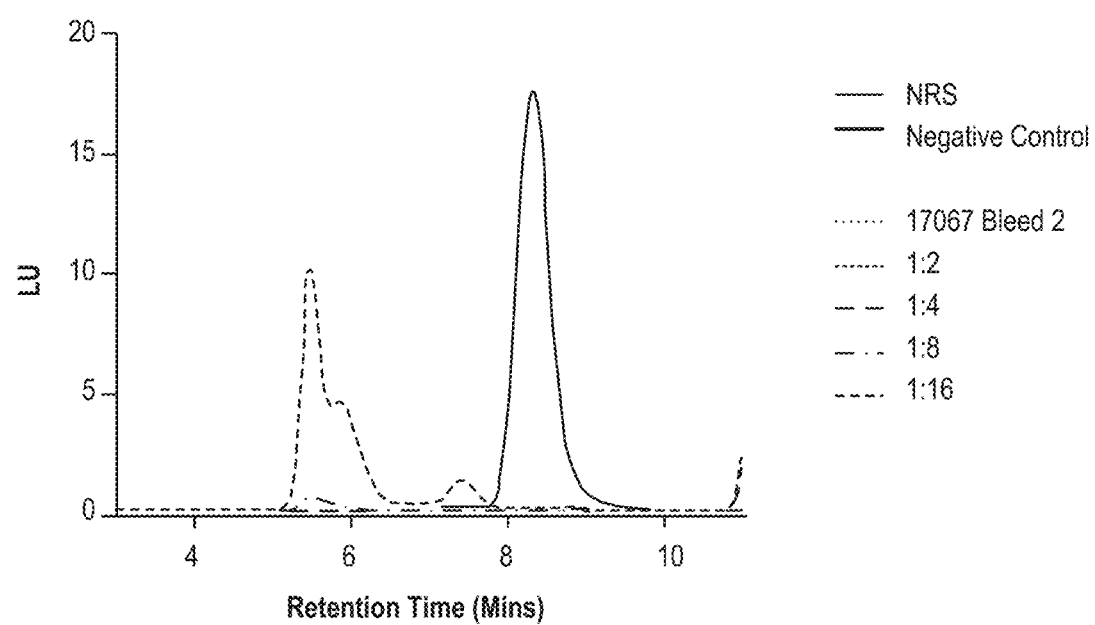

FIG. 7 shows the retention time (x-axis) and light units (y-axis) of an anti-vedolizumab autoantibody (ATV) assay in one embodiment of the present invention.

Figure 8:
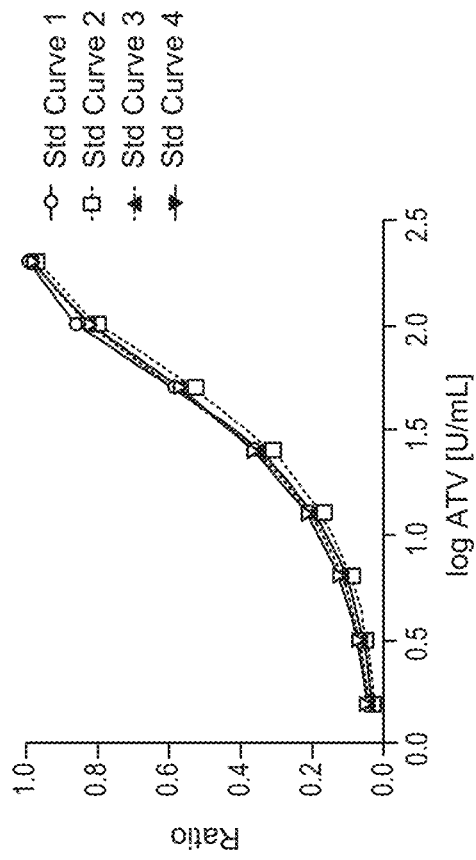

FIG. 8 shows the validation of the ATV assay in one embodiment of the present invention.

FIG. 9 shows the validation of the ATV assay in one embodiment of the present invention.

FIG. 10 shows the interassay precision of the ATV assay in one embodiment of the present invention.

FIG. 11 shows a ustekinumab (UTK) drug assay validation in one embodiment of the present invention. The limit of blank (LOB), limit of detection (LOD), lower limit of quantitation (LLOQ), and upper limit of quantitation (ULOQ) were calculated using a standard curve generated from a serial dilution of UTK with a concentration range of between 0.078 µg/ml and 40 µg/ml.

Figure 12:
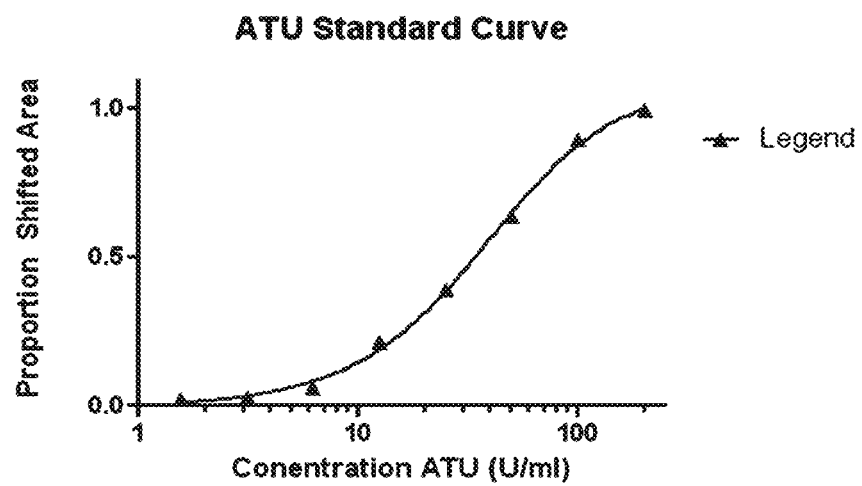

FIG. 12 shows the validation of the assay for autoantibodies to ustekinumab (ATU) in one embodiment of the present invention.

Figure 13:
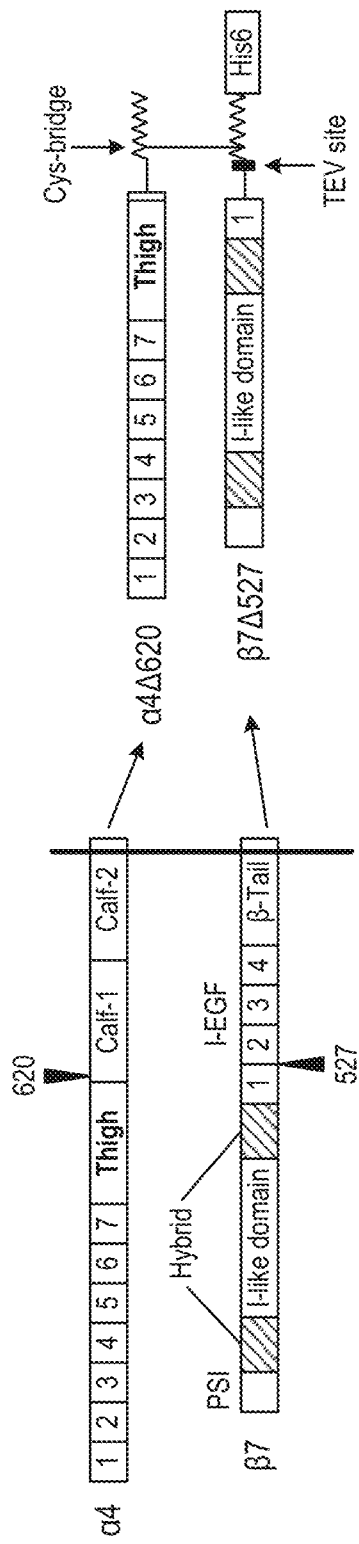

FIG. 13 shows a schematic diagram of the exemplary embodiments of the soluble α4 integrin antigen and soluble β7 integrin antigen of the present invention. Left: Full-length proteins. Right: Truncated α4β7 integrin heterodimer with a cysteine bridge of the ACID-BASE peptide.

Figure 14:
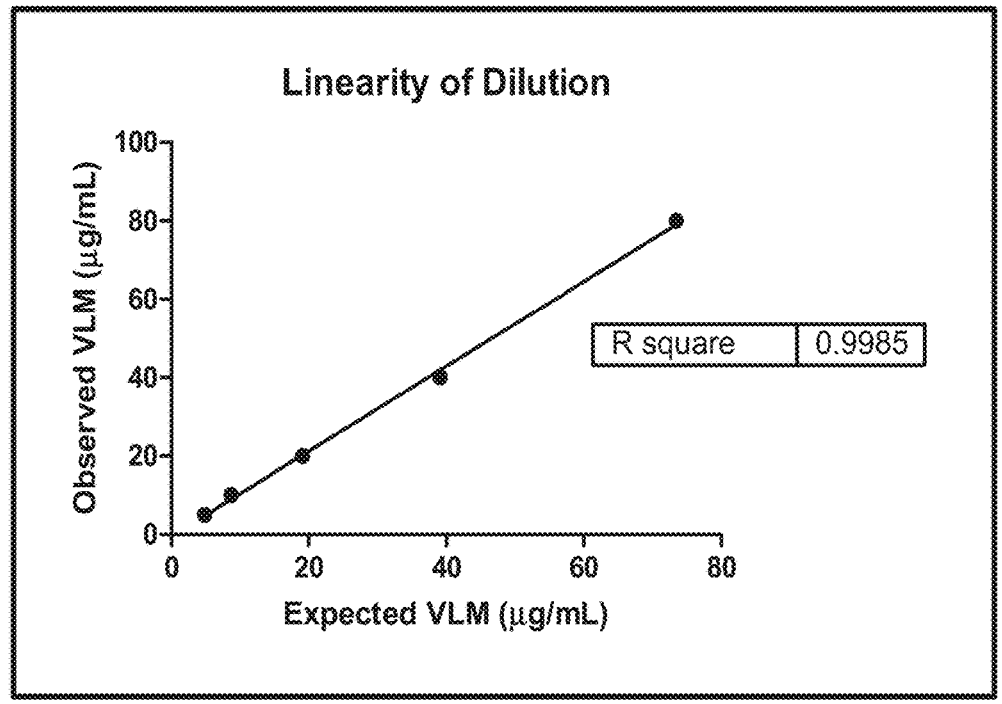
Figure 14:
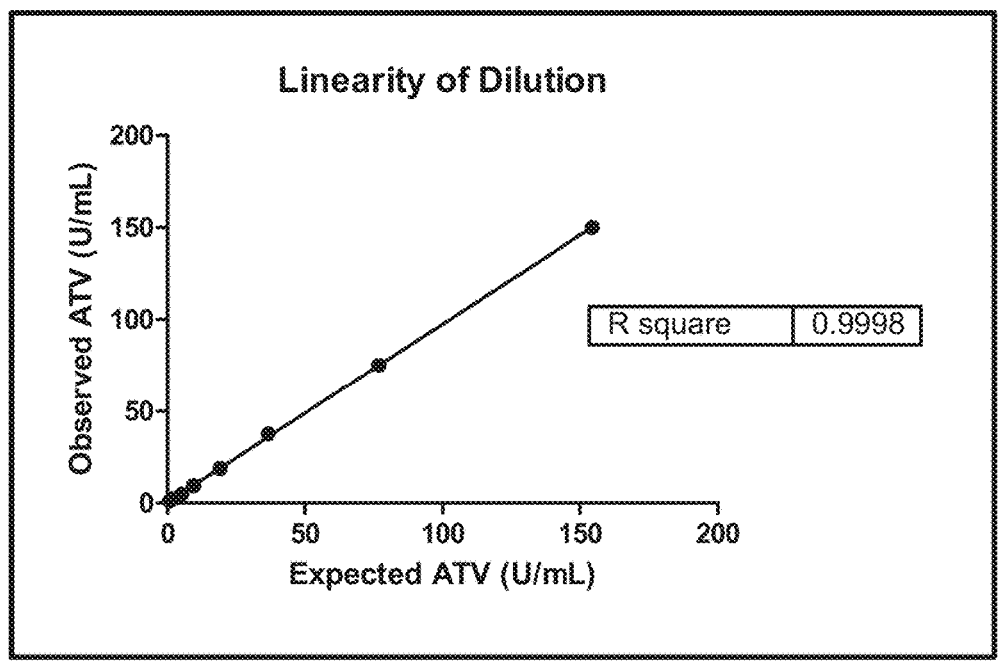

FIGS. 14A and 14B show the linearity of drug dilution in human serum for (A) VLM and (B) autoantibodies to vedolizumab (ATV).

Figure 15A:
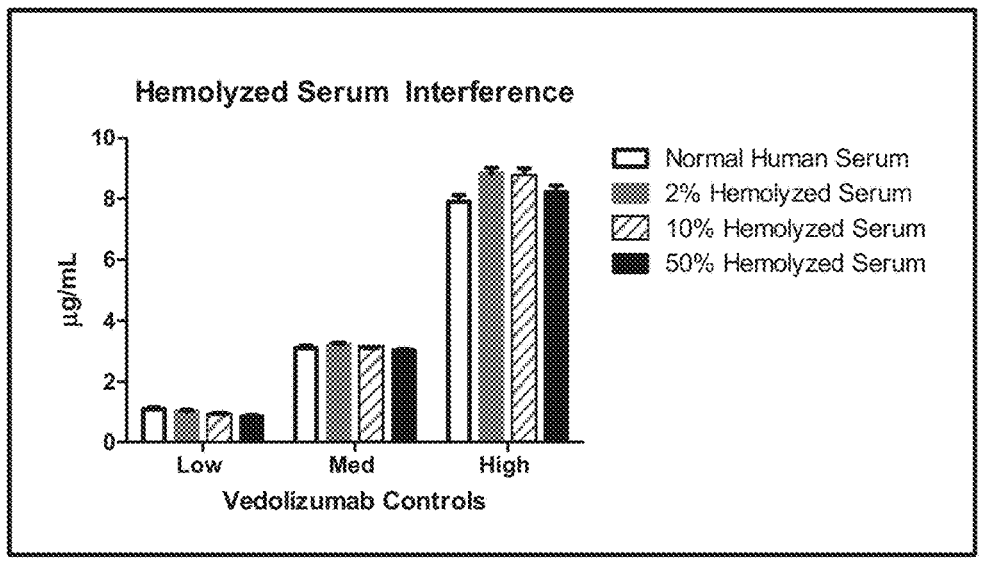
Figure 15B:
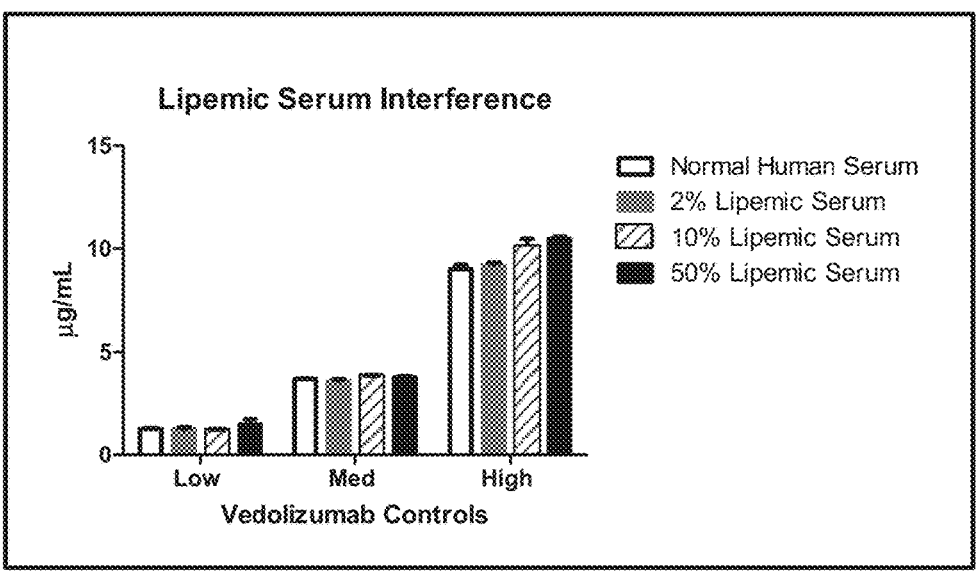
Figure 15C:
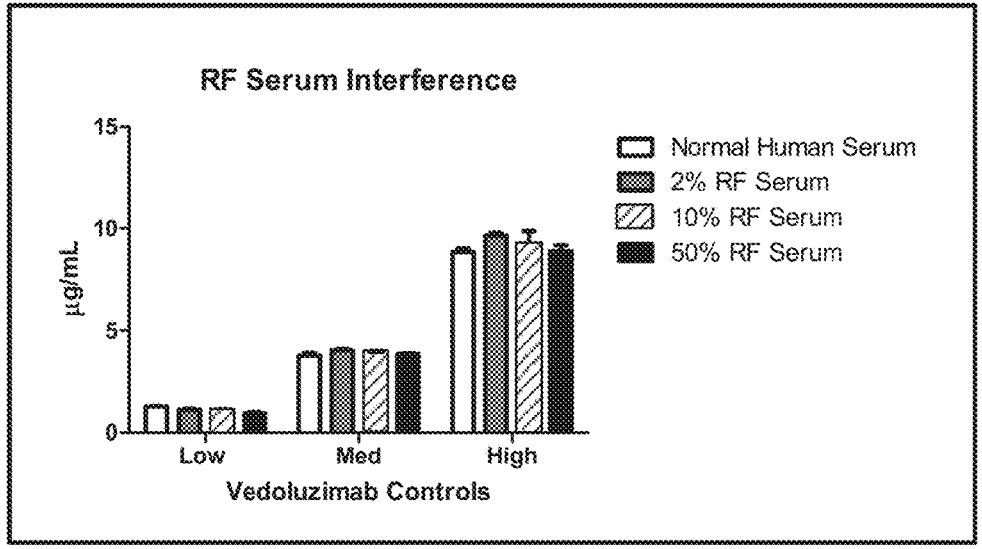

FIGS. 15A, 15B and 15C show an analysis of common interfering agents in serum: (A) hemolyzed serum interference; (B) lipemic serum interference; and (C) RF serum interference.

Figure 16:
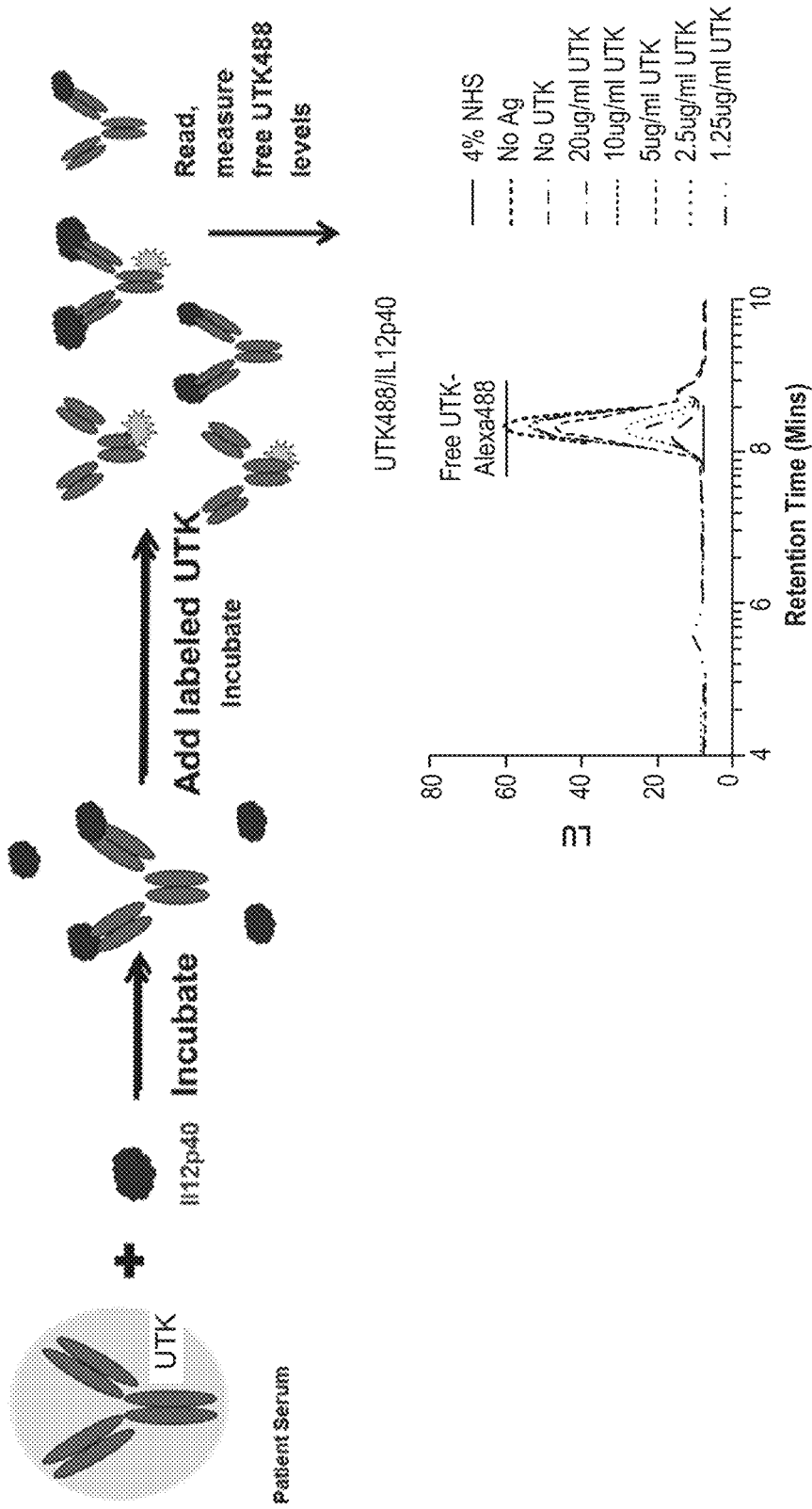

FIG. 16 shows the principle of the ustekinumab (UTK) homogeneous mobility shift assay (HMSA).

Figure 17:
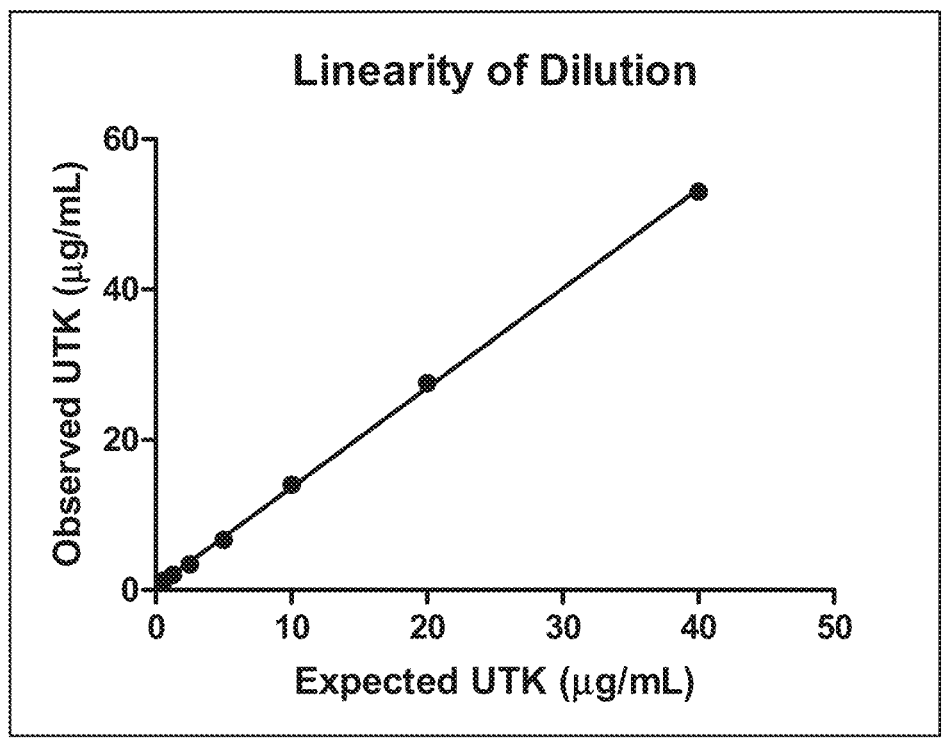
Figure 17:
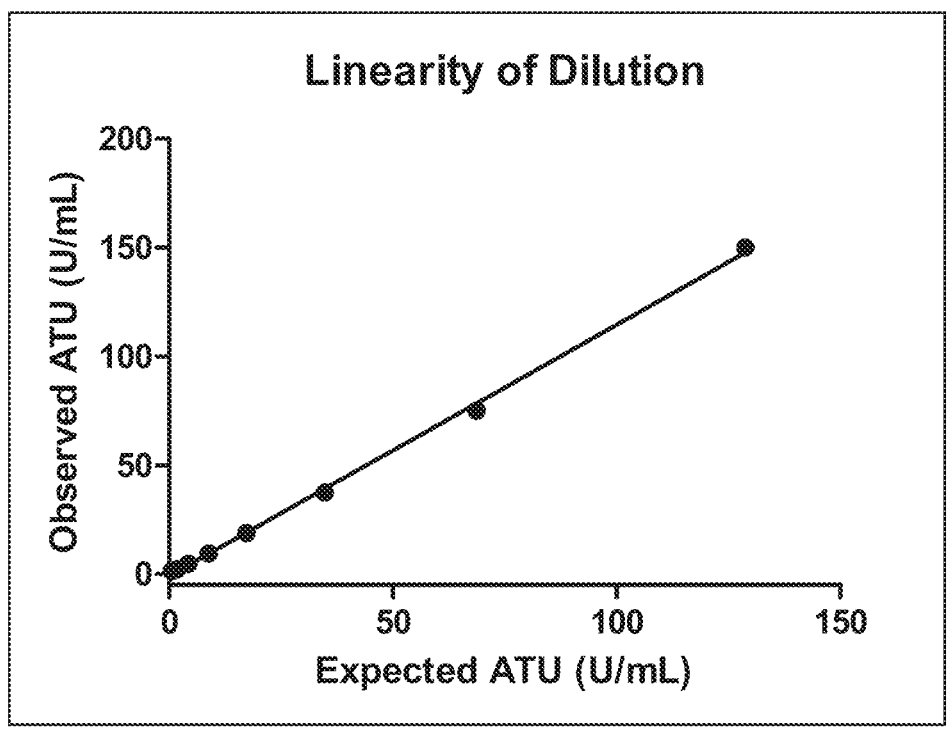

FIGS. 17A and 17B show the linearity of dilution in normal human serum for (A) UTK and (B) autoantibodies to ustekinumab (ATU).

Figure 18:
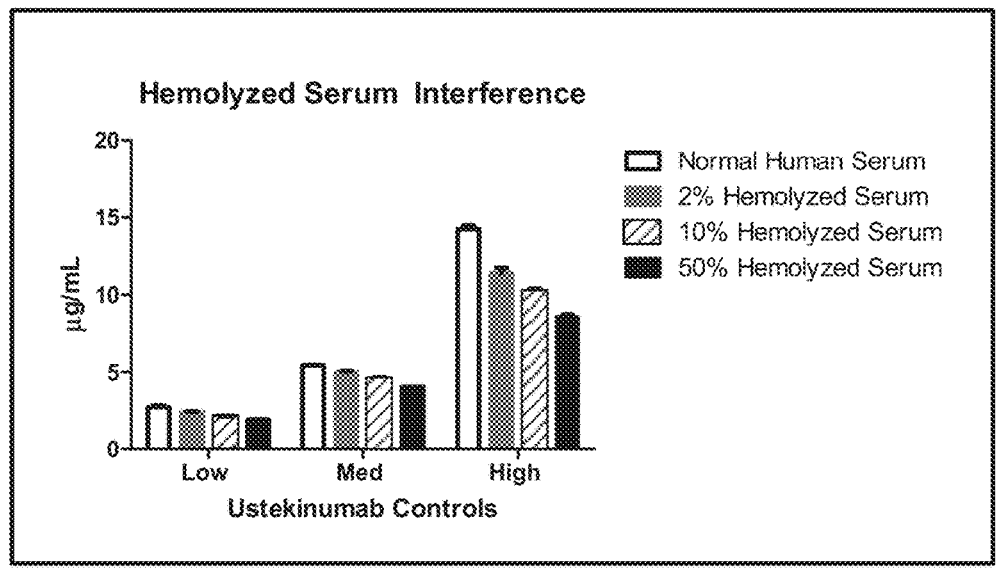
Figure 18:
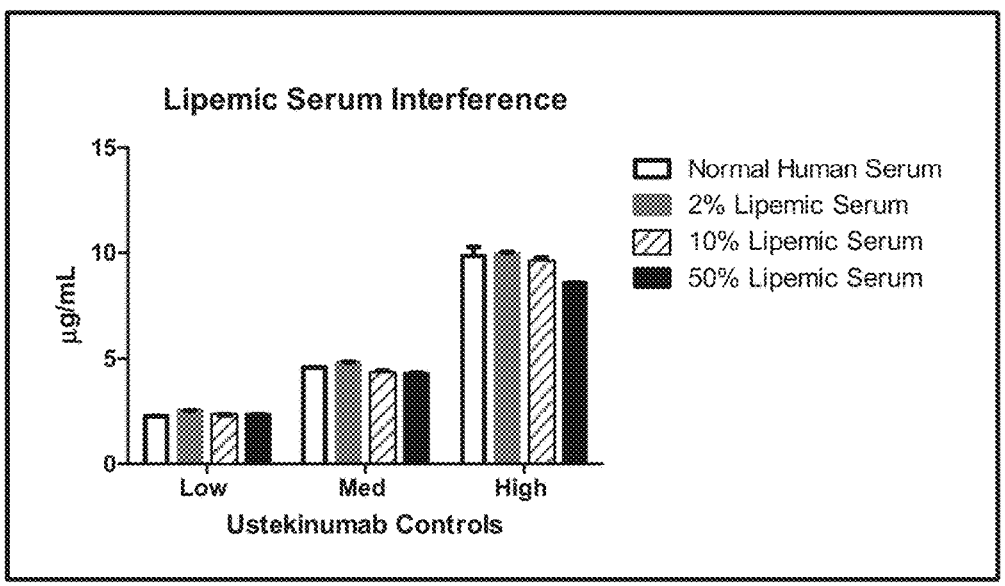
Figure 18:
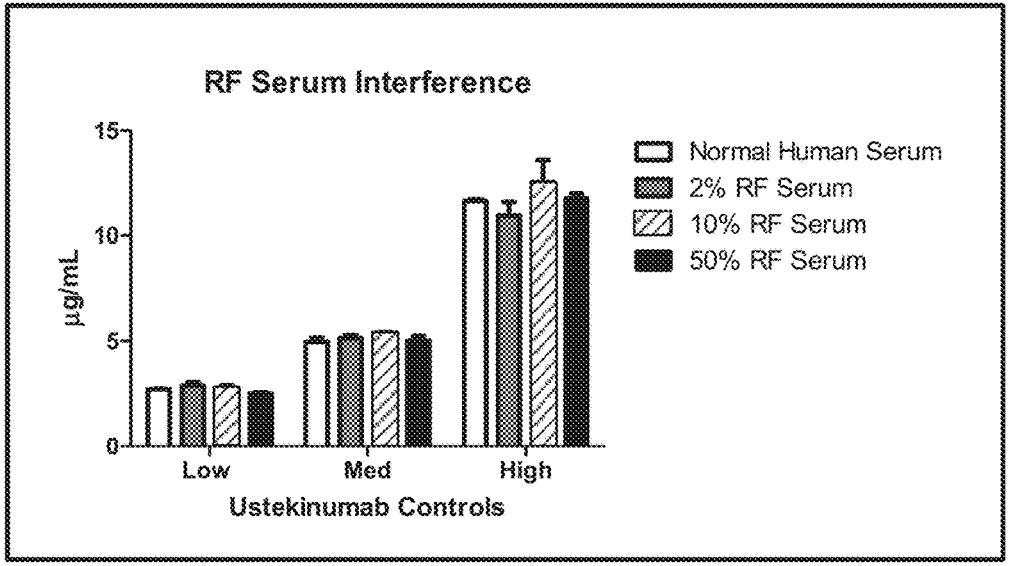

FIGS. 18A, 18B and 18C show an analysis of common interfering agents in serum: (A) hemolyzed serum interference; (B) lipemic serum interference; and (C) RF serum interference.

Figure 19:
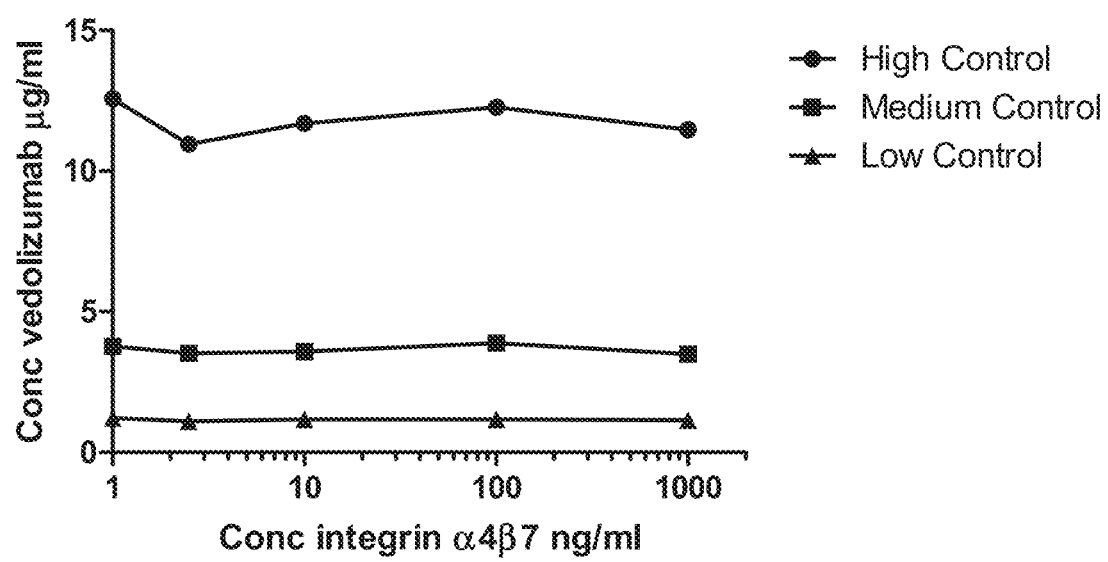

FIG. 19 shows integrin $\alpha 4\beta 7$ substrate interference in one embodiment of the VLM assay of the present invention.

Figure 20:
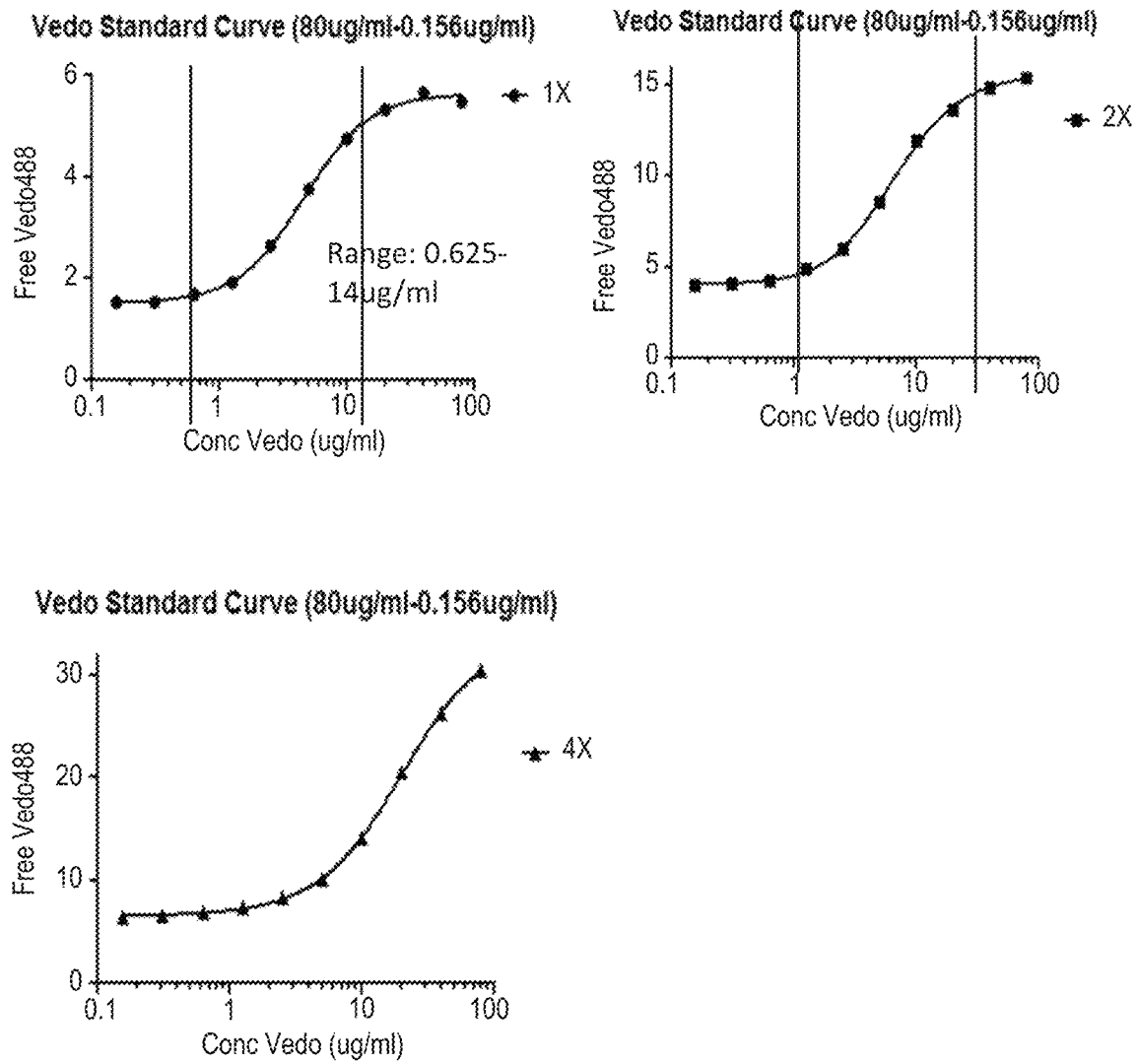

FIG. 20 shows standard curves using fixed amounts of labeled vedolizumab ("Vedo488") and integrin $\alpha 4\beta 7$ antigen (top left), as well as 2-fold increased (top right) or 4-fold increased (bottom left) amounts of both reagents. Note that the top end of the curve saturates at higher VLM concentrations. Similarly, the bottom end flattens out at slightly higher levels of VLM.

DETAILED DESCRIPTION OF THE INVENTION

I. Introduction

The present invention is based in part on the discovery that an indirect homogeneous mobility shift assay (HMSA) using size exclusion chromatography is particularly advantageous for measuring the presence or level of biologics that target antigens having one or more of the following characteristics: cell surface or membrane-bound, (heavily) glycosylated, multimeric (e.g., forms heterodimers, homodimers, etc.), insoluble, difficult to express, difficult to purify, large in size, and combinations thereof. In certain aspects, the use of a soluble form (e.g., a soluble fragment, variant, or monomer) of the antigen overcomes the difficulties and limitations associated with antigens having one or more of the above characteristics and enables the precise and accurate measurement of any biologic of interest in a sample from a patient receiving therapy with that biologic.

The principle behind the indirect assays of the present invention is that the amount of (unlabeled) biologic in a sample (e.g., serum) obtained from a patient receiving biologic therapy determines how much unlabeled antigen remains free to bind to a labeled form of the biologic. By tracking changes in the area of the free (unbound) labeled biologic, the presence or level of (unlabeled) biologic in the patient sample can be determined. More particularly, the relative amount (e.g., ratio) of labeled and unlabeled biologic determines how much antigen is bound to each and determines the amount (e.g., peak area) of free labeled biologic following size exclusion chromatography. The amount (e.g., peak area) of the free labeled biologic can then be compared to a standard curve of known amounts of the biologic to provide an accurate measurement of biologic levels in the patient sample with high sensitivity and dynamic range. In certain embodiments, the size of the peak area of free labeled biologic following size exclusion chromatography is calculated and compared to the standard curve to interpolate the concentration of biologic in a patient sample.

The importance of measuring serum concentrations of biologics is illustrated by the fact that the FDA requires pharmacokinetic and tolerability (e.g., immune response) studies to be performed during clinical trials. The present invention also finds utility in monitoring patients receiving these drugs to make sure they are getting the right dose, that the drug isn't being cleared from the body too quickly, and that they are not developing an immune response against the drug. Furthermore, the present invention is useful in guiding the switch between different drugs due to failure with the initial drug.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise.

The terms "competition," "competition-based," and "indirect" are used interchangeably herein to refer to an assay of the present invention for determining the presence or level of (unlabeled) biologic in a sample that relies on detecting the amount of free (unbound) labeled biologic remaining in the sample after unlabeled antigen and labeled biologic are added (sequentially) to the sample.

The terms "VLM," "VDZ," and "Vedo" are used interchangeably herein to refer to vedolizumab.

The terms "biologic" or "biologic agent" or "biological drug" as used herein encompass products and substances produced from or extracted from a biological system (e.g., a living organism). Non-limiting examples of biologics include antibodies, antibody fragments, proteins, polypeptides, peptides, fusion proteins (e.g., Ig fusion proteins or Fc fusion proteins), multivalent binding proteins (e.g., DVD Ig), antibody-drug conjugates, vaccines, nucleic acids, sugars, recombinant forms thereof, engineered forms thereof, and combinations thereof.

The term "antibody" includes large (150 kDa) "Y-shaped" molecules that consist of two identical light chains (~220 amino acids) and two identical heavy chains (~440 amino acids) that are held together by a combination of covalent (disulfide) and non-covalent interactions. Each light and heavy chain consists of repeating segments of constant or variable regions that contain one intrachain disulfide bond. The variable regions are located at the N-termini of the light and heavy chains, while the constant domains are located at the C-termini of the light and heavy chains. The N-termini of the light and heavy chains come together to form the antigen-binding site. The light chain is comprised of one variable domain and one constant domain and the heavy chain is comprised of one variable domain and three constant domains. Located at the ends of the "Y" are two identical (bivalent) antigen-binding sites. The distance between the two antigen binding sites varies due to the flexible hinge region, and as a result, the antigen binding efficiency can be greatly increased. The formation of the antigen-binding region is caused by the pairing of the variable region from the heavy chain ($V_H$) with the variable region of the light chain ($V_L$). Variations in amino acid sequences of the variable regions are responsible for the vast diversity of antigen-binding sites, and the greatest variability occurs throughout three hypervariable regions, termed complementary determining regions (CDRs). The tail region of the antibody, known as the $F_C$ region, is comprised of two constant domains ($C_H2$, and $C_H3$) from each of the heavy chains. The $F_C$ region is responsible for recruiting effector functions through binding of $F_C$ receptors on neutrophils and macrophages.

The term "antigen" includes any molecule, agent, or substance that (e.g., specifically) binds to or interacts with a biologic. As one non-limiting example, the antigen comprises a soluble fragment, variant, or monomer of a membrane-bound protein, a glycosylated protein, a multimeric protein, an insoluble protein, a protein that is difficult to express or purify, and/or a large protein. As another non-limiting example, the antigen comprises a soluble fragment of a cell surface molecule such an integrin receptor (e.g., α4β7 integrin), wherein the soluble fragment contains one or more extracellular domains of the corresponding full-length molecule (e.g., a soluble α4β7 antigen heterodimer comprising extracellular domain sequences from the corresponding full-length α4 and β7 proteins). As yet another non-limiting example, the antigen comprises a cytokine such as TNFα or a subunit thereof such as IL-12p40 that does not form homodimers or heterodimers.

The term "size exclusion chromatography" or "SEC" includes a chromatographic method in which molecules in solution are separated based on their size and/or hydrodynamic volume. It is applied to large molecules or macromolecular complexes such as proteins and their conjugates. Typically, when an aqueous solution is used to transport the sample through the column, the technique is known as gel filtration chromatography.

The term "complex" includes an antigen bound (e.g., by non-covalent means) to a biologic (e.g., an unlabeled or labeled biologic), and a biologic (e.g., a labeled biologic) bound (e.g., by non-covalent means) to an autoantibody against the biologic.

As used herein, an entity that is modified by the term "labeled" includes any antigen, molecule, protein, enzyme, antibody, antibody fragment, cytokine, or related species that is conjugated with another molecule or chemical entity that is empirically detectable. Chemical species suitable as labels include, but are not limited to, fluorescent dyes, e.g. Alexa Fluor® dyes such as Alexa Fluor® 488, quantum dots, optical dyes, luminescent dyes, and radionuclides, e.g., $^{125}$I.

The phrase "fluorescence label detection" includes a means for detecting a fluorescent label. Means for detection include, but are not limited to, a spectrometer, a fluorimeter, a photometer, and a detection device commonly incorporated with a chromatography instrument such as, but not limited to, size exclusion-high performance liquid chromatography, such as, but not limited to, an Agilent-1200 HPLC System.

The term "subject," "patient," or "individual" typically includes humans, but also includes other animals such as, e.g., other primates, rodents, canines, felines, equines, ovines, porcines, and the like.

The term "sample" includes any biological specimen obtained from an individual. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), cellular extracts thereof, and an immunoglobulin enriched fraction derived from one or more of these bodily fluids or tissues. In some embodiments, the sample is whole blood, a fractional component thereof such as plasma, serum, or a cell pellet, or an immunoglobulin enriched fraction thereof. One skilled in the art will appreciate that samples such as serum samples can be diluted prior to the analysis. In certain embodiments, the sample is obtained by isolating PBMCs and/or PMN cells using any technique known in the art. In certain other embodiments, the sample is a tissue biopsy such as, e.g., from a site of inflammation such as a portion of the gastrointestinal tract or synovial tissue.

The term "isolated," when applied to a nucleic acid or polypeptide, denotes that the nucleic acid or polypeptide is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A polypeptide that is the predominant species present in a preparation is substantially purified. In particular, an isolated gene is separated from open reading frames that flank the gene and encode a protein other than the gene of interest. The term "purified" denotes that a nucleic acid or polypeptide gives rise to essentially one band in an electrophoretic gel. Particularly, it means that the nucleic acid or polypeptide is at least about 80% pure, at least about 85% pure, at least about 90% pure, at least about 95% pure, or at least about 99% pure.

The term "soluble," in the context of a polypeptide, refers to polypeptide that can be prepared in a soluble and functional form using a host cell or a cell-free protein synthesis system. For instance, a soluble polypeptide does not form insoluble aggregates comprising misfolded and/or functionally inactive polypeptides.

The term "nucleic acid" or "polynucleotide" includes deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to include a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, truncated forms, or fragments thereof, wherein the amino acid residues are linked by covalent peptide bonds.

The term "amino acid" refers to naturally-occurring and unnatural amino acids, as well as amino acid analogs and amino acid mimetics that function in a manner similar to the naturally occurring amino acids.

Amino acids may be referred to herein by either their name, their commonly known three letter symbols or by the one-letter symbols recommended by the IUPAC-IUB Biochemical Nomenclature Commission. Additionally, nucleotides may be referred to by their commonly accepted single-letter codes.

The steps of the methods of the present invention do not necessarily have to be performed in the particular order in which they are presented. A person of ordinary skill in the art would understand that other orderings of the steps of the methods of the invention are encompassed within the scope of the present invention.

Brackets, "[ ]" indicate that the species within the brackets are referred to by their concentration.

III. Description of the Embodiments

The present invention provides novel indirect homogeneous mobility shift assays for detecting and measuring the presence or level of a biologic in a sample. The assays of the present invention are particularly advantageous for detecting the presence or level of biologics that target complex or large antigens including cell surface proteins, transmembrane proteins, heavily glycosylated proteins, and multimeric proteins, as well as antigens that cannot be purified, impure antigens, and partially or substantially purified antigens. The present invention also provides isolated soluble α4β7 integrin heterodimers and isolated soluble IL-12p40 monomers that are suitable for use in the assays described herein.

In one aspect, the present invention provides a method for determining the presence or level of a biologic in a sample, the method comprising:
(a) contacting the sample with an unlabeled soluble antigen that binds to the biologic to form an unlabeled complex (e.g., a plurality of unlabeled complexes) between the antigen and the biologic in the sample;
(b) contacting the sample from step (a) with a labeled form of the biologic ("labeled biologic") to form a labeled complex (e.g., a plurality of labeled complexes) between the antigen and the labeled biologic;
(c) subjecting the (e.g., plurality of) unlabeled and labeled complexes to size exclusion chromatography to separate the (e.g., plurality of) unlabeled and labeled complexes from free labeled biologic and to detect an amount of the free labeled biologic; and
(d) comparing the amount of the free labeled biologic detected in step (c) to a standard curve of known amounts of the biologic, thereby determining the presence or level of the biologic in the sample.

In some embodiments, the biologic includes antibodies, antibody fragments, proteins, polypeptides, peptides, fusion proteins, multivalent binding proteins, antibody-drug conjugates, vaccines, nucleic acids, sugars, recombinant forms thereof, engineered forms thereof, and combinations thereof. In particular embodiments, the biologic comprises an antibody (e.g., a monoclonal antibody) or a fragment thereof (e.g., an antigen-binding fragment of a monoclonal antibody) or a conjugate thereof (e.g., an antibody-drug conjugate). Non-limiting examples of antibody-based biologics are shown in Table 1.

In particular embodiments, the method of the present invention detects the presence of and/or measures the level of unbound (free) biologic in a sample, e.g., the population of biologic in a sample that is not bound to its (endogenous) target antigen or a fragment thereof.

In certain embodiments, the antigen is a soluble version (e.g., a soluble fragment, variant, or monomeric form) of a membrane-bound protein, a (heavily) glycosylated protein, a multimeric protein, an insoluble protein, a protein that is difficult to express or purify, and/or a large protein. In certain instances, the antigen is a soluble extracellular domain of a membrane-bound protein (e.g., a soluble cytokine receptor extracellular domain). In certain other instances, the antigen is a soluble homodimer or heterodimer comprising the extracellular domains of two membrane-bound proteins (e.g., a soluble integrin heterodimer). In yet other instances, the antigen is a soluble protein that does not multimerize and remains in monomeric form once isolated and/or purified (e.g., a soluble cytokine variant with one or more cysteine residues mutated to minimize or eliminate the formation of multimers).

In some embodiments, the antigen is a soluble fragment (e.g., extracellular domain) of a cell surface molecule such as, e.g., a cell adhesion molecule (CAM). Non-limiting examples of CAMs include immunoglobulin superfamily (IgSF) CAMs, integrins, cadherins, and selectins.

IgSF CAMs are any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include mucosal addressin cell adhesion molecule 1 (MADCAM1), neural cell adhesion molecules (NCAMs; e.g., NCAM-120, NCAM-125, NCAM-140, NCAM-145, NCAM-180, NCAM-185, etc.), intercellular adhesion molecules (ICAMs, e.g., ICAM-1, ICAM-2, ICAM-3, ICAM-4, and ICAM-5), vascular cell adhesion molecule-1 (VCAM-1), platelet-endothelial cell adhesion molecule-1 (PECAM-1), L1 cell adhesion molecule (L1CAM), cell adhesion molecule with homology to L1 CAM (close homolog of L1) (CHL1), sialic acid binding Ig-like lectins (SIGLECs; e.g., SIGLEC-1, SIGLEC-2, SIGLEC-3, SIGLEC-4, etc.), nectins (e.g., Nectin-1, Nectin-2, Nectin-3, etc.), and nectin-like molecules (e.g., Nec1-1, Nec1-2, Nec1-3, Nec1-4, and Nec1-5.

Integrins are transmembrane αβ heterodimers and at least 18 α and eight β subunits are known in humans, generating 24 heterodimers. The α and β subunits have distinct domain structures, with extracellular domains from each subunit contributing to the ligand-binding site of the heterodimer. Non-limiting examples of integrins include $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_4\beta_7$, $\beta_E\beta_7$, $\alpha_6\beta_4$, $\alpha_L\beta_2$, $\alpha_M\beta_2$, $\alpha_X\beta_2$, and $\alpha_D\beta_2$.

In particular embodiments, the antigen is an α4β7 integrin and the biologic is an anti-α4β7 integrin drug such as vedolizumab (VLM). In certain instances, the soluble fragment of the α4β7 integrin that binds to the anti-α4β7 integrin drug comprises an α4 fragment comprising an amino acid sequence having at least 80% identity to SEQ ID NO:1 or SEQ ID NO:3 and/or a β7 fragment comprising an amino acid sequence having at least 80% identity to SEQ ID NO: 2 or SEQ ID NO:4.

In other embodiments, the antigen is an α4β1 integrin and the biologic is an anti-α4β1 integrin drug such as natalizumab. In certain instances, the soluble fragment of the α4β1 integrin that binds to the anti-α4β1 integrin drug comprises a heterodimer of the extracellular domains of the α4 and β1 subunits.

Cadherins are calcium-dependent transmembrane proteins that play important roles in cell adhesion, forming adherens junctions to bind cells within tissues together. Non-limiting examples of cadherins include E-cadherin, N-cadherin, N-cadherin 2, and P-cadherin.

Selectins are heterophilic CAMs that bind fucosylated carbohydrates, e.g., mucins. The three family members are E-selectin (endothelial), L-selectin (leukocyte), and P-selectin (platelet).

In other embodiments, the antigen is a soluble fragment (e.g., extracellular domain) of a cell surface molecule such as, e.g., a cytokine receptor.

Non-limiting examples of cytokine receptors include type I cytokine receptors, type II cytokine receptors, members of the immunoglobulin (Ig) superfamily, tumor necrosis factor receptors, chemokine receptors, and TGFβ receptors. Examples of type I cytokine receptors include, but are not limited to, interleukin receptors (e.g., IL-2 receptor, IL-3 receptor, IL-4 receptor, IL-5 receptor, IL-6 receptor, IL-7 receptor, IL-9 receptor, IL-11 receptor, IL-12 receptor, IL-13 receptor, IL-15 receptor, IL-21 receptor, IL-23 receptor, IL-27 receptor, etc.), colony stimulating factor receptors (e.g., erythropoietin receptor, GM-CSF receptor, G-CSF receptor, etc.), hormone receptors or neuropeptide receptors (e.g., growth hormone receptor, prolactin receptor, etc.), and other cytokine receptors such as oncostatin M receptor and leukemia inhibitory factor receptor. Examples of type II cytokine receptors include, but are not limited to, interferon receptors (e.g., interferon-alpha/beta receptor, interferon-gamma receptor, etc.) and interleukin receptors (e.g., IL-10 receptor, IL-20 receptor, IL-22 receptor, IL-28 receptor, etc.). Examples of immunoglobulin (Ig) superfamily receptors include, but are not limited to, IL-1 receptor, CSF1, c-kit receptor, and IL-18 receptor. Examples of tumor necrosis factor receptors include, but are not limited to, TNF receptor (CD120), lymphotoxin β receptor, CD134, CD40, FAS, TNFRSF6B, CD27, CD30, CD137, TNFRSF10A, TNFRSF10B, TNFRSF10C, TNFRSF10D, RANK, osteoprotegerin, TNFRSF12A, TNFRSF13B, TNFRSF13C, TNFRSF14, nerve growth factor receptor, TNFRSF17, TNFRSF18, TNFRSF19, TNFRSF21, TNFRSF25, and ectodysplasin A2 receptor. Examples of chemokine receptors include, but are not limited to, CXC chemokine receptors, CC chemokine receptors, C chemokine receptors, and CX3C chemokine receptors. Examples of TGFβ receptors include, but are not limited to, TGFβ receptor 1, TGFβ receptor 2, and TGFβ receptor 3.

In certain embodiments, the antigen is an IL-6 receptor and the biologic is an anti-IL-6 receptor drug such as tocilizumab. In certain instances, the soluble fragment of the IL-6 receptor that binds to the anti-IL-6 receptor drug comprises an extracellular domain of the IL-6 receptor.

In yet other embodiments, the antigen is a soluble fragment (e.g., extracellular domain) of a cluster of differentiation (CD) molecule. Non-limiting examples of CD molecules include CD3, CD4, CD8, CD11a, CD11b, CD14, CD15, CD16, CD19, CD20, CD22, CD24, CD25, CD30, CD31, CD34, CD38, CD45, CD56, CD61, CD91, CD114, CD117, CD182, and the like. In certain instances, the biologic that binds to a soluble fragment of a CD molecule is a member selected from the group consisting of visilizumab, priliximab, rituximab, ofatumumab, obinutuzumab, ibritumomab tiuxetan, tositumomab, ocrelizumab, veltuzumab, daclizumab, and combinations thereof.

In some embodiments, the antigen is a cytokine or a monomer thereof (e.g., a soluble cytokine variant with one or more cysteine residues mutated to minimize or eliminate the formation of multimers).

Non-limiting examples of cytokines include TNFα, TNF-related weak inducer of apoptosis (TWEAK), osteoprotegerin (OPG), IFN-α, IFN-β, IFN-γ, interleukins (e.g., IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27), adipocytokines (e.g., leptin, adiponectin, resistin, active or total plasminogen activator inhibitor-1 (PAI-1), visfatin, and retinol binding protein 4 (RBP4)), and the like.

In particular embodiments, the cytokine is a p40 subunit of IL-12 or IL-23 and the biologic is an anti-IL-12p40 drug such as ustekinumab (UTK). In certain instances, the cytokine is a p40 variant which comprises one or more cysteine residues mutated to minimize or eliminate the formation of multimers. In some instances, the p40 variant comprises an amino acid sequence having at least 80% identity to SEQ ID NOS:6, 7, 11, 12 or 13.

In other embodiments, the cytokine is TNFα and the biologic is an anti-TNFα drug. Non-limiting examples of anti-TNFα drugs include REMICADE® (infliximab), HUMIRA® (adalimumab), ENBREL® (etanercept), CIMZIA® (certolizumab pegol), SIMPONI® (golimumab), and combinations thereof.

The soluble antigens described herein can be produced by any method known to one of ordinary skill in the art, such as but not limited to, synthetic methods, such as solid phase and liquid phase synthesis, or recombinant biology methods.

In some embodiments, the sample is a whole blood, serum, or plasma sample, e.g., obtained from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In particular embodiments, the standard curve is generated by incubating the antigen and the labeled biologic with a (e.g., two-fold) serial dilution of known amounts of the biologic. In certain embodiments, the area under the curve (AUC) of the free labeled biologic is plotted against (e.g., the logarithm of) known amounts of the biologic obtained from the standard curve, and the level of the biologic in the sample is calculated by interpolation, e.g., based upon the size of the peak area of the free labeled biologic. In other embodiments, a ratio of the free labeled biologic to a loading control (e.g., free label) is determined and used to normalize the level of the biologic in the sample from the standard curve.

In certain embodiments, the size exclusion chromatography (SEC) is size exclusion-high performance liquid chromatography (SE-HPLC). In particular embodiments, the (e.g., plurality of) unlabeled and labeled complexes are eluted first through a stationary phase, followed by the free labeled biologic. The underlying principle of SEC is that molecules or complexes of different sizes will elute (filter) through a stationary phase at different rates. This results in the separation of a solution of molecules or complexes based on size. Provided that all the molecules or complexes are loaded simultaneously or near simultaneously, molecules or complexes of the same size elute together. Each size exclusion column has a range of molecular weights that can be separated. The exclusion limit defines the molecular weight at the upper end of this range and is where molecules or complexes are too large to be trapped in the stationary phase. The permeation limit defines the molecular weight at the lower end of the range of separation and is where molecules or complexes of a small enough size can penetrate into the pores of the stationary phase completely and all molecules or complexes below this molecular mass are so small that they elute as a single band.

In some instances, the eluent is collected in constant volumes, or fractions. The more similar the molecules or complexes are in size, the more likely they will be in the same fraction and not detected separately. Preferably, the collected fractions are examined by spectroscopic techniques to determine the concentration of the molecules or complexes eluted. Typically, the spectroscopy detection techniques useful in the present invention include, but are not limited to, fluorometry, refractive index (RI), and ultraviolet (UV). In certain instances, the elution volume decreases roughly linearly with the logarithm of the molecular hydrodynamic volume (i.e., heaver molecules or complexes come off first).

A biologic (e.g., therapeutic antibody) can be labeled with any of a variety of detectable group(s). In certain embodiments, a biologic is labeled with a fluorophore or a fluorescent dye. In other embodiments, a biologic is labeled with a luminescent tag, a metal, a radionuclide, and the like. Specific immunological binding of an antigen to a labeled biologic or the amount of free labeled biologic can be detected directly or indirectly. A signal from the direct or indirect label can be analyzed, e.g., using a spectrophotometer to detect color from a chromogenic substrate, a radiation counter to detect radiation such as a gamma counter for detection of $^{125}I$, or a fluorometer to detect fluorescence in the presence of light of a certain wavelength.

Non-limiting examples of fluorophores or fluorescent dyes include those listed in the Molecular Probes Catalogue, which is herein incorporated by reference (see, R. Haugland, *The Handbook—A Guide to Fluorescent Probes and Labeling Technologies*, $10^{th}$ Edition, Molecular probes, Inc. (2005)). Such exemplary fluorophores or fluorescent dyes include, but are not limited to, Alexa Fluor® dyes such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790, as well as other fluorophores including, but not limited to, Dansyl Chloride (DNS-Cl), 5-(iodoacetamida)fluoroscein (5-IAF), fluoroscein 5-isothiocyanate (FITC), tetramethylrhodamine 5- (and 6-)isothiocyanate (TRITC), 6-acryloyl-2-dimethylaminonaphthalene (acrylodan), 7-nitrobenzo-2-oxa-1,3-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids (e.g., 1-anilinonaphthalene-8-sulfonic acid (ANS), 6-(p-toluidinyl)naphthalen-e-2-sulfonic acid (TNS), and the like), Anthroyl fatty acid, DPH, Parinaric acid, TMA-DPH, Fluorenyl fatty acid, fluorescein-phosphatidylethanolamine, Texas Red-phosphatidylethanolamine, Pyrenyl-phophatidylcholine, Fluorenyl-phosphotidylcholine, Merocyanine 540, 1-(3-sulfonatopropyl)-4-[β-[2[(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, IRDye® 700DX, IRDye® 700, IRDye® 800RS, IRDye® 800CW, IRDye® 800, Cy5, Cy5.5, Cy7, DY 676, DY680, DY682, DY780, and mixtures thereof. Additional suitable fluorophores include enzyme-cofactors; lanthanide, green fluorescent protein, yellow fluorescent protein, red fluorescent protein, or mutants and derivatives thereof.

Typically, the fluorescent group is a fluorophore selected from the category of dyes comprising polymethines, pthalocyanines, cyanines, xanthenes, fluorenes, rhodamines, coumarins, fluoresceins and BODIPY™.

In certain embodiments, the fluorescent group is a near-infrared (NIR) fluorophore that emits in the range of between about 650 to about 900 nm. Use of near infrared fluorescence technology is advantageous in biological assays as it substantially eliminates or reduces background from auto fluorescence of biosubstrates. Another benefit to the near-IR fluorescent technology is that the scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components. Within aspects of this embodiment, the fluorescent group is preferably selected form the group consisting of IRDye® 700DX, IRDye® 700, IRDye® 800RS, IRDye® 800CW, IRDye® 800, Alexa Fluor® 660, Alexa Fluor® 680, Alexa Fluor® 700, Alexa Fluor® 750, Alexa Fluor® 790, Cy5, Cy5.5, Cy7, DY 676, DY680, DY682, and DY780. In certain embodiments, the near infrared group is IRDye® 800CW, IRDye® 800, IRDye® 700DX, IRDye® 700, or Dynomic DY676.

Fluorescent labeling can be accomplished using a chemically reactive derivative of a fluorophore. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide, many of which are commercially available. Reaction of any of these reactive dyes with a biologic results in a stable covalent bond formed between a fluorophore and a biologic.

In certain instances, following a fluorescent labeling reaction, it is often necessary to remove any non-reacted fluorophore from the labeled target molecule. This is often accomplished by size exclusion chromatography, taking advantage of the size difference between fluorophore and labeled protein.

Reactive fluorescent dyes are available from many sources. They can be obtained with different reactive groups for attachment to various functional groups within the target molecule. They are also available in labeling kits that contain all the components to carry out a labeling reaction. In certain instances, Alexa Fluor® 488 NHS ester is used from Life Technologies (Cat. No. A-10235).

IV. Indirect Homogeneous Mobility Shift Assays

The present invention provides novel indirect assays for detecting and measuring the presence or level of a biologic ("drug") in a sample using size exclusion chromatography. The assays of the present invention are particularly advantageous for detecting the presence or level of drugs that target complex or large antigens including cell surface proteins, transmembrane proteins, heavily glycosylated proteins, and multimeric proteins, as well as antigens that cannot be purified, impure antigens, and partially or substantially purified antigens. The antigens are not labeled and thus patient drug/antigen complexes do not appear in the chromatogram. The principle behind the indirect assays is that the amount of patient drug determines how much unlabeled antigen remains free to bind to a labeled version of the drug. By tracking changes in the area of the free (unbound) labeled drug, one can determine how much patient drug is present.

In certain aspects, the first step of the indirect assays described herein comprises incubating a sample (e.g., serum) containing therapeutic drug (e.g., vedolizumab (VDZ)) with a fixed amount of antigen to the drug (e.g., soluble α4β7). In the second step, a fixed amount of labeled drug (e.g., VDZ coupled with Alexa Fluor® 488) is added. The amount of therapeutic drug in the sample determines how much antigen remains free and available to bind the labeled drug. This, in turn, determines how much labeled drug is free. Since the peak area of the free labeled drug is proportional to the amount of therapeutic drug in the sample, one can quantify the amount of therapeutic drug by interpolation against a standard curve containing known amounts of drug.

Figure 1:
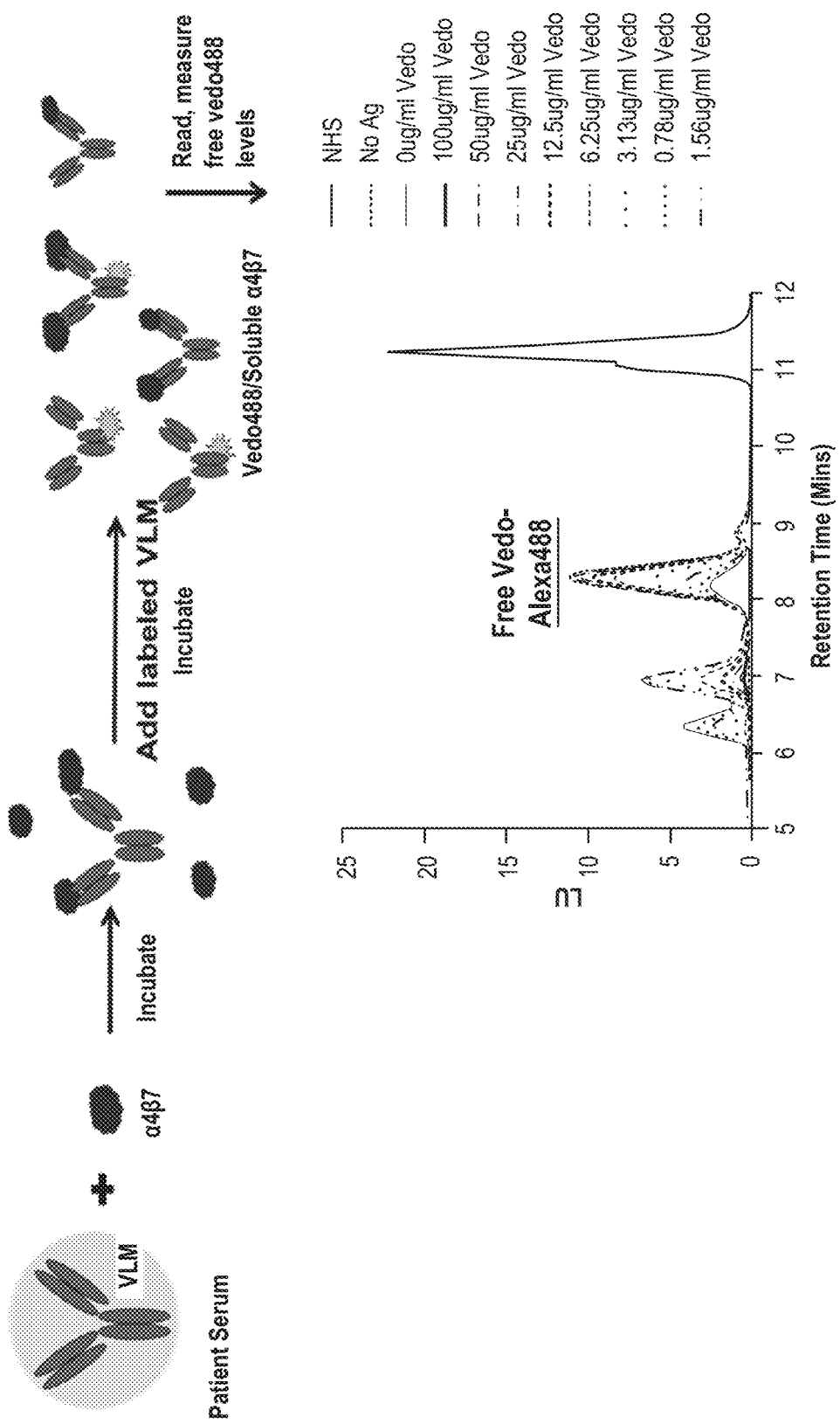
FIG. 1 shows the principle of the indirect homogeneous mobility shift assays (HMSA) of the present invention.

The following description of the principles of the indirect assays of the invention uses vedolizumab (VDZ) as the therapeutic drug for illustrative purposes only (see, FIG. 1), and is not intended to limit the scope of the assay methodology for detecting or measuring the presence or level of other biologics in patient samples:

1. To each patient sample (e.g., serum), fixed amounts of antigen (e.g., soluble α4β7) and labeled VDZ are added. The amount of antigen and labeled VDZ can be added to each sample in a controlled ratio. For example, adding an amount of antigen which would bind up about 75-80% of the labeled VDZ provides optimal sensitivity without limiting the dynamic range of the assay. The ratio of antigen to labeled VDZ was determined by titrating the antigen with a fixed amount of labeled VDZ so that when the antigen is added to the labeled VDZ, the peak of free labeled VDZ is reduced by about 75-80% (see, FIG. 2).
2. Quantification can be performed by tracking the increase of the labeled VDZ peak area ($R_t$=7.5-8.5 min). This area is proportional to the amount of therapeutic drug present. Tris-blocked Alexa488 can be added to labeled VDZ stock solutions as a loading control. Raw chromatograms can be collected in Agilent ChemStation and then exported to the program "R" for automated analysis. The standard curve can be generated by plotting the labeled VDZ peak area as a function of the log of known VDZ sample concentrations. A 10-point standard curve can be used and fitted with a 5-parameter logistic (5-PL) model to account for asymmetry. Unknowns can be determined from the standard curve by interpolation.

In certain embodiments, the ratio of antigen to labeled drug that is added to a sample is an amount of each reagent that provides the best compromise between the low-end sensitivity needed as well as a dynamic range that enables the measurement of drug in patient samples without requiring dilutions. As a non-limiting example, the ratio of antigen to labeled drug that is added to a sample is an amount of antigen that binds up about 75% to about 80% (e.g., about 75%, 76%, 77%, 78%, 79%, or 80%) of the labeled drug. In some instances, the ratio of antigen to labeled drug that is added to a sample is an amount of antigen that binds up at least about 50%, 55%, 60%, 65%, 70%, 75%, 80%, 85%, 90%, or 95% of the labeled drug. In other instances, the ratio of antigen to labeled drug that is added to a sample is an amount of antigen that binds up about 50% to about 90%, about 60% to about 90%, about 70% to about 90%, about 80% to about 90%, about 50% to about 80%, about 60% to about 80%, about 70% to about 80%, about 50% to about 70%, about 60% to about 70%, or about 50% to about 60% of the labeled drug. The ratio of antigen to labeled drug can be determined by titrating the antigen with a fixed amount of labeled drug so that when the antigen is added to the labeled drug, the peak of free labeled drug is reduced by a desired percent (e.g., about 75-80%).

In certain other embodiments, the dynamic range of the indirect assays described herein can be improved by proportionately increasing the amount of both antigen and labeled drug that is added to a sample. In some instances, the amount of both antigen and labeled drug can be about 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold more than a reference amount of antigen and labeled drug. As a non-limiting example, the reference amount of labeled VDZ can be about 75 ng and the increased amount of labeled VDZ can be about 120 ng (i.e., 1.6-fold more than the reference amount).

In some embodiments, the lower limit of quantitation (LLOQ) of the indirect assays described herein is about 0.125 µg/mL, 0.25 µg/mL, 0.375 µg/mL, 0.5 µg/mL, 0.625 µg/mL, 0.75 µg/mL, 0.875 µg/mL, 1 µg/mL, 1.25 µg/mL, 1.5 µg/mL, 1.75 µg/mL, 2 µg/mL, 3 µg/mL, 4 µg/mL, or 5 µg/mL. In other embodiments, the upper limit of quantitation (ULOID) of the indirect assays described herein is about 8 µg/mL, 9 µg/mL, 10 µg/mL, 11 µg/mL, 12 µg/mL, 13 µg/mL, 14 µg/mL, 15 µg/mL, 16 µg/mL, 17 µg/mL, 18 µg/mL, 19 µg/mL, 20 µg/mL, 21 µg/mL, 22 µg/mL, 23 µg/mL, 24 µg/mL, 25 µg/mL, 26 µg/mL, 27 µg/mL, 28 µg/mL, 29 µg/mL, 30 µg/mL, 35 µg/mL, 40 µg/mL, 45 µg/mL, or 50 µg/mL. In particular embodiments, the LLOQ is about 1 µg/mL and the ULOQ is about 25 µg/mL.

V. Soluble α4β7 Integrin Polypeptide Antigens

In one aspect, the present invention provides an isolated soluble α4 integrin polypeptide comprising an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO: 1. In some embodiments, the isolated soluble α4 integrin polypeptide comprises β-propeller repeats (i.e., repeats 1-7) and a thigh domain of the human α4 integrin extracellular domain (see, FIG. 13; "α4Δ620"), or a fragment thereof. In other embodiments, the isolated soluble α4 integrin polypeptide comprises β-propeller repeats, a thigh domain, and one or both Calf domains (i.e., Calf-1 and/or Calf-2) of the human α4 integrin extracellular domain, or a fragment thereof. In yet other embodiments, the isolated soluble α4 integrin polypeptide is a truncated receptor comprising the entire human α4 integrin extracellular domain. The isolated soluble α4 integrin polypeptide described herein includes a ligand binding domain or a portion thereof.

In some embodiments, the isolated soluble α4 integrin polypeptide also includes an ACID peptide. Such a peptide may have an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:8. An ACID peptide can form an α-helical coiled-coil conformation with a BASE peptide. In some embodiments, the ACID peptide includes a cysteine residue that can form a disulfide bridge with a cysteine residue on the BASE peptide. Acid coiled-coil region peptides (ACID peptides) and basic coiled-coil region peptides (BASE peptides) are described in, e.g., O'Shea et al., Curr Biol, 1993, 3:658-667, Jun et al., Proc Natl Acad Sci U.S.A., 2001, 98(12):6830-6835, Takagi et al., Nat Struct. Biol., 2001, 8:412-416, Nishida et al., Immunity, 2006, 25:583-594, and Dong et al., Biochemistry, 2012, 51(44):8814-8828.

In some embodiments, the isolated soluble α4 integrin polypeptide includes a linker, such as one or more amino acid residues, e.g., 1, 2, 3, 4, 5, 6, 7, 8, 9, 10 or more amino acid residues. The linker can be located between the end of extracellular domain and the ACID peptide.

In some embodiments, the isolated soluble α4 integrin polypeptide comprises an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:3.

The soluble α4 integrin polypeptide can also include an affinity tag or epitope tag, such as a histidine tag, avidin tag, V5 tag, FLAG tag, HA tag, Myc tag, cleavable tag, and the like. In some instances, the soluble α4 integrin polypeptide can include a fluorescent tag, such as GFP, DsRed, CFP, YFP, RFP, and the like, or other detectable tag, such as horseradish peroxidase, chloramphenicol acetyltransferase, beta-galactosidase, luciferase, and the like.

In another aspect, the present invention provides an isolated soluble β7 integrin polypeptide comprising an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:2. In some embodiments, the isolated soluble β7 integrin polypeptide comprises a PSI domain, an I-like domain, hybrid domains, and an I-EGF 1 domain of the human β7 integrin extracellular domain (see, FIG. 13; "β7Δ527"), or a fragment thereof. In other embodiments, the isolated soluble β7 integrin polypeptide comprises one or more of the PSI domain, I-like domain, and one or both hybrid domains of the human β7 integrin extracellular domain, or a fragment thereof. In yet other embodiments, the isolated soluble β7 integrin polypeptide comprises a PSI domain, an I-like domain, hybrid domains, I-EGF domains (i.e., domains 1-4), and optionally a β-tail of the human β7 integrin extracellular domain, or a fragment thereof. In further embodiments, the isolated soluble β7 integrin polypeptide is a truncated receptor comprising the entire human β7 integrin extracellular domain. The soluble β7 integrin polypeptide described herein includes a ligand binding domain or a portion thereof.

In some embodiments, the isolated soluble β7 integrin polypeptide also includes a BASE peptide. Such a peptide may have an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:9. A BASE peptide can form an α-helical coiled-coil conformation with an ACID peptide.

In some embodiments, the isolated soluble β7 integrin polypeptide includes a protease cleavage site. In some instances, the cleavage site is a tobacco etch virus (TEV) protease cleavage site. The TEV site can include the amino acid sequence EXXYXQ/S, wherein X is any amino acid residue (SEQ ID NO:10). The TEV site may be located upstream the BASE peptide.

In some embodiments, the isolated soluble β7 integrin polypeptide includes a linker, such as one or more amino acid residues, e.g., 1, 2, 3, 4, 5, 6, 7, 8, 9, 10 or more amino acid residue. The linker can be located between the end of the EGF-I domain of the β7 integrin extracellular domain and the cleavage site.

In some embodiments, the isolated soluble β7 integrin polypeptide further comprises an affinity tag or epitope tag. Useful affinity or epitope tags include, but are not limited to, a histidine tag, avidin tag, V5 tag, FLAG tag, HA tag, Myc tag, cleavable tag, and the like. In some instances, the soluble β7 integrin polypeptide can include a fluorescent tag, such as GFP, DsRed, CFP, YFP, RFP, and the like, or other detectable tag, such as horseradish peroxidase, chloramphenicol acetyltransferase, beta-galactosidase, luciferase, and the like.

In some embodiments, the isolated soluble β7 integrin polypeptide comprises an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:4.

The isolated soluble β7 integrin polypeptide can associate with a soluble α4 integrin polypeptide described herein to form a complex, such as a covalently linked heterodimer. In some instances, the α4β7 integrin complex can bind to α4β7 ligands, such as but not limited to VCAM-1 and MAdCAM-1, and to antibodies directed against α4β7 integrin, such as, but not limited to, vedolizumab, natalizumab, and etrolizumab.

In some aspects, the present invention provides an isolated soluble α4β7 integrin polypeptide comprising a soluble α4 integrin polypeptide having an amino acid sequence that has at least 80% identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO: 1, wherein the α4 integrin polypeptide is linked to a first member of a binding pair, and a soluble β7 integrin polypeptide having an amino acid sequence that has at least 80% identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO: 2, wherein the (37 integrin polypeptide is linked to a second member of the binding pair.

In some embodiments, the binding pair can be any peptides, molecules, motifs, and compounds that can allow the α4 subunit and β7 subunit to form a heterodimer, such as a covalently linked heterodimer. The α4β7 heterodimer is capable of binding to α4β7 ligands, such as, but not limited to VCAM-1 and MAdCAM-1, and to antibodies directed against α4β7 integrin, such as, but not limited to, vedolizumab, natalizumab, and etrolizumab. The soluble α4 integrin polypeptide and the soluble β7 integrin polypeptide can heterodimerize via a cysteine bridge or a derivative thereof (see, FIG. 13). In some embodiments, the binding pair is selected from the group consisting of coiled-coil peptides, leucine zipper peptides, dock-and-lock peptides, avidin-biotin, and derivatives thereof. In some instances, the coiled-coil peptides are ACID-BASE peptides.

The polypeptides described herein can be produced by any method known to one of ordinary skill in the art, such as but not limited to, synthetic methods, such as solid phase and liquid phase synthesis, or recombinant biology methods, such as those described herein.

In other aspects, the present invention provides an expression vector encoding a soluble α4β7 integrin polypeptide comprising a first polynucleotide sequence comprising a nucleic acid sequence encoding a soluble α4 integrin polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:1 and a nucleic acid sequence encoding a first member of a binding pair, and a second polynucleotide sequence comprising a nucleic acid sequence encoding a soluble (37 integrin polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:2 and a nucleic acid sequence encoding a second member of the binding pair. In some embodiments, the first member of the binding pair is an ACID peptide. In some embodiments, the first member of the binding pair is a BASE peptide. In some instances, the second polynucleotide sequence further comprises a nucleic acid sequence encoding an affinity tag, such as a histidine tag. In some instances, the second polynucleotide sequence further comprises a nucleic acid sequence encoding a protease cleavage site, such as a TEV site.

In some embodiments, the first polynucleotide sequence comprises a nucleic acid sequence encoding a polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:3. In some embodiments, the second polynucleotide sequence comprises a nucleic acid sequence encoding a polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:4.

In some embodiments, the expression vector is capable of directing expression of the polynucleotide sequences preferentially in a particular cell type. The expression vector can be a plasmid, phage, phagemid, cosmid, bacteriophage, baculovirus vector, lentiviral vector, retroviral vector, adenoviral vector, yeast plasmid, and the like. The expression vector can also comprise a promoter. Useful promoters include constitutive promoters and inducible promoters. The first polynucleotide sequence and/or the second polynucleotide sequence of the expression vector may be operably linked to a promoter. The promoter can be selected depending on the host cell containing the expression vector or used to generate or produce the soluble α4β7 integrin polypeptide encoded by the expression vector described herein. The expression vector may include regulatory elements, a selectable marker cassette, antibiotic resistance cassette, or any other component that facilitates the expression of the polypeptide by a host cell.

In some embodiments, the first and second polynucleotide sequences are found in a single expression vector. Such polynucleotide sequence can be located in a bicistronic expression vector such that an IRES sequence is located between the first and second polynucleotides sequences in the vector. A single promoter can drive the expression of both polynucleotides sequences. In some embodiments, the first polynucleotide sequence is operably linked to the promoter and is located immediately upstream from a nucleic acid sequence encoding a ribosomal skip, such as a viral 2A peptide, which is immediately upstream of the second polynucleotide sequence. In other embodiments, the second polynucleotide sequence is operably linked to the promoter and is located immediately upstream from a nucleic acid sequence encoding a ribosomal skip which is immediately upstream of the first polynucleotide sequence. The soluble α4 integrin polypeptide and soluble β7 integrin polypeptide can be generated from one expression vector.

Methods for constructing an expression vector are known to those of ordinary skill in the art. Detailed descriptions of protocols and methods are described in, e.g., Green, M. R., and Sambrook, J., eds., Molecular Cloning: A Laboratory Manual, 4th ed., Cold Spring Harbor Laboratory Press, Cold Spring Harbor, N.Y. (2012), Ausubel, F. M., et al., Current Protocols in Molecular Biology (Supplement 99), John Wiley & Sons, New York (2012); Berger and Kimmel, Guide to Molecular Cloning Techniques, Methods in Enzymology: Volume 152, Academic Press, Inc., San Diego, CA, (1987); and PCR Protocols: A Guide to Methods and Applications, Academic Press, San Diego, CA, (1990).

In other aspects, the present invention provides a host cell comprising any one of the expression vectors encoding a soluble α4β7 integrin polypeptide described herein. The host cell can be a stable cell line, such as, but not limited to, HEK293 cells, CHO cells, COS cells, Jurkat cells, NIH3T3 cells, and derivatives thereof. The host cell can be a bacterial cell, yeast cell, fungal cell, algal cell, plant cell, insect cell, animal cell, mammalian cell, non-human cell, or human cell. Suitable host cells are described in Goeddel, Gene Expression Technology: Methods in Enzymology, 185, Academic Press, San Diego, CA, (1990).

The expression vector can be introduced into the host cell by methods including, but not limited to, transformation, transfection, lipofection, nucleofection, microinjection, electroporation, biolistics, virosomes, liposomes, immunoliposomes, polycation or lipid:polynucleotide conjugates, naked DNA, artificial virions, and agent-enhanced uptake of DNA.

In yet another aspect, the present invention provides a method of generating a soluble α4β7 integrin polypeptide encoded by any one of the expression vectors described herein. The method comprises (a) introducing the expression vector encoding the soluble α4β7 integrin polypeptide into a host cell, (b) culturing the resulting host cell under conditions to produce the soluble α4β7 integrin polypeptide, and (c) isolating the soluble α4β7 integrin polypeptide.

The cells containing the expression vector can be cultured under conditions that allow, promote or induce the production of the soluble α4β7 integrin polypeptide.

The soluble α4 integrin polypeptide, soluble β7 integrin polypeptide and soluble α4β7 integrin polypeptide can be purified from, for example, a cell culture supernatant or soluble fraction of a cell extract, according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. C. Janson and Lars Ryden, eds., VCH Publishers, New York, (1989)) to obtain substantially pure polypeptides. Methods for protein purification, chromatography, electrophoresis, centrifugation, and crystallization are described in, e.g., Coligan et al., Current Protocols in Protein Science, Vol. 1, John Wiley and Sons, Inc., New York, (2000).

The soluble recombinant α4β7 integrin polypeptide can complex with its cognate ligand, such as a ligand that specifically binds to wild-type, full-length α4β7 integrin. The soluble recombinant α4β7 integrin polypeptide can be an antigen for an anti-α4β7 integrin antibody.

VI. Soluble IL-12p40 Polypeptide Antigens

In one aspect, the present invention provides an isolated soluble IL-12p40 polypeptide comprising an amino acid sequence having at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NOS:6, 11, 12, or 13. In some embodiments, the polypeptide further comprises an affinity tag. In other embodiments, the isolated soluble IL-12p40 polypeptide comprising an amino acid sequence having at least 80% sequence identity, e.g., at least 80%, 81%, 82%, 83%, 84%, 85%, 86%, 8'7%, 88%, 89%, 90%, 91%, 92%, 93%, 94%, 95%, 96%, 97%, 98%, 99% or 100% sequence identity, to SEQ ID NO:7. In some embodiments, the polypeptide further comprises an affinity tag. In particular embodiments, the soluble IL-12p40 polypeptide is a monomer, and cannot dimerize or form multimers.

In another aspect, the present invention provides an expression vector encoding a soluble IL-12p40 polypeptide comprising a polynucleotide sequence comprising a nucleic acid sequence encoding an IL-12p40 polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NOS:6, 11, 12, or 13. The polynucleotide sequence can further comprise a nucleic acid sequence encoding an affinity tag. Such an affinity tag can be a histidine tag, such as hexahistidine. Other non-limiting examples of affinity tags include an avidin tag, V5 tag, FLAG tag, HA tag, Myc tag, cleavable tag, and the like. In some embodiments, the polynucleotide comprising a nucleic acid sequence encoding an IL-12p40 polypeptide having an amino acid sequence that has at least 80% sequence identity, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity, to SEQ ID NO:7.

In some embodiments, the expression vector is capable of directing expression of the polynucleotide sequences preferentially in a particular cell type. The expression vector can be a plasmid, phage, phagemid, cosmid, bacteriophage, baculovirus vector, lentiviral vector, retroviral vector, adenoviral vector, yeast plasmid, and the like. The expression vector can also comprise a promoter. Useful promoters include constitutive promoters and inducible promoters. The polynucleotide sequence of the expression vector may be operably linked to a promoter. The promoter can be selected depending on the host cell selected to generate or produce the soluble IL-12p40 polypeptide encoded by the expression vector described herein. The expression vector may include regulatory elements, a selectable marker cassette, antibiotic resistance cassette, or any other component that facilitates the expression of the polypeptide.

Methods for constructing an expression vector are known to those of ordinary skill in the art. Detailed descriptions of protocols and methods are described in, e.g., Green, M. R., and Sambrook, J., eds., Molecular Cloning: A Laboratory Manual, 4th ed., Cold Spring Harbor Laboratory Press, Cold Spring Harbor, N.Y. (2012); Ausubel, F. M., et al., Current Protocols in Molecular Biology (Supplement 99), John Wiley & Sons, New York (2012); Berger and Kimmel, Guide to Molecular Cloning Techniques, Methods in Enzymology, Volume 152, Academic Press, Inc., San Diego, CA (1987); and PCR Protocols: A Guide to Methods and Applications, Academic Press, San Diego, CA, (1990).

In other aspects, the present invention provides a host cell comprising any one of the expression vectors encoding a soluble IL-12p40 polypeptide described herein. The host cell can be a stable cell line, such as, but not limited to, HEK293 cells, CHO cells, COS cells, Jurkat cells, NIH3T3 cells, and derivatives thereof. The host cell can be a bacterial cell, yeast cell, fungal cell, algal cell, plant cell, insect cell, animal cell, mammalian cell, non-human cell, or human cell. Suitable host cells are described in Goeddel, Gene Expression Technology: Methods in Enzymology 185, Academic Press, San Diego, CA, 1990.

The expression vector can be introduced into the host cell by methods including, but not limited to, transformation, transfection, lipofection, nucleofection, microinjection, electroporation, biolistics, virosomes, liposomes, immunoliposomes, polycation or lipid:polynucleotide conjugates, naked DNA, artificial virions, and agent-enhanced uptake of DNA.

In yet another aspect, the present invention provides method of generating a soluble IL-12p40 polypeptide encoded by any one of the expression vectors described herein. The method comprises (a) introducing the expression vector encoding the soluble IL-12p40 polypeptide into a host cell, (b) culturing the resulting host cell under conditions to produce the soluble IL-12p40 polypeptide, and (c) isolating the soluble IL-12p40 polypeptide.

The cells containing the expression vector can be cultured under conditions that allow, promote or induce the production of the soluble IL-12p40 polypeptide.

The soluble IL-12p40 polypeptide can be purified from, for example, a cell culture supernatant or soluble fraction of a cell extract, according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. C. Janson and Lars Ryden, eds., VCH Publishers, New York, (1989)) to obtain substantially pure polypeptides. Methods for protein purification, chromatography, electrophoresis, centrifugation, and crystallization are described in, e.g., Coligan et al., Current Protocols in Protein Science, Vol. 1, John Wiley and Sons, Inc., New York, (2000).

Unlike wild-type IL-12p40, the soluble recombinant IL-12p40 polypeptide described herein cannot form a dimer, trimer, or oligomer. In particular embodiments, the presence of either two cysteine to alanine substitutions (SEQ ID NO:6) or two cysteine to serine substitutions (SEQ ID NO:11) in the wild-type IL-12p40 polypeptide sequence prevents the IL-12p40 antigen from oligomerizing. In other embodiments, the soluble IL-12p40 polypeptide monomer has the wild-type IL-12p40 polypeptide sequence with one cysteine to alanine substitution and one cysteine to alanine substitution (SEQ ID NOS:12 or 13). An anti-IL-12p40 antibody, such as ustekinumab, can specifically bind to the soluble recombinant IL-12p40 polypeptide.

VII. Biologic Therapy

The indirect homogeneous mobility shift assays of the present invention are suitable for detecting and/or measuring the presence or level of a biologic in a sample from a subject (e.g., a subject receiving biologic therapy). Non-limiting examples of biologics include antibodies, antibody fragments, proteins, polypeptides, peptides, fusion proteins (e.g., Ig fusion proteins or Fc fusion proteins), multivalent binding proteins (e.g., DVD Ig), antibody-drug conjugates, vaccines, nucleic acids, sugars, recombinant forms thereof, engineered forms thereof, and combinations thereof.

Examples of antibody-based biologics include, but are not limited to, diagnostic or therapeutic monoclonal antibodies and antigen-binding fragments or conjugates thereof. In certain embodiments, the antibody comprises an anti-integrin drug such as an anti-α4β7 integrin drug (e.g., vedolizumab (ENTYVIO™), etrolizumab) and/or an anti-α4β1 integrin drug (e.g., natalizumab (TYSABRI®)). In other embodiments, the antibody comprises an anti-cytokine drug such as an anti-IL12p40 drug (e.g., ustekinumab))(STELARA®)). In yet other embodiments, the antibody comprises an anti-cytokine receptor drug such as an anti-IL-6 receptor drug (e.g., tocilizumab (ACTEMRA®)). In further embodiments, the antibody comprises an anti-CD receptor drug such as an anti-CD3 receptor drug (e.g., visilizumab), an anti-CD4 receptor drug (e.g., priliximab), an anti-CD20 receptor drug (e.g., rituximab (RITUXAN®), ofatumumab (ARZERRA®), obinutuzumab (GAZYVA®), ibritumomab tiuxetan (ZEVALIN®), tositumomab (BEXXAR®), ocrelizumab, veltuzumab, an anti-CD25 receptor drug (e.g., daclizumab (ZENAPAX®)), or combinations thereof. In other embodiments, the antibody comprises an anti-TNFα drug such as infliximab (REMICADE®), adalimumab (HUMIRA®), etanercept (ENBREL®), golimumab (SIMPONI®), certolizumab pegol (CIMZIA®), or combinations thereof. Additional examples of antibody-based biologics include antibody-drug conjugates such as brentuximab vedotin (ADCETRIS®).

Table 1 provides an exemplary and non-exhaustive list of diagnostic and therapeutic monoclonal antibodies which have either been approved or are currently in development. An extensive list of biologic medicines including monoclonal antibody-based therapeutics and diagnostics in clinical development and approved products is provided in the 2006 PhRMA Report entitled "418 Biotechnology Medicines in Testing Promise to Bolster the Arsenal Against Disease" and the 2013 PhRMA Report entitled "Medicines in Development—Biologics," the disclosures of which are hereby incorporated by reference in their entirety for all purposes.

TABLE 1

Monoclonal Antibodies (mAb)

| Product Name | Company | Indication |
|---|---|---|
| Digestive Disorders | | |
| ABT 874 | Abbott Laboratories | Crohn's disease |
| AMG 139/MEDI-2070 | Amgen | Crohn's disease |
| AMG 181/MEDI-7183 | Amgen | Crohn's disease, ulcerative colitis |
| anrukinzumab (IMA-638) | Pfizer | ulcerative colitis |
| anti-IP10 | Bristol-Myers Squibb | Crohn's disease, ulcerative colitis |
| clazakizumab (anti-IL6) | Bristol-Myers Squibb, Alder Biopharmaceuticals | Crohn's disease |
| etrolizumab (rhuMAb-07) | Genentech | ulcerative colitis |
| GSK1070806 (IL-18 mAb) | GlaxoSmithKline | inflammatory bowel disease |
| Humira ® (adalimumab) | AbbVie | Crohn's disease |
| MDX-1100 | Millennium Pharmaceuticals | ulcerative colitis |
| Nuvion ® (visilizumab) | PDL BioPharma | I.V. steroid-refractory ulcerative colitis and Crohn's disease |
| PF-00547659 | Pfizer | Crohn's disease |
| PF-04236921 | Pfizer | Crohn's disease |
| QAX576 | Novartis Pharmaceuticals | Crohn's disease |
| Remicade ® (infliximab) | Janssen Biotech | Crohn's disease |
| SAR252067 (anti-LIGHT mAb) | Sanofi US | Crohn's disease, ulcerative colitis |
| SAR339658 (VLA2 antagonist) | Sanofi US | inflammatory bowel disease |
| Simponi ® (golimumab) | Janssen Biotech | ulcerative colitis |
| Stelara ® (ustekinumab) | Janssen Biotech | Crohn's disease |
| tralokinumab | AstraZeneca, MedImmune | ulcerative colitis |
| Tysabri ® (natalizumab) | Biogen Idec | Crohn's disease |
| vedolizumab (MLN0002) | Takeda Pharmaceuticals | Crohn's disease, ulcerative colitis |
| Autoimmune disorders | | |
| ABT-122 | AbbVie | rheumatoid arthritis |
| Actemra ® (tocilizumab) | Genentech, Roche | early rheumatoid arthritis, systemic sclerosis |
| AGS-009 | Argos Therapeutics | systemic lupus erythematosus (SLE) |
| alemtuzumab | Genzyme | relapsing-remitting multiple sclerosis |
| AME 527 | Applied Molecular | rheumatoid arthritis |
| AMG 108 | Amgen | rheumatoid arthritis |
| AMG 557/MEDI-5872 | Amgen, AstraZeneca, MedImmune | SLE |
| AMG 714 | Amgen | rheumatoid arthritis |
| AMG 729 | Amgen | autoimmune diseases |
| AMG 811 | Amgen | discoid lupus erythematosus, SLE |
| ART 874 | Abbott Laboratories | multiple sclerosis |

TABLE 1-continued

Monoclonal Antibodies (mAb)

| Product Name | Company | Indication |
|---|---|---|
| anti-CD16 mAb | MacroGenics | immune thrombocytopenic |
| anti-IL17 mAb (RG7624) | Genentech | autoimmune disorders |
| anti-LINGO (BIIB033) | Biogen Idec | Multiple sclerosis |
| Benlysta ® (belimumab) | GlaxoSmithKline | rheumatoid arthritis, SLE, systemic scleroderma |
| BI-695500 (rituximab biosimilar) | Boehringer-Ingelheim Pharmaceuticals | rheumatoid arthritis |
| BI-695501 (adalimumab biosimilar) | Boehringer-Ingelheim Pharmaceuticals | rheumatoid arthritis |
| BT-061 | AbbVie, Biotest | rheumatoid arthritis |
| Cimzia ® (certolizumab pegol) | UCB | ankylosing spondylitis, juvenile rheumatoid arthritis |
| clazakizumab (anti-IL6) | Bristol-Myers Squibb, Alder Biopharmaceuticals | rheumatoid arthritis |
| CNTO-136 (sirukumab) | Janssen Biotech | rheumatoid arthritis |
| CNTO-1959 | Janssen Biotech | rheumatoid arthritis |
| daclizumab (anti-CD25 mAb) | AbbVie, Biogen Idec | multiple sclerosis |
| epratuzumab | Immunomedics, UCB | SLE |
| ETI-201 | Elusys Therapeutics | SLE |
| GSK1223249 (NOGO-A mAb) | GlaxoSmithKline | multiple sclerosis |
| Humira ® (adalimumab) | AbbVie | rheumatoid arthritis, ankylosing spondylitis, juvenile rheumatoid arthritis, psoriasis |
| HuZAF ® (fontolizumab) | PDL BioPharma, Biogen Idec | rheumatoid arthritis |
| Ilaris ® (canakinumab) | Novartis Pharmaceuticals | systemic juvenile idiopathic arthritis |
| IMMU-106 (hCD20) | Immunomedics | autoimmune diseases |
| mavrilimumab | AstraZeneca, MedImmune | rheumatoid arthritis |
| MEDI-545 (MDX-1103) | Medarex, MedImmune | lupus |
| MEDI-546 (anti-IFN-alphaR mAb) | AstraZeneca, MedImmune | SLE |
| MEDI-551 (anti-CD19 mAb) | AstraZeneca, MedImmune | scleroderma |
| MEDI-570 (anti-ICOS mAb) | AstraZeneca, MedImmune | SLE |
| MLN 1202 | Millennium Pharmaceuticals | multiple sclerosis |
| NN8209 (anti-C5aR-151 mAb) | Novo Nordisk | rheumatoid arthritis |
| NN8210 (anti-C5aR-215 mAb) | Novo Nordisk | rheumatoid arthritis |
| NN8226 (anti-IL-20 mAb) | Novo Nordisk | rheumatoid arthritis |
| NN8765 (anti-NKG2 mAb) | Novo Nordisk | rheumatoid arthritis |
| NN8828 (anti-IL-21 mAb) | Novo Nordisk | rheumatoid arthritis |
| ocrelizumab (anti-CD20 mAb) | Biogen Idec, Genentech, Roche | multiple sclerosis, rheumatoid arthritis |
| ofatumumab | GlaxoSmithKline | multiple sclerosis, rheumatoid arthritis |
| OKT3-gamma-1 | Johnson & Johnson | psoriatic arthritis |
| olokizumab | UCB | rheumatoid arthritis |
| otelixizumab (anti-CD3 mAb) | GlaxoSmithKline | rheumatoid arthritis |
| ozoralizumab (ATN-103) | Ablynx | rheumatoid arthritis |
| pateclizumab (anti-LT alpha mAb) | Genentech | rheumatoid arthritis |
| PD-360324 | Pfizer | cutaneous lupus erythematosus |
| PF-04236921 | Pfizer | SLE, rheumatoid arthritis |
| PF-05280586 (rituximab biosimilar) | Pfizer | rheumatoid arthritis |
| Prolia ® (denosumab) | Amgen | rheumatoid arthritis |
| Remicade ® (infliximab) | Janssen Biotech | rheumatoid arthritis |
| Rituxan ® (rituximab) | Genentech, Biogen Idec | rheumatoid arthritis, lupus, primary progressive multiple sclerosis, SLE, relapsing-remitting multiple sclerosis |
| rontalizumab (RG7415) | Genentech | SLE |
| SAN-300 (anti-VLA-1 antibody) | Santarus | rheumatoid arthritis |
| SAR113244 (anti-CXCR5 mAb) | Sanofi US | SLE |
| sarilumab (SAR153191) | Regeneron Pharmaceuticals, Sanofi US | rheumatoid arthritis |
| secukinumab (AIN457) | Novartis Pharmaceuticals | ankylosing spondylitis, rheumatoid arthritis, multiple sclerosis |
| sifalimumab (anti-IFN-alpha mAb) | AstraZeneca, MedImmune | SLE |
| Simponi ® (golimumab) | Janssen Biotech | rheumatoid arthritis, juvenile rheumatoid arthritis, sarcoidosis, ankylosing spondylitis, psoriatic arthritis |
| siplizumab (MEDI-507) | MedImmune | psoriasis |
| Soliris ® (eculizumab) | Alexion Pharmaceuticals | severe or refractory myasthenia gravis |
| Stelara ® (ustekinumab) | Janssen Biotech | rheumatoid arthritis, sarcoidosis, plaque psoriasis, multiple sclerosis |
| tabalumab (BAFF inhibitor) | Eli Lilly | SLE |
| TRX 1 (anti-CD4) | TolerRx | cutaneous lupus erythematosus |
| TRX 4 | TolerRx | psoriasis |

TABLE 1-continued

Monoclonal Antibodies (mAb)

| Product Name | Company | Indication |
|---|---|---|
| Tysarbi ® (natalizumab) | Biogen Idec | Multiple sclerosis |
| veltuzumab (IMMU-106) | Immunomedics, Takeda Pharmaceuticals USA | immune thrombocytopenic purpura, rheumatoid arthritis |
| VX15 | Teva Pharmaceuticals, Vaccinex | multiple sclerosis |
| XmAb ® 5871 (anti-CD19 mAb) | Xencor | autoimmune disorders |

Musculoskeletal Disorders/Arthritis

| Product Name | Company | Indication |
|---|---|---|
| ABT-981 | AbbVie | osteoarthritis |
| AMG 167 | Amgen | metabolic bone diseases |
| AMG 745 | Amgen | muscular atrophy |
| AMG 827 (brodalumab) | AstraZeneca, Amgen | psoriatic arthritis |
| blosozumab (LY2541546) | Eli Lilly | osteoporosis |
| BYM338 | Novartis Pharmaceuticals | sporadic inclusion body myositis, muscular atrophy |
| Cimzia ® (certolizumab pegol) | UCB | psoriatic arthritis |
| clazakizumab (anti-IL6) | Bristol-Myers Squibb, Alder Biopharmaceuticals | psoriatic arthritis |
| gevokizumab (IL-1B inhibitor mAb) | XOMA | osteoarthritis of the hand |
| Humira ® (adalimumab) | AbbVie | spondylarthritis |
| Ilaris ® (canakinumab) | Novartis Pharmaceuticals | gouty arthritis |
| ixekizumab (IL-17 antibody) | Eli Lilly | psoriatic arthritis |
| LY2495655 (anti-myostatin mAb) | Eli Lilly | disuse muscular atrophy |
| MCS110 | Novartis Pharmaceuticals | synovitis |
| Prolia ® (denosumab) | Amgen | male osteoporosis, postmenopausal osteoporosis |
| romosozumab (AMG 785) | Amgen | postmenopausal osteoporosis |
| SAR391786 (REGN1033) | Regeneron Pharmaceuticals, Sanofi US | treatment of muscle atrophy post-orthopedic surgery |
| secukinumab (AIN 457) | Novartis Pharmaceuticals | psoriatic arthritis, polymyalgia rheumatica |
| Stelara ® (ustekinumab) | Janssen Biotech | psoriatic arthritis |
| tanezumab | Pfizer | osteoarthritis |

Cancer and Related Conditions

| Product Name | Company | Indication |
|---|---|---|
| 1311-huA33 | Life Science Pharmaceuticals | colorectal cancer |
| 1D09C3 | GPC Biotech | relapsed/refractory B-cell lymphomas |
| 8H9 mAb | United Therapeutics | metastatic brain cancer |
| 212-Pb-TCMC-trastuzumab | AREVA Med | HER2-positive cancer metastasized to the abdominal region |
| AbGn-7 | AbGenomics International | solid tumors |
| ABT-806 | AbbVie | solid tumors |
| Actimab-A (M195 mAb) | Actinium Pharmaceuticals | acute myeloid leukemia (AML) |
| Adcetris ® (brentuximab vedotin) | Seattle Genetics | cutaneous T-cell lymphoma, front-line Hodgkin lymphoma, post-transplant Hodgkin lymphoma relapse prevention, non-Hodgkin lymphoma, non-lymphoma malignancies, CD30-positive hematologic malignancies |
| AGS PSCA mAb | Agensys, Merck | prostate cancer |
| ALT-836 | Altor BioScience, Genentech | cancer |
| AME-133v | MENTRIK Biotech | non-Hodgkin lymphoma |
| AMG 102 | Amgen | cancer |
| AMG 479 | Amgen | cancer |
| AMG 623 | Amgen | B-cell chronic lymphocytic leukemia (CLL) |
| AMG 655 | Amgen | cancer |
| AMG 706 | Amgen | imatinib resistant GIST, advanced thyroid cancer |
| AMG 780 | Amgen | solid tumors |
| AMG 820 | Amgen | solid tumors |
| AMG 888 (U3-1287) | Amgen | non-small-cell lung cancer (NSCLC) |
| antibody-drug conjugate (RG7600) | Genentech | ovarian cancer, pancreatic cancer |
| anti-CD22 ADC (RG7593) | Genentech, Seattle Genetics | diffuse large B-cell lymphoma, non-Hodgkin lymphoma, chronic lymphocytic leukemia (CLL) |
| anti-CD23 MAb | Biogen Idec | CLL |
| anti-CD45 mAb | Actinium Pharmaceuticals | AML |
| anti-CD79b ADC (RG7596) | Genentech, Seattle Genetics | diffuse large B-cell lymphoma, non-Hodgkin lymphoma, CLL |
| anti-CD 80 MAb | Biogen Idec | non-Hodgkin B-cell lymphoma |
| anti-CXCR4 | Bristol-Myers Squibb | hematological malignancies |
| anti-EGFL7 mAb (RG7414) | Genentech | metastatic colorectal cancer, NSCLC, solid tumors |

TABLE 1-continued

Monoclonal Antibodies (mAb)

| Product Name | Company | Indication |
|---|---|---|
| anti-FGFR3 mAb (RG7444) | Genentech | solid tumors |
| anti-HER3/EGFR DAF mAb (RG7597) | Genentech | colorectal cancer, head and neck cancer |
| anti-idiotype cancer vaccine | Viventia Biotech | malignant melanoma |
| anti-lymphotoxin beta receptor mAb | Biogen Idec | solid tumors |
| anti-PD-L1 | Bristol-Myers Squibb | cancer |
| anti-PD-L1 mAb (RG7446) | Genentech | melanoma, solid tumors |
| anti-PEM MAb | Somanta Pharmaceuticals | cancer |
| anti-STEAP1 ADC (RG7450) | Genentech, Seattle Genetics | prostate cancer |
| anti-Tac(Fv)-E38 immunotoxin | National Cancer Institute | leukemia, lymphoma |
| APN301 (hu14.18-IL2) | Apeiron Biologics | malignant melanoma, neuroblastoma in children |
| Archexin ® (RX-0201) | Rexahn Pharmaceuticals | pancreatic cancer |
| Arzerra ® (ofatumumab) | GlaxoSmithKline | CLL, diffuse large B-cell lymphoma, follicular lymphoma |
| ASG-5ME | Agensys, Seattle Genetics | pancreatic cancer, castration-resistant prostate cancer |
| ASG-22ME | Agensys, Seattle Genetics | solid tumors |
| AV-203 | AVEO Oncology | solid tumors |
| Avastin ® (bevacizumab) | Genentech, Roche | ovarian cancer, HER-2 negative-breast cancer, HER-2 positive breast cancer, high-risk carcinoid tumors, glioblastoma multiforme, metastatic ovarian cancer, NSCLC, metastatic colorectal cancer |
| AVE 9633 maytansin-loaded anti-CD33 mAb | Sanofi Aventis | AML |
| bavituximab | Peregrine Pharmaceuticals | NSCLC, pancreatic cancer, breast cancer, liver cancer, prostate cancer, rectal adenocarcinoma |
| BAX-69 | Baxter International | solid tumors |
| BAY 79-4620 | Bayer HealthCare Pharmaceuticals | solid tumors |
| BAY 94-9343 | Bayer HealthCare Pharmaceuticals | solid tumors |
| BAY 20-10112 | Amgen, Bayer HealthCare Pharmaceuticals | solid tumors |
| Bexxar ® (tositumomab) | GlaxoSmithKline | non-Hodgkin lymphoma |
| BHQ880 | Novartis Pharmaceuticals | multiple myeloma |
| BI-505 | BioInvent International | multiple myeloma |
| BI-836845 | Boehringer Ingelheim Pharmaceuticals | solid tumors |
| bivatuzumab | Boehringer Ingelheim Pharmaceuticals | cancer |
| blinatumomab | Amgen | leukemia and lymphoma |
| BrevaRex ™ | ViRexx | breast cancer, multiple myeloma |
| BT-062 (indatuximab ravtansine) | Biotest | multiple myeloma |
| BYM338 | Novartis Pharmaceuticals | cancer-related cachexia |
| Campath ® (alemtuzumab) | Berlex Laboratories, Genzyme | B-cell chronic lymphocytic leukemia, lymphoma |
| catumaxomab | Fresenius Biotech | malignant ascites, ovarian cancer |
| CAT 3888 | Cambridge Antibody Technology | hairy cell leukemia |
| CDX-011 (glembatumumab vedotin) | Celldex Therapeutics | breast cancer, malignant melanoma |
| CDX-1127 | Celldex Therapeutics | hematological malignancies, solid tumors |
| CEP-37250/KNK-2804 | Teva North America, Kyowa Hakko Kirin Pharma | adenocarcinoma |
| ch14.18 mAb | United Therapeutics | neuroblastoma |
| chimeric mAb | National Cancer Institute | neuroblastoma |
| Cixutumumab (LY3012217) | Eli Lilly, Imclone Systems | NSCLC |
| CNTO-328 (siltuximab) | Janssen Biotech | giant lymph node hyperplasia, multiple myeloma, myelodysplastic syndromes, prostate cancer, renal cancer, |
| Cotara ™ mAb TNT | Peregrine Pharmaceuticals | recurrent glioblastoma |
| CP-751871 (figitumumab) | Pfizer | adrenocortical carcinoma, non-small cell lung cancer |
| CS-1008 (tigatuzumab) | Daiichi Sankyo | pancreatic cancer, colorectal cancer, non-small cell lung cancer, ovarian cancer |

TABLE 1-continued

Monoclonal Antibodies (mAb)

| Product Name | Company | Indication |
| --- | --- | --- |
| CSF-1R mAb (IMC-CS4) | Eli Lilly | solid tumors |
| CT-011 (pidilizumab) | CureTech | AML, colorectal cancer, diffuse large B-cell lymphoma, follicular lymphoma, malignant melanoma |
| dalotuzumab (MK-0646) | Merck | breast cancer, neuroendocrine tumors, NSCLC |
| daratumumab | Janssen Biotech | multiple myeloma |
| DEDN6526A | Genentech | malignant melanoma |
| demcizumab (OMP-21M18) | GlaxoSmithKline, OncoMed Pharmaceuticals | solid tumors |
| DFRF4539A | Genentech | multiple myeloma |
| DI17E6 (anti-integrin mAb) | EMD Serono | colorectal cancer, prostate cancer |
| DKN-01 | Dekkun | solid tumors |
| ecromeximab (KW-2871) | Life Science Pharmaceuticals | metastatic melanoma |
| elotuzumab | Bristol-Myers Squibb, AbbVie | multiple myeloma |
| EMD 273063 | EMD Lexigen | solid tumors, malignant melanoma, neuroblastoma, SCLC |
| enavatuzumab | AbbVie | solid tumors |
| ensituximab (NPC-1C) | Neogenix Oncology | colorectal cancer, pancreatic cancer |
| epratuzumab Y-90/veltuzumab combination | Immunomedics | non-Hodgkin lymphoma |
| Erbitux ® (cetuximab) | Bristol-Myers Squibb, Eli Lilly, ImClone Systems | esophageal cancer, colorectal cancer, squamous cell cancer of the head and neck |
| farletuzumab (MORAb-003) | Eisai | platinum-sensitive ovarian cancer, NSCLC |
| FG-3019 | FibroGen | pancreatic cancer |
| ficlatuzumab | AVEO Oncology | glioblastoma, lymphoma, multiple myeloma, solid tumors |
| flanvotumab (TYRP1 protein) | Eli Lilly | malignant melanoma |
| Fzd7 (vantictumab) | Bayer HealthCare Pharmaceuticals, OncoMed Pharmaceuticals | solid tumors |
| ganitumab | Amgen | pancreatic cancer, breast cancer, colorectal cancer, sarcoma |
| GC-33/RG7686 | Chugai Pharma USA, Roche | liver cancer |
| GMK | Progenies Pharmaceuticals | prevention of recurrence following surgery to remove primacy melanoma in high-risk patients |
| GS-6624 (simtuzumab) | Gilead Sciences | colorectal cancer, pancreatic cancer |
| HCD122 (anti-CD40 mAb) | Novartis Pharmaceuticals, XOMA | lymphoma |
| Herceptin ® (trastuzumab) | Genentech | HER2-overexpressing early stage or metastatic breast cancer |
| HGS-ETR1 (mapatumumab) | GlaxoSmithKline | liver cancer, multiple myeloma, NSCLC, hematologic and solid tumors |
| HGS-TR2J | Human Genome Sciences | advanced solid tumors |
| HuC242-DM4 | ImmunoGen | colorectal, gastrointestinal, NSCLC, pancreatic cancers |
| HuL2G7 | Galaxy Biotech | solid tumors |
| HuMax-CD4 (zanolimumab) | Genmab, Serono | cutaneous T-cell lymphoma, non-cutaneous T-cell lymphoma |
| HuMax CD20 (ofatumumab) | Genmab | CLL, non-Hodgkin lymphoma |
| HuMax-EGFr | Genmab | head and neck cancer |
| HuM195/rGel | Targa Therapeutics | AML, CML, myelodysplastic syndromes |
| huN901-DM1 (lorvotuzumab mertansine) | ImmunoGen | SCLC, multiple myeloma, solid tumors |
| icrucumab (LY3012212) | Eli Lilly, ImClone Systems | bladder cancer, breast cancer, colorectal cancer |
| IMC-TR1 (LY3022859) | Eli Lilly, ImClone Systems | solid tumors |
| IMGN529 | ImmunoGen | non-Hodgkin lymphoma |
| IMGN853 | ImmunoGen | solid tumors |
| IMMU-102 (epratuzumab Y-90) | Immunomedics | non-Hodgkin lymphoma |
| inotuzumab ozogamicin (CMC-544) | Pfizer, UCB | aggressive non-Hodgkin lymphoma, ALL |
| Iomab-B (anti-CD45 mAb) | Actinium Pharmaceuticals | AML |
| J 591 Lu-177 | BZL Biologics | prostate cancer |
| KB004 | KaloBios Pharmaceuticals | hematological malignancies |
| LFA102 | Novartis Pharmaceuticals, XOMA | breast cancer, prostate cancer |
| lirilumab (anti-KIR) | Bristol-Myers Squibb | cancer |
| LY2495655 (anti-myostatin mAb) | Eli Lilly | cancer cachexia |
| LY2875358 (c-met mAb) | Eli Lilly | cancer |
| M195-bismuth 213 conjugate | Actinium Pharmaceuticals | AML |
| M200 (volociximab) | PDL BioPharma, Biogen Idec | advanced solid tumors |
| MAb HeFi-1 | National Cancer Institute | lymphoma, non-Hodgkin lymphoma |

TABLE 1-continued

Monoclonal Antibodies (mAb)

| Product Name | Company | Indication |
| --- | --- | --- |
| MABp1 | XBiotech | cancer-related cachexia, advanced cancer, leukemia |
| MDX-060 (iratumumab) | Medarex | Hodgkin's disease, anaplastic large-cell-lymphoma |
| MDX-070 | Medarex | prostate cancer |
| MDX-214 | Medarex | EGFR-expressing cancers |
| MEDI-522 | MedImmune | T-cell lymphoma, melanoma, prostate cancer, solid tumors |
| MEDI-551 (anti-CD19 mAb) | AstraZeneca, MedImmune | hematological malignancies |
| MEDI-573 (anti-IGF mAb) | AstraZeneca, MedImmune | solid tumors |
| MEDI-575 (anti-PDGFRα mAb) | AstraZeneca, MedImmune | glioblastoma, NSCLC |
| MEDI-0639 (anti-DLL-4 mAb) | AstraZeneca, MedImmune | solid tumors |
| MEDI-3617 (anti-ANG-2 mAb) | AstraZeneca, MedImmune | solid tumors |
| MEDI-4736 (anti-CD274 mAb) | AstraZeneca, MedImmune | cancer |
| MEDI-6469 (anti-OX40 mAb) | AgonOx, AstraZeneca, MedImmune | solid tumors |
| MGA271 (anti-B7-H3) | MacroGenics | solid tumors |
| MGAH22 (anti-HER2) | MacroGenics | solid tumors |
| milatuzumab | Immunomedics | CLL |
| milatuzumab-DOX | Immunomedics | multiple myeloma |
| MINT1526A | Genentech | solid tumors |
| MK-3475 | Merck | malignant melanoma, NSCLC |
| MLN0264 (GCC antibody drug conjugate) | Millennium Pharmaceuticals | gastrointestinal cancer |
| mogamulizimab | Kyowa Hakko Kirin Pharma | cutaneous T-cell lymphoma, adult T-cell lymphoma, T-cell leukemia |
| MORAb 003 | Eisai | ovarian cancer |
| MORAb-004 | Eisai | colorectal cancer, melanoma, sarcoma |
| MORAb-009 (amatuximab) | Eisai | mesothelioma |
| moxetumomab pasudotox | AstraZeneca, MedImmune | hematological malignancies |
| Mylotarg™ (gemtuzumab ozogamicin) | Wyeth | acute myeloid leukemia |
| necitumumab | Bristol-Myers Squibb, Eli Lilly, ImClone Systems | NSCLC |
| neuradiab | Bradmer Pharmaceuticals | glioblastoma |
| nimotuzumab | InnoMab PIE | glioma, squamous cell carcinomas of the head and neck, recurrent or refractory high grade malignant glioma, anaplastic astrocytomas, glioblastomas and diffuse intrinsic pontine glioma |
| nivolumab (anti-PD1) | Bristol-Myers Squibb | melanoma, NSCLC, renal cell carcinoma, solid tumors |
| obinutuzumab (GA101) | Biogen Idec, Genentech | CLL, diffuse large B-cell lymphoma, non-Hodgkin lymphoma |
| olamtumab (LY3012207) | Eli Lilly, ImClone Systems | glioblastoma |
| OMP-52M51 (anti-Notch 1) | GlaxoSmithKline, OncoMed Pharmaceuticals | hematological malignancies |
| OMP-59R5 (anti-Notch 2/3) | GlaxoSmithKline, OncoMed Pharmaceuticals | pancreatic cancer |
| onartuzumab (anti-c-met- mAb) | Genentech | metastatic NSCLC |
| oregovomab | Quest Pharmatech | ovarian cancer |
| PAM 4 | Merck | pancreatic cancer |
| panitumumab (rHuMAb EGFr) | Abgenix | colorectal cancer |
| Perjeta™ (pertuzumab) | Genentech | early HER2-positive breast cancer, HER2-positive metastatic breast cancer, HER2-positive gastric cancer, ovarian cancer |
| PF-03446962 | Pfizer | solid tumors |
| PF-04605412 | Pfizer | solid tumors |
| PF-05082566 | Pfizer | cancer, lymphoma |
| PF-05280014 (trastuzumab biosimilar) | Pfizer | metastatic breast cancer |
| PSMA-ADC | Progenics Pharmaceuticals | prostate cancer |
| R1550 RadioTheraCIM | Roche, YM BioSciences | metastatic breast cancer, glioma |
| mmucirumab (LY3009806) | Eli Lilly, ImClone Systems | breast cancer, colorectal cancer, gastric cancer |
| RAV 12 | Raven Biotechnologies | cancer |
| Redectane ® (girentuximab I-124) | Wilex AG | diagnosis of kidney cancer |
| REGN1400 | Regeneron Pharmaceuticals | cancer |
| Rencarex ® G250 | Wilex AG | renal cancer |
| RG7116 | Roche | solid tumors |
| RG7155 | Roche | solid tumors |
| RG7160 (humAb EGFR) | Roche | colorectal cancer |
| RG7212 | Roche | solid tumors |

TABLE 1-continued

Monoclonal Antibodies (mAb)

| Product Name | Company | Indication |
| --- | --- | --- |
| RG7356 (anti-CD44 mAb) | Roche | AML, solid tumors |
| RG7458 (antibody-drug conjugate) | Genentech, Seattle Genetics | ovarian cancer |
| RIGScan ™ | Navidea Biopharmaceuticals | diagnosis of colorectal cancer |
| rilotumumab | Amgen | colorectal cancer, gastric cancer, prostate cancer, SCLC |
| Rituxan ® (rituximab) | Genentech | diffuse large B-cell lymphoma, B-cell non-Hodgkin lymphoma, indolent non-Hodgkin lymphoma induction therapy, relapsed or refractory CLL |
| RON8 mAb | Eli Lilly, ImClone Systems | cancer |
| SAR3419 (maytansin-loaded anti-CD19 mAb) | Sanofi US | ALL, non-Hodgkin lymphoma |
| SAR153192 (REGN 421) (anti-DLL4 mAb) | Regeneron Pharmaceuticals, Sanofi US | cancer |
| SAR256212 (MM-121) (anti-ErbB3 mAb) | Merrimack Pharmaceuticals, Sanofi US | breast cancer, solid tumors |
| SAR307746 (REGN910) (anti-angiopoietin-2 mAb) | Regeneron Pharmaceuticals, Sanofi US | solid tumors |
| SAR566658 (maytansin-loaded anti-D56) | Sanofi US | DS6-positive solid tumors |
| SAR650984 (anti-CD38 naked mAb) | Sanofi US | hematological malignancies |
| SGN30 | Seattle Genetics | cutaneous anaplastic large-cell lymphoma, systemic anaplastic large-cell lymphoma, Hodgkin's disease |
| SGN-33 (lintuzumab) | Seattle Genetics | AML, myelodysplastic syndromes CLL multiple myeloma, non Hodgkin lymphoma |
| SGN-40 | Seattle Genetics | AML, myelodysplastic syndromes CLL multiple myeloma, non Hodgkin lymphoma |
| SGN-75 (vorsetuzumab mafodotin) | Seattle Genetics | non-Hodgkin lymphoma, renal cancer |
| sibroturtumab | Life Science Pharmaceuticals | colorectal, head and neck, lung cancers |
| Sym004 | EMD Serono, Symphogen | head and neck cancer, solid tumors |
| tabalumab (BAFF inhibitor) | Eli Lilly | multiple myeloma |
| Tarvacin ™ (bavituximab) | Peregrine Pharmaceuticals | solid tumors |
| TF2 | Immunomedics | diagnosis of colorectal cancer |
| TG-1101 (ublituximab) | TG Therapeutics | CLL, non-Hodgkin lymphoma |
| tigatuzumab | Daiichi Sankyo | breast cancer, liver cancer, ovarian cancer, pancreatic cancer |
| TNX-650 | Tanox | refractory Hodgkin lymphoma |
| trastuzumab emtansine (T-DM1) | Genentech, Roche | HER2-positive metastatic breast cancer, early HER2-positive breast cancer, advanced HER2-positive gastric cancer |
| TRC105 | TRACON Pharmaceuticals | bladder cancer, liver cancer, ovarian cancer, prostate cancer, solid tumors |
| tremelimumab (anti-CTLA4 mAb) | AstraZeneca, MedImmune | solid tumors, metastatic melanoma, prostate cancer |
| tumor immunotherapy mAb | Genentech | solid tumors |
| U3-1565 | Daiichi Sankyo | solid tumors |
| urelumab (anti-CD137) | Bristol-Myers Squibb | cancer |
| VAY736 | MorphoSys, Novartis Pharmaceuticals | CLL |
| VB4-845 | Viventia Biotechnologies | bladder cancer |
| Vectibix ® (panitumumab) | Amgen | colorectal cancer |
| VEGFR3 mAb (IMC-3C5) | Eli Lilly, ImClone Systems | cancer |
| veltuzumab (IMMU-106) | Immunomedics | CLL, non-Hodgkin lymphoma |
| VGX-100 | Circadian Technologies | solid tumors |
| volociximab | AbbVie | NSCLC |
| VX15 | Vaccinex | solid tumors |
| Xgeva ® (denosumab) | Amgen | delay or prevention of bone, metastases in prostate cancer or breast cancer, giant cell tumor of the bone |

TABLE 1-continued

Monoclonal Antibodies (mAb)

| Product Name | Company | Indication |
| --- | --- | --- |
| XmAb ® (high ADCC mAb) | Boehringer Ingelheim Pharmaceuticals, Xencor | cancer |
| XmAb ® 2513 (anti-CD30 mAb) | Xencor | Hodgkin disease, T-cell lymphoma |
| XmAb ® 5574 (anti-CD19 mAb) | MorphoSys, Xencor | CLL |
| Y-90 hPAM 4 (IMMU-107) | Immunomedics | pancreatic cancer |
| Yervoy ™ (ipilimumab) | Bristol-Myers Squibb | adjuvant melanoma, NSCLC, prostate cancer, SCLC, gastric cancer, ovarian cancer, leukemia, lymphoma, renal cell cancer |
| zanolimumab | Emergent BioSolutions | peripheral T-cell lymphoma |
| Zevalin ® (ibritumomab tiuxetan) | Spectrum Pharmaceuticals | diffuse large B-cell lymphoma, non-Hodgkin lymphoma |

Infectious diseases

| Product Name | Company | Indication |
| --- | --- | --- |
| ABthrax ™ (raxibacumab) | Human Genome Sciences | anthrax |
| Anthim ™ (ETI-204) | Elusys Therapeutics | anthrax |
| anthrax immune globulin | Cangene | anthrax |
| anti-HIV-1 mAb | Polymun Scientific | HIV infection |
| anti-hsp90 mAb | NeuTec Pharma | candidiasis |
| anti-PD-L1 | Bristol-Myers Squibb | hepatitis B |
| anti-staph mAb | MedImmune | prevention of staphylococcal infections |
| Aurexis (tefibazumab) | Inhibitex | prevention and treatment of *S. aureus* bacteremia |
| bavituximab | Peregrine Pharmaceuticals | hepatitis C |
| CCR5 MAb | Hunan Genome Sciences | HIV infection |
| Cytolin ® (anti-CD8 mAb) | CytoDyn | HIV infection |
| FGI-101-1A6 | Functional Genetics | influenza |
| foravirumab | Crucell | post-exposure prevention of rabies |
| ibalizumab (TMB-355) | TaiMed Biologics USA | HIV-1 infection |
| KB001-A (antibody-fragment product) | KaloBios Pharmaceuticals, Sanofi Pasteur | *Pseudomonas* infections in cystic fibrosis patients, prevention of ventilator-associated pneumonia |
| KD-247 | Kaketsuken | HIV-1 infection |
| MBL-HCV1 | MassBiologics | Hepatitis C |
| MDX-066 (CDA-1) | Medarex | *C. difficile* disease |
| MDX-1303 | Medarex, PharmAthene | anthrax |
| MEDI-557 (RSV mAb-extended half-life) | AstraZeneca, MedImmune | prevention of respiratory syncytial virus (RSV) infections |
| MK-3415A (actoxumab/bezlotoxumab) | Merck | *Clostridium difficile* infections |
| NM01 | SRD Pharmaceuticals | HIV infection |
| Numax ™ (motavizumab) | MedImmune | RSV |
| PRO 140 | CytoDyn | HIV-1 infection |
| SAR279356 (anti-PNAG mAB) | Sanofi US | prevention of bacterial infections |
| Soliris ® (eculizumab) | Alexion Pharmaceuticals | Shiga toxin *E. coli*-related hemolytic uremic syndrome (STEC-HUS) |
| streptococcal B vaccine conjugate | Novartis Vaccines | prevention of streptococcal B infections |
| Synagis ® (palivizumab) | MedImmune | prevention of RSV infections |
| Tarvacin ™ | Peregrine Pharmaceuticals | hepatitis C |
| TCN-032 (IgG mAb) | Theraclone Sciences | influenza A virus infections |
| TCN-202 | Theraclone Sciences | CMV infections |
| Thravixa ™ (fully human anthrax mAb) | Emergent Bio Solutions | post-exposure treatment of anthrax |
| TNX-355 | Tanox | HIV infection |
| UB-421 | United Biomedical | HIV-1 infection |
| XOMA 3AB | XOMA, National Institute of Allergy and Infectious Diseases | botulism |
| XTL 6865 | XTL Biopharmaceuticals | hepatitis C |

Blood disorders

| Product Name | Company | Indication |
| --- | --- | --- |
| afelimomab | Abbot Laboratories | sepsis, septic shock |
| Benlysta ® (belimumab) | GlaxoSmithKline | vasculitis |
| BI-655075 | Boehringer Ingelheim Pharmaceuticals | blood coagulation disorders |
| eculizumab | Alexion Pharmaceuticals | paroxysmal nocturnal hemoglobinurea |

TABLE 1-continued

Monoclonal Antibodies (mAb)

| Product Name | Company | Indication |
|---|---|---|
| ferroportin mAb | Eli Lilly | anemia |
| hepcidin mAb | Eli Lilly | anemia |
| ReoPro ® (abciximab) | Eli Lilly | adjunct to percutaneous coronary intervention for the prevention of cardiac ischemic complications |
| SelG1 | Selexys Pharmaceuticals | sickle cell anemia |
| urtoxazumab | Teijin Pharma | hemolytic uremic |
| Cardiovascular disease | | |
| AMG 145 | Amgen | Hypercholesterolemia, hyperlipoproteinemia type IIa |
| anti-fibrin mAb (3B6/22 Tc-99m) | Agenix | diagnosis of deep vein thrombosis, diagnosis of pulmonary embolism |
| anti-oxLDL (BI-204/RG7418) | BioInvent International, Genentech | atherosclerosis |
| anti-PCSK9 mAb (RG7652) | Genentech | cardiovascular disease |
| GSK249320 | GlaxoSmithKline | stroke |
| IL-1β antibody | Eli Lilly | cardiovascular disease |
| Ilaris ® (canakinumab) | Novartis Pharmaceuticals | secondary prevention of cardiovascular events |
| inclacumab (RG1512) | Roche | peripheral vascular disease |
| MABp1 | XBiotech | vascular restinosis |
| MLN 1202 | Millennium Pharmaceuticals | atherosclerosis |
| pexelizumab | Alexion Pharmaceuticals, Procter & Gamble Pharmaceuticals | acute myocardial infarction, cardiopulmonary bypass |
| PF-04950615 (RN316) | Pfizer | hypercholesterolemia |
| SAR236553/REGN727 (anti-PCSK-9 mAb) | Regeneron Pharmaceuticals, Sanofi US | hypercholesterolemia |
| Diabetes and Related Conditions | | |
| anti-CD3 mAb | MacroGenics | type 1 diabetes |
| gevokizumab (IL-1B inhibitor mAb) | XOMA | type 1 diabetes, type 2 diabetes |
| GSK1070806 (IL-18 mAb) | GlaxoSmithKline | type 2 diabetes |
| Ilaris ® (canakinumab) | Novartis Pharmaceuticals | type 1 diabetes, type 2 diabetes |
| MABp1 | XBiotech | type 2 diabetes |
| OKT3-gamma-1 | Johnson & Johnson | type 1 diabetes |
| teplizumab | MacroGenics | type 1 diabetes |
| TRX 4 (anti-CD3) | TolerRx | type 1 diabetes |
| Eye Conditions | | |
| anti-factor D (RG7417) | Genentech | geographic atrophy associated with age-related macular degeneration |
| anti-LINGO (BI1B033) | Biogen Idec | optic neuritis |
| gevokizumab (IL-1B inhibitor mAb) | XOMA | intermediate or posterior uveitis |
| GSK933776A (anti-B amyloid mAb) | GlaxoSmithKline | age-related macular degeneration |
| Humira ® (adalimumab) | AbbVie | uveitis |
| iSONEP ™ (sonepcizumab) | Lpath | wet age-related macular degeneration |
| Lucentis ® (ranibizumab) | Genentech, Roche | age-related macular degeneration |
| PF-04382923 (RN6G) | Pfizer | age-related macular degeneration |
| secukinumab (AIN457) | Alcon Labs, Novartis Pharmaceuticals | uveitis |
| Soliris ® (eculizumab) | Alexion Pharmaceuticals | severe or refractory neuromyelitis optica |
| Genetic Disorders | | |
| KRN-23 | Kyowa Hakko Kirin Pharma | X-linked dominant hypophosphatemic rickets |
| Soliris ® (eculizumab) | Alexion Pharmaceuticals | paroxysmal nocturnal hemoglobinuria (PNH) |
| Neurological Disorders | | |
| AAB-002 | Janssen Alzheimer Immunotherapy, Pfizer | Alzheimer's disease |
| AAB-003/PF-05236812 | Janssen Alzheimer Immunotherapy, Pfizer | Alzheimer's disease |
| ABT-110 | AbbVie | chronic pain |
| ALD403 | Alder Biopharmaceuticals | prevention of migraine |
| ATI355 (anti-Nogo-A mAb) | Novartis Pharmaceuticals | spinal cord injury |
| BAN2401 (amyloid beta-protein inhibitor) | BioArctic Neuroscience, Eisai | Alzheimer's disease |
| bapineuzumab | Janssen Alzheimer Immunotherapy, Pfizer | Alzheimer's disease |
| crenezumab (anti-Abeta) | Genentech | Alzheimer's disease |
| fulranumab | Janssen Research & Development | cancer pain |
| GSK1223249 (NOGO-A mAb) | GlaxoSmithKline | amyotrophic lateral sclerosis (ALS) |
| GSK933776A (anti-B amyloid mAb) | GlaxoSmithKline | Alzheimer's disease |
| LY2951742 (CGRP peptide) | Arteaus Therapeutics, Eli Lilly | migraine prevention |

TABLE 1-continued

Monoclonal Antibodies (mAb)

| Product Name | Company | Indication |
|---|---|---|
| MEDI-5117 (anti-IL-6 mAb) | AstraZeneca, MedImmune | osteoarthritis pain |
| RG1450 (gantenerumab) | Roche | prodromal Alzheimer's disease |
| RN-307 (anti-CGRP mAb) | Labrys Biologics | migraine |
| RN624 | Rinat Neuroscience | osteoarthritis pain |
| RN1219 | Rinat Neuroscience | Alzheimer's disease |
| SAR228810 (anti-protofibrillar AB mAb) | Sanofi US | Alzheimer's disease |
| solanezumab (LY2062430) | Eli Lilly | Alzheimer's disease |
| tanezumab | Pfizer | chronic pain |

Respiratory Disorders

| Product Name | Company | Indication |
|---|---|---|
| ABN 912 | Novartis Pharmaceuticals | asthma, chronic obstructive pulmonary disorders (COPD) |
| ABX-IL8 | Amgen | COPD |
| ALT-836 | Altor BioScience, Genentech | acute lung injury, adult respiratory distress syndrome |
| AMG 157/MEDI-9929 | Amgen, AstraZeneca | asthma |
| AMG 317 | Amgen | asthma |
| AMG 761 | Amgen | asthma |
| AMG 827 (brodalumab) | Amgen, AstraZeneca | asthma |
| benralizumab | AstraZeneca, MedImmune | asthma, chronic obstructive pulmonary disease (COPD) |
| Bosatria ™ (mepolizumab) | GlaxoSmithKline | asthma |
| carlumab | Janssen Biotech | pulmonary fibrosis |
| CNTO-3157 | Janssen Biotech | asthma |
| CNTO-5825 | Janssen Biotech | allergic asthma |
| daclizumab (anti-CD25 MAb) | Protein Design Labs, Roche | asthma |
| FG-3019 | FibroGen | idiopathic pulmonary fibrosis |
| GS-6624 (simtuzumab) | Gilead Sciences | idiopathic pulmonary fibrosis |
| KB003 | KaloBios Pharmaceuticals | severe asthma |
| MEDI-528 (anti-TL-9 mAb) | MedImmune | asthma |
| MEDI-4212 (anti-IgE mAb) | AstraZeneca, MedImmune | asthma |
| MEDI-7814 (anti-C5/C5a mAb) | AstraZeneca, MedImmune | COPD |
| MEDI-8968 (anti-IL-1R mAb) | AstraZeneca, MedImmune | COPD |
| mepolizumab (anti-TL5 mAb) | GlaxoSmithKline | asthma and nasal polyposis |
| QAX576 | Novartis Pharmaceuticals | asthma, idiopathic pulmonary fibrosis |
| QBX258 | Novartis Pharmaceuticals | asthma |
| QGE031 | Novartis Pharmaceuticals | allergic asthma |
| quilizumab (anti-M1 prime mAb) | Genentech | allergic asthma, allergic rhinitis |
| reslizumab | Cephalon | asthma, eosinophilic esophagitis |
| RG3637 (lebrikizumab) | Genentech, Roche | severe asthma |
| SAR156597 (bispecific interleukin-4/interleukin-13 mAb) | Sanofi US | idiopathic pulmonary fibrosis |
| SAR231893 (anti-IL4 mAb) | Regeneron Pharmaceuticals, Sanofi US | asthma |
| STX-100 | Biogen Idec | idiopathic pulmonary fibrosis |
| TNX-832 | Tanox | respiratory diseases |
| tralokinumab | AstraZeneca, MedImmune | asthma |
| Xolair ® (omalizumab) | Genentech, Novartis Pharmaceuticals | pediatric asthma |

Skin Diseases

| Product Name | Company | Indication |
|---|---|---|
| AbGn-168H | AbGenomics International | plaque psoriasis |
| AMG 827 (brodalumab) | Amgen, AstraZeneca | psoriasis |
| BT-061 | AbbVie, Biotest | plaque psoriasis |
| CNTO-1959 | Janssen Biotech | plaque psoriasis |
| gevokizumab (IL-1B inhibitor mAb) | XOMA | acne vulgaris |
| Humira ® (adalimumab) | AbbVie | hidradenitis suppurativa |
| ixekizumab (IL-17 antibody) | Eli Lilly | psoriasis |
| MABp1 | XBiotech | acne, psoriasis |
| MK-3222 (tildrakizumab) | Merck | plaque psoriasis |
| QGE031 | Novartis Pharmaceuticals | atopic dermatitis |
| REGN846 | Regeneron | atopic dermatitis |
| SAR231893 (anti-IL4 mAb) | Regeneron Pharmaceuticals, Sanofi US | atopic dermatitis |
| secukinumab (AIN457) | Novartis Pharmaceuticals | plaque psoriasis |
| Xolair ® (omalizumab) | Genentech, Novartis Pharmaceuticals | chronic idiopathic urticaria |

Transplantation

| Product Name | Company | Indication |
|---|---|---|
| ASKP-1240 | Astellas Pharma US, Kyowa Hakko Kirin Pharma | prevention of organ transplant rejection |
| Benlysta ® (belimumab) | GlaxoSmithKline | immunosuppression |
| ORTHOCLONE OKT ® 3 (muromomab-CD3) | Ortho Biotech | acute kidney transplant rejection, reversal of heart and liver transplant rejection |

TABLE 1-continued

Monoclonal Antibodies (mAb)

| Product Name | Company | Indication |
| --- | --- | --- |
| OKT3-gamma-1 | Protein Design Labs, Johnson & Johnson | renal transplant rejection |
| Simulect ® (basiliximab) | Novartis Pharmaceuticals | prevention of renal transplant rejection |
| Soliris ® (eculizumab) | Alexion Pharmaceuticals | presensitized kidney transplant (acute humoral rejection) |
| TOL101 | Tolera Therapeutics | prevention of transplant rejection |
| Zenapax ® (daclizumab) | Roche | prophylaxis of acute kidney transplant rejection |

Other

| | | |
| --- | --- | --- |
| anti-IL31 | Bristol-Myers Squibb | immunology |
| anti-TWEAK (BIIB 023) | Biogen Idec | lupus nephritis |
| BAX-69 | Baxter International | lupus nephritis |
| CNTO-5 | Janssen Biotech, MorphoSys | inflammation |
| CNTO-136 (sirukumab) | Janssen Biotech | lupus nephritis |
| CR 0002 | CuraGen | kidney inflammation |
| FB 301 | CytovanceBiologics, Fountain Biopharma | hypersensitivity (IgE-mediated allergic diseases) |
| FG-3019 | FibroGen | liver fibrosis due to chronic hepatitis B infection |
| fresolimumab (TGFβ antagonist) | Genzyme | fibrosis |
| GS-6624 (simtuzumab) | Gilead Sciences | liver fibrosis, myelofibrosis |
| GSK1070806 (anti-interleukin 18 mAb) | GlaxoSmithKline | metabolic disorders |
| Humira ® (adalimumab) | AbbVie | interstitial cystitis |
| LY2382770 (TGF-β antibody) | Eli Lilly | diabetic nephropathy |
| mAb | Genentech | metabolic disorders |
| mepolizumab (anti-IL5 mAb) | GlaxoSmithKline | hypereosinophilic syndrome, eosinophlic esophagitis |
| Meth-mAb | InterveXion Therapeutics | methamfetamine abuse |
| Stelara ® (ustekinumab) | Janssen Biotech | primary biliary cirrhosis |
| VAY736 | MorphoSys, Novartis Pharmaceuticals | inflammation |
| Xolair ® (omalizumab) | Genentech, Tanox | peanut allergy |

Non-limiting examples of protein-based or polypeptide-based biologics include cytokines (e.g., interleukins), chemokines, growth factors, blood-production stimulating proteins (e.g., erythropoietin), hormones (e.g., Elonva® (follicle stimulating hormone), growth hormone), enzymes (e.g., Pulmozyme® (dornase alfa)), clotting factors, insulin, albumin, fragments thereof, conservatively modified variants thereof, analogs thereof, and combinations thereof.

Examples of cytokines include, but are not limited to, TNFα, TNF-related weak inducer of apoptosis (TWEAK), osteoprotegerin (OPG), IFN-α, IFN-β, IFN-γ, interleukins (e.g., IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27), adipocytokines (e.g., leptin, adiponectin, resistin, active or total plasminogen activator inhibitor-1 (PAI-1), visfatin, and retinol binding protein 4 (RBP4)), and combinations thereof. In particular embodiments, the interleukin comprises IL-2 such as Proleukin® (aldesleukin; recombinant IL-2).

Examples of chemokines include, but are not limited to, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, CX$_3$CL1, and combinations thereof.

Non-limiting examples of growth factors include epidermal growth factor (EGF), heparin-binding epidermal growth factor (HB-EGF), vascular endothelial growth factor (VEGF), pigment epithelium-derived factor (PEDF; also known as SERPINF1), amphiregulin (AREG; also known as schwannoma-derived growth factor (SDGF)), basic fibroblast growth factor (bFGF), hepatocyte growth factor (HGF), transforming growth factor-α (TGF-α), transforming growth factor-β (TGF-β1, TGF-β2, TGF-β3, etc.), endothelin-1 (ET-1), keratinocyte growth factor (KGF; also known as FGF7), bone morphogenetic proteins (e.g., BMP1-BMP15), platelet-derived growth factor (PDGF), nerve growth factor (NGF), β-nerve growth factor ((3-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), thrombopoietin (TPO), and combinations thereof.

Examples of receptor construct-based or fusion protein-based biologics include, but are not limited to, naturally-occurring receptors linked to an immunoglobulin frame (e.g., Orencia® (abatacept; immunoglobin CTLA-4 fusion protein), Amevive® (alefacept; IgG1 fusion protein), ENBREL® (etanercept; recombinant human TNF-receptor fusion protein), engineered proteins combining two different polypeptide species (e.g., Ontak® (denileukin diftitox; engineered protein comprising interleukin-2 and diphtheria toxin), and combinations thereof.

The present invention can therefore be used in methods for detecting and measuring the presence or level of a biologic in a sample from a subject receiving biologic therapy for one or more of the diseases or disorders referred to herein and Table 1, including one or more of the following:

Inflammatory diseases, such as inflammatory bowel disease (IBD) (e.g., Crohn's disease (CD) and ulcerative colitis (UC)), uveitis, sarcoidosis, Wegener's granulomatosis, and other diseases with inflammation as a central feature;

Autoimmune diseases, such as rheumatoid arthritis (RA), multiple scleorisis (MS), systemic lupus erythematosus (SLE), ankylosing spondylitis (Bechterew's disease), lupus, psoriatic arthritis, juvenile idiopathic arthritis, psoriasis, erythematosus, and celiac disease;

Cancer, such as digestive and gastrointestinal cancers (e.g., colorectal cancer, small intestine (small bowel) cancer; gastrointestinal stromal tumors, gastrointestinal carcinoid tumors, colon cancer, rectal cancer, anal cancer, bile duct cancer, gastric (stomach) cancer; esophageal cancer; appendix cancer; and the like); gallbladder cancer; liver cancer; pancreatic cancer; breast cancer; lung cancer (e.g., non-small cell lung cancer); prostate cancer; ovarian cancer; renal cancer (e.g., renal cell carcinoma); cancer of the central nervous system; skin cancer; choriocarcinomas; head and neck cancers; hematological malignancies (e.g., leukemia, lymphoma such as B-cell non-Hodgkin's lymphoma); osteogenic sarcomas (e.g., Ewing sarcoma); soft tissue sarcomas (e.g., Dermatofibrosarcoma Protuberans (DFSP), rhabdomyosarcoma); other soft tissue malignancies, and papillary thyroid carcinomas;

Infectious diseases, such as *C. difficile* disease, respiratory syncytial virus (RSV), HIV, anthrax, candidiasis, staphylococcal infections, and hepatitis C;

Blood disorders, such as sepsis, septic shock, paroxysmal nocturnal hemoglobinuria, and hemolytic uremic syndrome;

Cardiovascular disease, such as atherosclerosis, acute myocardial infarction, cardiopulmonary bypass, and angina;

Metabolic disorders, such as diabetes, e.g., type 1 diabetes mellitus and type 2 diabetes;

Genetic disorders, such as paroxysmal nocturnal hemoglobinuria (PNH);

Neurological disorders, such as osteoarthritis pain and Alzheimer's disease;

Respiratory disorders, such as asthma, chronic obstructive pulmonary disorders (COPD), nasal polyposis, and pediatric asthma;

Skin diseases, such as psoriasis, including chronic moderate to severe plaque psoriasis;

Transplant rejection, such as acute kidney transplant rejection, reversal of heart and liver transplant rejection, prevention of renal transplant rejection, prophylaxis of acute kidney transplant rejection, and renal transplant rejection; and/or Other disorders, such as kidney inflammation, postmenopausal osteoporosis (bone disorders), hypereosinophilic syndrome, eosinophilic esophagitis, and peanut allergy.

In particular embodiments, the subject has an inflammatory disease (e.g., inflammatory bowel disease (IBD) such as Crohn's disease (CD) or ulcerative colitis (UC)) or an autoimmune disease (e.g., rheumatoid arthritis).

VIII. Examples

The following examples are offered for illustrative purposes, and are not intended to limit the invention in any manner. Those of skill in the art will readily recognize a variety of non-critical parameters which can be changed or modified to yield essentially the same results.

Example 1

This example illustrates the validation of a homogeneous mobility shift assay (HMSA) for the measurement of vedolizumab (VLM) and anti-VLM antibodies (ATV) in inflammatory bowel disease (IBD) patient serum.

Vedolizumab (VLM), an α4β7 integrin antagonist, is a therapeutic monoclonal antibody recently approved for use in moderate to severe ulcerative colitis or Crohn's disease patients that have failed to demonstrate adequate response to conventional therapies or TNF alpha antagonists. α4β7 integrin is a gut-specific heterodimeric glycoprotein that is important for leukocyte homing to sites of inflammation within the intestine, via its interaction with mucosal addressin cell adhesion molecule-1 (MadCam-1) expressed on the intestinal vascular endothelium. Availability of diagnostic tests to accurately measure VLM drug levels and anti-VLM antibodies is necessary for the effective use of this novel therapeutic in IBD patients. In succession with our anti-TNF alpha therapeutic drug monitoring assays, we have now developed and validated assays to measure VLM and anti-VLM levels in patient serum.

Methods

Soluble α4β7 protein heterodimer was expressed and purified from mammalian cells (e.g., CHO cells). In particular, the integrin α4 subunit was truncated after the thigh domain (α4Δ620) and integrin β7 after the I-EGF 1 domain (β7Δ527) (see, FIG. 13). Acidic/Basic α-helical coiled coil peptides containing one disulfide-bridge forming Cys residue were attached to the C-terminus of the subunits to stabilize the heterodimer (Takagi et al., Embo J., 18:4607-4615 (2003); O'Shea et al., Curr. Biol., 3:658-667 (1993)). A hexahistidine tag was fused to the C-terminus of the basic peptide to facilitate purification. This recombinant heterodimer was used in a "competition" based homogeneous mobility shift assay (HMSA) format to measure VLM levels in sera of patients on VLM therapy. Patient serum was combined with α4β7 to allow therapeutic VLM to bind with α4β7. Subsequently, fluorescently labeled VLM competed with unlabeled VLM is patient sera for binding to its target, α4β7 followed by separation on HPLC size exclusion chromatography. The amount of "free" VLM-alexa fluor determined VLM levels in patient sera. For the anti-VLM assay, standard curves were created by incubating normal human serum containing known amounts of rabbit anti-VLM antibodies with fluorescently labeled VLM; bound and free VLM were then separated by SEC-HPLC. Method validation was determined according to industry recommendations.

Results

Sensitivity for VLM was 0.35 μg/mL. The lower and upper limits of quantitation (LLOQ and ULOQ) were determined to be 0.625 μg/ml and 14 μg/mL, respectively. For anti-VLM, the LLOQ and ULOQ were 3.13 U/ml and 150 U/ml, respectively. The standard curves generated for each assay showed high reproducibility and sensitivity. Inter- and intra-assay precision showed less than 10% CV and accuracy was within 20%. There was no significant interference from lipemic, hemolyzed, or rheumatoid factor (Rf) serum. See, FIGS. 4-10.

Conclusions

A sensitive and specific assay has been developed and validated to measure VLM and anti-VLM levels in patients undergoing treatment for IBD. The assay format required a unique approach owing to the complexity of a large heterodimeric, heavily glycosylated membrane bound antigen as drug target. Both the drug and anti-drug assays demonstrate high accuracy and precision with high sensitivity with a high tolerance to known interfering agents. The assays are useful for clinical monitoring and drug optimization in individual patients.

Example 2

This example illustrates the validation of a homogeneous mobility shift assay (HMSA) and for the measurement of ustekinumab (UTK) and antibodies-to-ustekinumab (ATU) in inflammatory bowel disease (IBD) patient serum.

Ustekinumab is a therapeutic monoclonal antibody which has potential utility in the treatment of IBD in patients that have failed to respond to conventional therapies or TNF alpha antagonists. Ustekinumab is a monoclonal antibody with specificity for interleukin 12 and interleukin 23 via their common p40 subunit and blocks inflammation through these pathways. Here we describe the analytical validation of a HPLC-based high mobility shift assay to measure UTK as well as antibodies-to-ustekinumab.

Methods

Recombinant, soluble IL12p40 subunit (e.g., SEQ ID NO:7) was expressed and purified from mammalian cells. The assay takes advantage of fluorescently labeled UTK competing with unlabeled UTK in patient sera for binding to IL12p40. After incubation of patient sera with recombinant IL12p40, UTK-alexa fluor 488 was added, before running samples on an HPLC size exclusion column which separates "free" UTK-alexa fluor 488 from UTK-alexa fluor 488 which is bound to IL12p40. The amount of "free" UTK-alexa fluor 488 is a measure of the amount of therapeutic UTK in patient sera. The area under the curve (AUC) of the "free" UTK-alexa fluor 488 is plotted against the log of the UTK concentration in known standard samples and UTK concentration in patient sera are calculated by interpolation. For the ATU assay, standard curves were created by incubating normal human serum containing known amounts of rabbit ATU with fluorescently labeled UTK; bound and free GLM were then separated by SEC-HPLC. Method validation was determined according to industry recommendations.

Results

Sensitivity for UTK was 0.15 µg/ml. The upper limit of quantitation (ULOQ) was determined to be 8 µg/mL and the lower limit of quantitation (LLOQ) was determined to be 0.625 µg/ml. For ATU, the LLOQ and ULOQ were 3.13 U/ml and 150 U/ml respectively. The standard curves generated for each assay showed high reproducibility and sensitivity. Inter- and intra-assay precision showed less than 10% CV and accuracy was within 20%. There was no significant interference from lipemic, hemolyzed, or rheumatoid factor (Rf) serum. See, FIGS. 11-12.

Conclusions

This study describes the validation of a novel "competition" based assay to measure ustekinumab levels in patients undergoing treatment for IBD. The assay format required a unique approach owing to complexity of working with this antigen, due to its tendency to form homodimers and heterodimers in serum making usage of a conventional HMSA assay difficult.

The competition-based HMSA assay showed high accuracy and precision with high sensitivity. In addition, the assay has high tolerance to known interfering agents. These assays are useful for clinical monitoring and drug optimization in individual patients.

Example 3

This example illustrates an exemplary vedolizumab (VLM) competition-based assay methodology of the present invention. One of ordinary skill in the art will appreciate that the assay methodology described in this example is applicable to determining the presence or level of ustekinumab (UTK) as well as other biologics in a sample in situations where the complexity of working with the antigen that binds to the biologic (e.g., the antigen is a membrane-bound protein, a glycosylated protein, a multimeric protein, an insoluble protein, a protein that is difficult to express or purify, and/or a large protein) necessitate the use of a soluble form (e.g., a soluble fragment, variant, or monomer) of the antigen.

Normal human serum (NHS) samples spiked with known amounts of vedolizumab (VLM) are serially diluted. Two-fold serial dilutions starting from 80 µg/ml VLM are diluted in NHS to make 10-point curve (i.e., 80 µg/ml to 0.15625 µg/ml). NHS spiked with 12, 4, and 1 µg/ml VLM are used as positive controls. Standard serum samples, positive controls, and patient samples are added to a 96 well plate. Patient samples are added undiluted or diluted 4× or 8× in NHS to increase the assay dynamic range. Soluble α4β7 antigen and assay diluent are added. The plate is placed on a shaker and allowed to incubate at room temperature for 1 hour. After 1 hour, labeled VLM (e.g., VLM-Alexa Fluor® 488) is added. The plate is again placed on a shaker for a 1 hour incubation. Samples are filtered using a 0.2 µm filter plate. Samples are loaded onto an HPLC autosampler and run sequentially through a size exclusion chromatography column (e.g., a Phenomenex BioSep-SEC-s3000 column) which separates free labeled VLM (e.g., VLM-Alexa Fluor® 488) from labeled VLM bound to the soluble α4β7 antigen.

Software written in R-programming language is used to identify the peak representing free labeled VLM (e.g., VLM-Alexa Fluor® 488) and to determine the area of the peak. The area of this peak gets larger when there is VLM in the patient's sera. By comparing the size of this peak to the standard curve, one can interpolate the patient's VLM levels.

Prism (e.g., GraphPad Prism 6) is used to generate a standard curve by plotting the area of free labeled VLM (e.g., VLM-Alexa Fluor® 488) as a function of serum VLM levels. By comparing the size of this peak to the standard curve, one can interpolate the patient's VLM drug concentration.

The assay described in this example is premised on the competition between the VLM in a sample from a patient receiving VLM therapy and the labeled VLM added to the sample reaction for binding to the soluble α4β7 antigen. The relative ratios of labeled and unlabeled VLM determines how much α4β7 antigen is bound to each and determines the free labeled VLM (e.g., VLM-Alexa Fluor® 488) peak area. The more drug present in the patient sample, the more the labeled VLM remains free as opposed to bound to the α4β7 antigen.

Example 4

This example illustrates the validation of a homogeneous mobility shift assay (HMSA) for the measurement of vedolizumab (VLM) and anti-VLM antibodies in inflammatory bowel disease (IBD) patient serum.

Background and Aims

Vedolizumab, an α4β7 integrin antagonist, is a therapeutic monoclonal antibody recently approved for use in moderate to severe ulcerative colitis and Crohn's disease patients that have failed to demonstrate adequate response to conventional therapies or TNFα antagonists. Availability of diagnostic tests to accurately measure serum VLM and anti-VLM (ATV) levels is necessary for the effective use of this novel therapeutic in IBD patients. Here we describe the analytical validation of the HMSA developed to measure VDM and ATV levels in patient serum as well as its clinical utility.

Methods

Soluble α4β7 heterodimer (e.g., α4Δ620/β7Δ527 heterodimer; see, FIG. 13) was expressed and purified in mammalian cells. This recombinant heterodimer was used in a "competition" based HMSA format to measure serum VLM levels in patients on VLM therapy. Patient serum was combined with α4β7 to allow therapeutic VLM to bind with α4β7. Subsequently, fluorescently labeled VLM competed with unlabeled VLM in patient sera for binding to its target, α4β7, followed by separation on HPLC size exclusion chromatography (see, FIG. 1). For the anti-VLM assay, standard curves were created by incubating normal human serum containing known amounts of rabbit anti-VLM antibodies with fluorescently labeled VLM; bound and free VLM were then separated by SEC-HPLC. Validation was performed according to industry recommendations (Shankar, G., et al. 2008).

Results

VLM and ATV assays show high intra-assay precision and accuracy. Intra-assay precision is less than 10% and intra-assay accuracy is less than 15% error. Run to run, instrument to instrument, and analyst to analyst variability are less than 15% CV and less than 20% error in almost all cases. (Table 2). Sensitivity for VLM was 0.348 µg/mL with a dynamic range of 0.625-14 µg/mL (Table 3). The limit of detection for the ATV assay is <1.56 U/mL. A precise value could not be determined as it is too low to interpolate our curve. The dynamic range for ATV was 3.13-150 U/mL in undiluted serum (Table 3). Normal human serum spiked with VLM or ATV showed good linearity and recovery across serial dilutions (FIGS. 14A and 14B). ATV shows high drug tolerance at levels of 20 µg/mL of VLM (Table 4). Common interfering agents in patient serum were tested and did not interfere at levels seen in IBD patients (FIGS. 15A, 15B and 15C).

TABLE 2

Validation data for accuracy and precision of the assays.

Accuracy and Precision of the VLM-HMSA

| | Intra-Assay Precision | | | | | | Inter-Assay Precision | | | | | |
|---|---|---|---|---|---|---|---|---|---|---|---|---|
| | | | | | | | | | | Instrument | | |
| | (n = 10) | | | Run to Run (n = 10) | | | Analyst to Analyst (n = 5) | | | to Instrument (n = 10) | | |
| | Hgh | Med | Low | High | Med | Low | High | Med | Low | High | Med | Low |
| Expected (µ/mL) | 12 | 4 | 1 | 12 | 4 | 1 | 12 | 4 | 1 | 12 | 4 | 1 |
| Measured (Mean, U/mL) | 10.34 | 4.36 | 0.89 | 11.22 | 4.16 | 1.13 | 10.51 | 4.19 | 1.05 | 12.30 | 4.18 | 1.29 |
| SD | 0.56 | 0.21 | 0.10 | 1.11 | 0.17 | 0.18 | 0.47 | 0.33 | 0.16 | 0.86 | 0.19 | 0.08 |
| CV % | 5.45 | 4.82 | 11.64 | 9.87 | 4.07 | 14.53 | 4.46 | 7.97 | 14.91 | 6.97 | 4.44 | 6.07 |
| Accuracy (% Error) | 13.83 | 9.07 | 11.00 | 6.48 | 3.91 | 12.72 | 12.44 | 4.76 | 5.30 | 2.46 | 4.44 | 29.04 |

Accuracy and Precision of the ATV-HMSA

| | Intra-Assay Precision | | | | | | Inter-Assay Precision | | | | | |
|---|---|---|---|---|---|---|---|---|---|---|---|---|
| | | | | | | | | | | Instrument | | |
| | (n = 10) | | | Run to Run (n = 10) | | | Analyst to Analyst (n = 10) | | | to Instrument (n = 10) | | |
| | Hgh | Med | Low | High | Med | Low | High | Med | Low | High | Med | Low |
| Expected (U/mL) | 50 | 25 | 12.5 | 50 | 25 | 12.5 | 50 | 25 | 12.5 | 50 | 25 | 12.5 |
| Measured (Mean, U/mL) | 47.31 | 23.32 | 11.72 | 51.53 | 25.01 | 13.54 | 51.52 | 25.56 | 13.51 | 47.31 | 23.34 | 11.75 |
| SD | 2.82 | 1.51 | 0.79 | 5.00 | 3.39 | 1.76 | 5.00 | 2.43 | 1.86 | 2.73 | 1.46 | 0.78 |
| CV % | 5.96 | 6.46 | 6.75 | 9.71 | 13.56 | 13.00 | 9.71 | 9.52 | 13.78 | 5.77 | 6.25 | 6.62 |
| Accuracy (% Error) | 5.37 | 6.71 | 6.27 | 7.93 | 0.04 | 8.32 | 3.04 | 2.25 | 8.06 | 5.38 | 6.65 | 5.96 |

TABLE 3

Limits of quantitation for each assay.

| Assay | Limit of Blank | Limit of Detection | Lower Limit of Quantitation | Upper Limit of Quantitation |
|---|---|---|---|---|
| VLM-HMSA | n = 30 0.054 µg/mL | n = 30 0.348 µg/mL | n = 36 0.625 µg/mL | n = 36 14 µg/mL |
| ATV-HMSA | n = 25 <1.56 U/mL | n = 25 <1.56 U/mL | n = 36 3.13 U/mL | n = 36 150 U/mL |

TABLE 4

Drug interference in the anti-VLM assay.

| Vedo [µg/mL] | Total ATV [U/mL] |
|---|---|
| 20 | 51.6 |
| 0 | 49.2 |
| 20 | 26.4 |
| 0 | 24.8 |
| 20 | 13 |
| 0 | 14 |

Conclusions

A sensitive and specific assay has been developed and validated to measure VLM and anti-VLM levels in patients undergoing treatment for IBD. The assay format required a unique approach owing to the complexity of a large heterodimeric, heavily glycosylated membrane protein as drug target. Both the drug and anti-drug assays demonstrate high accuracy and precision with tolerance to known interfering agents. The development of VLM and anti-VLM assays is useful for clinical monitoring and drug optimization in individual patients.

Example 5

This example illustrates the validation of a homogeneous mobility shift assay (HMSA) for the measurement of ustekinumab (UTK) and antibodies-to-ustekinumab (ATU) in inflammatory bowel disease (IBD) patient serum.

Background and Aims

Ustekinumab is a therapeutic monoclonal antibody which has potential utility in the treatment IBD patients that have failed to respond to conventional therapies or TNFα antagonists. Ustekinumab is specific for IL-12 and IL-23 via their common p40 subunit and blocks inflammation through these pathways. Availability of diagnostic tests to accurately measure serum UST and anti-UST (ATU) levels is necessary for the effective use of this novel therapeutic in IBD patients. Here we describe the analytical validation of a "competition" based HMSA developed to measure UTK levels as well as conventional HMSA to measure ATU levels in patient serum.

Methods

Recombinant, soluble IL12p40 (e.g., SEQ ID NO:7) was expressed and purified from mammalian cells. Recombinant IL12p40 was used in a "competition" based HMSA format to measure serum UTK levels in patients on UTK therapy. Patient serum was combined with rIL12p40 to allow therapeutic UTK to bind with rIL12p40. Subsequently, fluorescently labeled UTK competed with unlabeled UTK in patient sera for binding to its target, rIL12p40, followed by separation on HPLC size exclusion chromatography (see, FIG. 16). For the anti-UTK assay, standard curves were created by incubating normal human serum containing known amounts of rabbit anti-UTK antibodies with fluorescently labeled UTK; bound and free UTK were then separated by SEC-HPLC.

Results

UTK and ATU assays show high intra-assay precision and accuracy. Intra-assay precision is less than 10% and intra-assay accuracy is less than 15% error. Run to run, instrument to instrument, and analyst to analyst variability are less than 15% CV and less than 20% error. (Table 5). Sensitivity for UTK is 0.224 µg/mL with a dynamic range of 0.625-10 µg/mL (Table 6). The limit of detection for the ATU assay is <1.56 U/mL. A precise value could not be determined as it is too low to interpolate from the standard curve. The dynamic range for ATU is 3.13-150 U/mL in undiluted serum (Table 6). Normal human serum spiked with UTK or ATU showed good linearity and recovery across serial dilutions within the assay's dynamic range (FIGS. 17A and 17B). ATU shows high drug tolerance. Levels of 20 µg/mL of UTK do not significantly interfere with ATU detection (Table 7). Common interfering agents in patient serum were tested and did not interfere at levels seen in IBD patients. Only highly hemolyzed serum may potentially interfere but not at levels normally seen in patient sera (FIGS. 18A, 18B and 18C).

TABLE 5

Validation data for precision and accuracy of the assays.

Accuracy and Precision of the UTK-HMSA

| | Intra-Assay Precision | | | | | | Inter-Assay Precision | | | | | |
|---|---|---|---|---|---|---|---|---|---|---|---|---|
| | (n = 5) | | | Run to Run (n = 5) | | | Analyst to Analyst (n = 5) | | | Instrument to Instrument (n = 5) | | |
| | Hgh | Med | Low | High | Med | Low | High | Med | Low | High | Med | Low |
| Expected (µg/mL) | 10 | 5 | 2.5 | 10 | 5 | 2.5 | 10 | 5 | 2.5 | 10 | 5 | 2.5 |
| Measured (Mean, µg/mL) | 8.89 | 4.52 | 2.40 | 10.59 | 5.03 | 2.59 | 10.09 | 4.93 | 2.66 | 10.29 | 5.26 | 2.89 |

TABLE 5-continued

Validation data for precision and accuracy of the assays.

| | | | | | | | | | | | | |
|---|---|---|---|---|---|---|---|---|---|---|---|---|
| SD | 0.62 | 0.08 | 0.05 | 0.97 | 0.29 | 0.13 | 0.52 | 0.27 | 0.18 | 0.49 | 0.29 | 0.09 |
| CV % | 6.96 | 1.76 | 2.16 | 9.18 | 5.67 | 5.06 | 5.18 | 5.39 | 6.95 | 4.79 | 5.44 | 3.15 |
| Accuracy (% Error) | 11.14 | 9.55 | 4.03 | 5.88 | 0.69 | 3.71 | 0.94 | 1.42 | 6.23 | 2.87 | 5.28 | 15.43 |

Accuracy and Precision of the ATU-HMSA

| | Intra-Assay Precision | | | | | | Inter-Assay Precision | | | | | |
|---|---|---|---|---|---|---|---|---|---|---|---|---|
| | (n = 5) | | | Run to Run (n5) | | | Analyst to Analyst (n = 5) | | | Instrument to Instrument (n = 5) | | |
| | Hgh | Med | Low | High | Med | Low | High | Med | Low | High | Med | Low |
| Expected (U/mL) | 50 | 20 | 10 | 50 | 20 | 10 | 50 | 20 | 10 | 50 | 20 | 10 |
| Measured (Mean, U/mL) | 49.61 | 21.08 | 9.47 | 50.63 | 21.51 | 9.20 | 51.24 | 21.48 | 9.19 | 49.61 | 20.39 | 8.78 |
| SD | 0.33 | 0.83 | 0.78 | 1.16 | 0.73 | 0.60 | 1.80 | 0.73 | 0.61 | 1.85 | 0.69 | 0.20 |
| CV % | 0.67 | 3.95 | 8.27 | 2.30 | 3.39 | 6.52 | 3.51 | 3.39 | 6.60 | 3.74 | 3.37 | 2.30 |
| Accuracy (% Error) | 0.79 | 5.42 | 5.30 | 1.25 | 7.54 | 7.96 | 2.47 | 7.41 | 8.11 | 0.79 | 1.97 | 12.23 |

TABLE 6

Limits of quantitation for each assay.
Limits of Quantitation

| Assay | Limit of Blank | Limit of Detection | Lower Limit of Quantitation | Upper Limit of Quantitation |
|---|---|---|---|---|
| UTK-HMSA | n = 30 | n = 30 | n = 36 | n = 36 |
| | 0.077 µg/mL | 0.224 µg/mL | 0.625 µg/mL | 10 µg/mL |
| ATU-HMSA | n = 30 | n = 30 | n = 30 | n = 30 |
| | Too low to interpolate | <1.56 U/mL | 3.13 U/mL | 150 U/mL |

TABLE 7

Drug interference in the anti-UTK assay.

| UTK [µg/mL] | Total ATU [U/mL] |
|---|---|
| 20 | 58.8 |
| 0 | 51.7 |
| 20 | 16.7 |
| 0 | 22.1 |
| 20 | 5.6 |
| 0 | 9.2 |

Conclusions

HMSA for UTK and ATU showed high accuracy and precision across a wide dynamic range. The HMSA platform allowed detection of UTK and ATU even in the presence of interfering agents which are known to limit the utility of ELISA/ECLIA methods. The development of a new "competition" based HMSA platform allows for the measurement of therapeutic drug levels when a conventional HMSA is not feasible.

Example 6

This example illustrates experiments performed to improve the dynamic range of the homogeneous mobility shift assay (HMSA) for the measurement of vedolizumab (VDZ).

In an effort to improve the assay's dynamic range, the assay was modified by increasing the amount of VDZ-Alexa488 used in the assay 1.6-fold. Increasing the amount of labeled VDZ and proportionately increasing the amount of α4β7 antigen (e.g., α4Δ620/β7Δ527 heterodimer; see, FIG. 13) increased the dynamic range of the assay. In addition, changing the amount of α4β7 relative to labeled VDZ affected the lower limit of quantification. Excess antigen relative to labeled VDZ made the assay relatively insensitive to drug in patient sera and raised the lower limit of quantification. Conversely, too little antigen relative to labeled VDZ had the effect of lowering the upper limit of quantification. Increasing the amount of labeled VDZ from 75 ng/well to 120 ng/well (1.6-fold) and titrating the antigen such that the presence of antigen binds up 75-80% of the labeled VDZ provided the best compromise between the low-end sensitivity needed as well as an improved dynamic range that would enable the measurement of drug in patient sera without requiring dilutions in most cases.

In addition, the data is plotted such that the area of the VDZ-Alexa488 peak (without dividing by the Blocked-Alexa 488 control peak area) is plotted against the log of the VDZ concentration.

1. Assay Limits

Limit of Blank

The Limit of Blank (LOB) was determined from 30 replicates of the standard curve blank. The standard curve blank (negative control) in all assays consisted of 4% normal human serum+40 ng VDZ-Alexa488+165 ng α4β7 per 100 µL injection. The average (mean)+1.645SD of the VDZ-Alexa488 peak area was calculated and then used for calculation of the LOD.

TABLE 8

| Assay Limit of Blank (LOB). | |
| --- | --- |
| N | 30 |
| Mean (VDZ-Alexa488 peak area) | 1.91 |
| SD (VDZ-Alexa488 peak area) | 0.09 |
| The average (mean) + 1.645 SD | 2.06 |
| Interpolated LOB | 0.156/ml* |

*The average (mean) + 1.645 SD was just below the lowest point of the curve and therefore the lowest point on the curve was taken for the LOB.

Limit of Detection

The Limit of Detection (LOD) was determined by utilizing the measured LOB and replicates of serum containing VDZ at a low concentration which is approaching the LOB. Standard 10 was chosen because it is the lowest point on the curve and nearest the LOB. The LOD was calculated using the equation: $LOD = LOB + 1.645(SD_{low\ concentration\ sample})$ (Armbruster et al., 2008). The value was then interpolated from the averaged standard curve of the experiments used in the calculation to yield the concentration in µg/mL.

TABLE 9

| Assay Limit of Detection. | |
| --- | --- |
| N | 30 |
| Mean (VDZ-Alexa488 peak area) | 1.91 |
| SD (VDZ-Alexa488 peak area) | 0.061 |
| 1.645*SD | 0.100 |
| Interpolated (1.645*SD) | Too low to interpolate |
| LOD = The average (mean) + 3*SD | 0.457 µg/mL |

Limit of Quantitation

The Lower Limit of Quantitation (LLOQ) was determined by analyzing interpolated concentrations of 30 replicates of a low concentration VDZ positive sample. In this case, standard 8 (effective serum concentration of 0.625 µg/mL) was chosen. The upper limit of quantitation (ULOQ) was determined by analyzing 30 replicates of a high concentration VDZ positive sample (effective serum concentration equal to 14 µg/mL). LLOQ was defined as the concentration that results in a CV≤20% with Error≤25% and thus measures the assay's precision and accuracy at a low analyte concentration. The ULOQ was also qualified by CV≤20% with Error≤25%.

TABLE 10

| LLOQ and ULOQ. | | |
| --- | --- | --- |
|  | LLOQ | ULOQ |
| N | 30 | 30 |
| Expected (µg/mL) | 1 | 25 |
| Mean (µg/mL) | 1.05 | 20.95 |
| SD (µg/mL) | 0.12 | 1.44 |
| CV (%) | 11.39 | 6.86 |
| Error (%) | 5.13 | −16.19 |

These criteria resulted in the following values for the Assay Limits:

TABLE 11

| Assays Limits of Quantitation. | |
| --- | --- |
| LOD | 0.457 µg/mL |
| LLOQ | 1 µg/mL |
| ULOQ | 25 µg/mL |

2. Interference

Antibody to Vedolizumab (ATV) Interference

In this experiment, 2.5, 5, 10 and 20 µg/mL VDZ was added to either normal human serum or various concentrations of rabbit ATV positive serum. These samples were then analyzed using the assay and the % recovery calculated.

TABLE 12

| ATV Interference. | | | | | | | |
| --- | --- | --- | --- | --- | --- | --- | --- |
| VDZ spike (µg/mL) | Measured VDZ (µg/mL) Control (No ATV) | % Recovery | | | | | |
| | | 0 U/mL | 3.13 U/mL | 6.25 U/mL | 12.5 U/mL | 25 U/mL | 50 U/mL |
| 2.5 | 2.23 | 100 | 90 | 82 | 62 | 0 | 0 |
| 5 | 4.47 | 100 | 93 | 88 | 77 | 60 | 22 |
| 10 | 9.15 | 100 | 91 | 85 | 77 | 71 | 55 |
| 20 | 17.53 | 100 | 87 | 81 | 73 | 69 | 59 |

The assay tolerance to ATV is up to 6.25 U/ml in this experiment. The ATV interference is expected as neutralizing ATV will compete with α4β7 for binding to patient VDZ. Only VDZ bound to non-neutralizing ATV is expected to be detected.

Integrin α4β7 Substrate Interference

To test the interference of α4β7, titrations were performed in the range of 1 to 1000 ng/mL. VDZ concentrations were plotted on the intercept of the X-axis correspond to the zero concentration of each interfering agent (FIG. 19).

TABLE 13

| α4β7 Interference (100 ng/mL). | | | |
| --- | --- | --- | --- |
| VDZ Positive Control | High Control (12 µg/mL) | Medium Control (4 µg/mL) | Low Control (1 µg/mL) |
| Mean (µg/mL) | 12.57 | 3.77 | 1.22 |
| SD (µg/mL) | 0.23 | 0.01 | 0.04 |

TABLE 13-continued

α4β7 Interference (100 ng/mL).

| VDZ Positive Control | High Control (12 µg/mL) | Medium Control (4 µg/mL) | Low Control (1 µg/mL) |
|---|---|---|---|
| CV (%) | 1.8 | 0.3 | 3.5 |
| Recovery (%) | 109.6 | 108.1 | 106.7 |

There was no significant interference from levels of α4β7 far exceeding levels one would expect to see in sera from patients being treated with VDZ.

3. Antigen Stability

The stability of α4β7 antigen was assessed through storage at 4 degrees (4° C.) for 1 week. After 1 week, the α4β7 was removed from 4° C. storage and analyzed against a fresh aliquot stored at −70° C. The data from the 4° C. storage samples was then compared to that obtained before storage and the percent error calculated. The aliquots were deemed stable at 4° C. if the error was within 25%.

TABLE 14

Accelerated Stability.

| | Time Point | | | | | |
|---|---|---|---|---|---|---|
| | Week 0 | | | Week 1 | | |
| VDZ Pos. Ctrl | High | Med | Low | High | Med | Low |
| 4° C. Mean (µg/mL) | 10.00 | 3.15 | 0.88 | 11.06 | 4.42 | 1.12 |
| SD (µg/mL) | 0.21 | 0.45 | 0.06 | 0.81 | 0.21 | 0.06 |
| CV (%) | 2.11 | 14.24 | 6.65 | 7.32 | 4.81 | 5.21 |
| Error (%) | −16.64 | −21.35 | −12.34 | −7.81 | 10.50 | 12.05 |

Accelerated stability of α4β7. Antigen stored at −70° C. was used in the assay to test VDZ positive controls. Controls came out within specifications (Error≤25% and CV≤25%). Antigen stored at 4° C. was used in the assay to test VDZ positive controls. These controls also came out within specifications. In addition, there was no obvious loss of antigen potency as a result of being stored at 4° C. versus −70° C.

4. Additional Dynamic Range Experiments

Three standard curves were generated using a 1× amount of labeled VDZ (e.g., 75 ng/well of VDZ-Alexa488), as well as 2× and 4× amounts. FIG. 20 shows that proportionately increasing the concentrations of both VDZ-Alexa488 and integrin α4β7 used in the assay increases the assay's dynamic range. It also increases anti-drug antibody tolerance. A maximum LLOQ of 1 µg/mL was the criteria for this assay. In particular, increasing the amount of labeled VDZ and α4β7 by 1.6-fold enabled a maximum LLOQ of 1 µg/mL while providing an improved top-end range of 25 µg/mL (see, Table 11).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

```
INFORMAL SEQUENCE LISTING

SEQ ID NO: 1
Human alpha 4 integrin fragment
MAWEARREPGPRRAAVRETVMLLLCLGVPTGRPYNVDTESALLYQGPHNTLFGYSVVLHSHGANRWLLVG
APTANWLANASVINPGAIYRCRIGKNPGQTCEQLQLGSPNGEPCGKTCLEERDNQWLGVTLSRQPGENGS
IVTCGHRWKNIFYIKNENKLPTGGCYGVPPDLRTELSKRIAPCYQDYVKKFGENFASCQAGISSFYTKDL
IVMGAPGSSYWTGSLFVYNITTNKYKAFLDKQNQVKFGSYLGYSVGAGHFRSQHTTEVVGGAPQHEQIGK
AYIFSIDEKELNILHEMKGKKLGSYFGASVCAVDLNADGFSDLLVGAPMQSTIREEGRVFVYINSGSGAV
MNAMETNLVGSDKYAARFGESIVNLGDIDNDGFEDVAIGAPQEDDLQGAIYIYNGRADGISSIFSQRIEG
LQISKSLSMFGQSISGQIDADNNGYVDVAVGAFRSDSAVLLRIRPVVIVDASLSHPESVNRIKFDCVENG
WPSVCIDLTLCFSYKGKEVPGYIVLEYNMSLDVNRKAESPPREYESSNGTSDVITGSIQVSSREANCRTH
QAFMRKDVRDILTPIQIEAAYHLGPHVISKRSTEEFPPLQPILQQKKEKDIMKKTINFAR SEQ ID NO: 2
Human beta 7 integrin fragment
MVALPMVLVLLLVLSRGESELDAKIPSTGDATEWRNPHLSMLGSCQPAPSCQKCILSHPSCAWCKQLNFT
ASGEAEARRCARREELLARGCPLEELEEPRGQQEVLQDQPLSQGARGEGATQLAPQRVRVILRPGEPQQL
QVRFLRAEGYPVDLYYLMDLSYSMKDDLERVRQLGHALLVRLQEVIHSVRIGFGSFVDKTVLPFVSTVPS
KLRHPCPTRLERCQSPFSPHHVLSLIGDAQAFEREVGRQSVSGNLDSPEGGFDAILQAALCQEQIGWRNV
SRLLVFTSDDIFHTAGDGKLGGIFMPSDGHCHLDSNGLYSRSTEFDYPSVGQVAQALSAANIQPIFAVIS
AALPVYQELSKLIPKSAVGELSEDSSNVVQLIMDAYNSLSSIVTLEHSSLPPGVHISYESQCEGPEKREG
KAEDRGQCNHVRINQTVIFWVSLQATHCLPEPHLLRLRALGESEELIVELHTLCDCNCSDIQPQAPHCSD
GQGHLQCGVCSCAPGRLGRLCECSVAELSSPDLESGC SEQ ID NO: 3
Human alpha 4 integrin fragment with acidic peptide
MAWEARREPGPRRAAVRETVMLLLCLGVPIGRPYNVDTESALLYQGPHNTLFGYSVVLHSHGANRWLLVG
APTANWLANASVINPGQIYRCRIGKNPGQICEQLQLGSPNGEPCGKICLEERDNQWLGVILSRQPGENGS
IVICGHRWKNIFYIKNENKLPIGGCYGVPPDLRTELSKRIAPCYQDYVKKFGENFASCQAGISSFYIKDL
IVMGAPGSSYWIGSLEVYNITINKYKAFLDKQNQVKFGSYLGYSVGAGHERSQHTTEVVGGAPQHEQIGK
AYIFSIDEKELNILHEMKGKKLGSYFGASVCAVDLNADGFSDLLVGAPMQSTIREEGRVFVYINSGSGAV
MNAMETNLVGSDKYAARFGESIVNLGDIDNDGFEDVAIGAPQEDDLQGAIYIYNGRADGISSIFSQRIEG
LQISKSLSMFGQSISGQIDADNNGYVDVAVGAFRSDSAVLLRIRPVVIVDASLSHPESVNRIKFDCVENG
```

| INFORMAL SEQUENCE LISTING |
| --- |

WPSVCIDLTLCFSYKGKEVPGYIVLEYNMSLDVNRKAESPPREYESSNGTSDVITGSIQVSSREANCRTH
QAFMRKDVRDILTPIQIEAAYHLGPHVISKRSTEEFPPLQPILQQKKEKDIMKKTINFARTGGLAQCEKE
LQALEKENAQLEWELQALEKELAQ

SEQ ID NO: 4
Human beta 7 integrin fragment with the BASE-p1 sequence of peptide
Velcro containing a Cys at the "d" positions of the heptad repeat
peptide with TEV cleavage site and His6 tag
MVALPMVLVLLLVLSRGESELDAKIPSTGDATEWRNPHLSMLGSCQPAPSCQKCILSHPSCAWCKQLNFT
ASGEAEARRCARREELLARGCPLEELEEPRGQQEVLQDQPLSQGARGEGATQLAPQRVRVILRPGEPQQL
QVRFLRAEGYPVDLYYLMDLSYSMKDDLERVRQLGHALLVRLQEVIHSVRIGFGSFVDKTVLPFVSTVPS
KLRHPCPTRLERCQSPFSFHHVLSLIGDAQAFEREVGRQSVSGNLDSPEGGFDAILQAALCQEQIGWRNV
SRLLVFTSDDIFHTAGDGKLGGIFMPSDGHCHLDSNGLYSRSTEFDYPSVGQVAQALSAANIQPIFAVIS
AALPVYQELSKLIPKSAVGELSEDSSNVVQLIMDAYNSLSSIVTLEHSSLPPGVHISYESQCEGPEKREG
KAEDRGQCNHVRINQTVIFWVSLQATHCLPEPHLLRLRALGESEELIVELHTLCDCNCSDIQPQAPHCSD
GQGHLQCGVCSCAPGRLGRLCECSVAELSSPDLESGCGGLENGYFQGGKNAQCKKKLQALKKKNAQLKWK
LQALKKKLAQGGHHHHHH SEQ ID NO: 5
Human IL-12p40 wild-type
MCHQQLVISWFSLVFLASPLVAIWELKKDVYVVELDWYPDAPGEMVVLICDTPEEDGITWILDQSSEVLG
SGKILTIQVKEFGDAGQYTCHKGGEVLSHSLLLLHKKEDGIWSTDILKDQKEPKNKTFLRCEAKNYSGRF
TCWWLITISIDLIFSVKSSRGSSDPQGVICGAATLSAERVRGDNKEYEYSVECQEDSACPAAEESLPIEV
MVDAVHKLKYENYISSFFIRDIIKPDPPKNLQLKPLKNSRQVEVSWEYPDTWSTPHSYFSLIFCVQVQGK
SKREKKDRVFIDKISATVICRKNASISVRAQDRYYSSSWSEWASVPC SEQ ID NO: 6
Human IL-12p40 variant (C199A, C274A)
MCHQQLVISWFSLVFLASPLVAIWELKKDVYVVELDWYPDAPGEMVVLTCDTPEEDGITWTLDQSSEVLG
SGKTLTIQVKEFGDAGQYTCHKGGEVLSHSLLLLHKKEDGIWSTDILKDQKEPKNKTFLRCEAKNYSGRF
TCWWLTTISTDLTFSVKSSRGSSDPQGVTCGAATLSAERVRGDNKEYEYSVECQEDSAAPAAEESLPIEV
MVDAVHKLKYENYTSSFFIRDIIKPDPPKNLQLKPLKNSRQVEVSWEYPDTWSTPHSYFSLTFAVQVQGK
SKREKKDRVFIDKISATVICRKNASISVRAQDRYYSSSWSEWASVPC SEQ ID NO: 7
Human IL-12p40 variant (C199A, C274A) with hexahistidine tag
MCHQQLVISWFSLVFLASPLVAIWELKKDVYVVELDWYPDAPGEMVVLTCDTPEEDGITWTLDQSSEVLG
SGKTLTIQVKEFGDAGQYTCHKGGEVLSHSLLLLHKKEDGIWSTDILKDQKEPKNKTFLRCEAKNYSGRF
TCWWLTTISTDLTFSVKSSRGSSDPQGVTCGAATLSAERVRGDNKEYEYSVECQEDSAAPAAEESLPIEV
MVDAVHKLKYENYTSSFFIRDIIKPDPPKNLQLKPLKNSRQVEVSWEYPDTWSTPHSYFSLTFAVQVQGK
SKREKKDRVFIDKISATVICRKNASISVRAQDRYYSSSWSEWASVPCHHHHHH SEQ ID NO: 8
ACID peptide with cysteine residue (3)
AQCEKELQALEKENAQLEWELQALEKELAQ SEQ ID NO: 9
BASE peptide with cysteine residue (16), TEV cleavage site (3-9), and
hexahistidine tag (46-51)
GGLENGYFQGGKNAQCKKKLQALKKKNAQLKWKLQALKKKLAQGGHHHHHH SEQ ID NO: 10
TEV cleavage site
EXXYXQ/S
X is any amino acid residue SEQ ID NO: 11
Human IL-12p40 variant (C199S, C274S)
MCHQQLVISWFSLVFLASPLVAIWELKKDVYVVELDWYPDAPGEMVVLTCDTPEEDGITWTLDQSSEVLG
SGKTLTIQVKEFGDAGQYTCHKGGEVLSHSLLLLHKKEDGIWSTDILKDQKEPKNKTFLRCEAKNYSGRF
TCWWLTTISTDLTFSVKSSRGSSDPQGVTCGAATLSAERVRGDNKEYEYSVECQEDSASPAAEESLPIEV
MVDAVHKLKYENYTSSFFIRDIIKPDPPKNLQLKPLKNSRQVEVSWEYPDTWSTPHSYFSLTFSVQVQGK
SKREKKDRVFIDKISATVICRKNASISVRAQDRYYSSSWSEWASVPC SEQ ID NO: 12
Human IL-12p40 variant (C199A, C274S)
MCHQQLVISWFSLVFLASPLVAIWELKKDVYVVELDWYPDAPGEMVVLTCDTPEEDGITWTLDQSSEVLG
SGKTLTIQVKEFGDAGQYTCHKGGEVLSHSLLLLHKKEDGIWSTDILKDQKEPKNKTFLRCEAKNYSGRF
TCWWLTTISTDLTFSVKSSRGSSDPQGVTCGAATLSAERVRGDNKEYEYSVECQEDSAAPAAEESLPIEV
MVDAVHKLKYENYTSSFFIRDIIKPDPPKNLQLKPLKNSRQVEVSWEYPDTWSTPHSYFSLTFSVQVQGK
SKREKKDRVFIDKISATVICRKNASISVRAQDRYYSSSWSEWASVPC

INFORMAL SEQUENCE LISTING

SEQ ID NO: 13
Human IL-12p40 variant (C199S, C274A)
MCHQQLVISWFSLVFLASPLVAIWELKKDVYVVELDWYPDAPGEMVVLTCDTPEEDGITWTLDQSSEVLG
SGKTLTIQVKEFGDAGQYTCHKGGEVLSHSLLLLHKKEDGIWSTDILKDQKEPKNKTFLRCEAKNYSGRF
TCWWLTTISTDLTFSVKSSRGSSDPQGVTCGAATLSAERVRGDNKEYEYSVECQEDSASPAAEESLPIEV
MVDAVHKLKYENYTSSFFIRDIIKPDPPKNLQLKPLKNSRQVEVSWEYPDTWSTPHSYFSLTFAVQVQGK
SKREKKDRVFTDKTSATVICRKNASISVRAQDRYYSSSTNSETNASVPC

What is claimed is:

1. A detection method, comprising:
   (a) providing a sample from a subject that has been administered a first biologic, wherein the sample comprises the first biologic;
   (b) contacting the sample with a polypeptide, wherein the polypeptide is unlabeled, isolated, and soluble;
   (c) contacting the polypeptide in vitro with a second biologic;
   (d) indirectly detecting binding of the polypeptide to the first biologic in the sample by measuring a form of the second biologic in (c), wherein the binding of the polypeptide to the second biologic in the sample that is detected determines a presence or an amount of the first biologic in the sample; and
   (e) detecting a presence or an amount of an autoantibody to the first biologic in the sample.

2. The method of claim 1, wherein the second biologic used to contact the polypeptide in vitro comprises a label.

3. The method of claim 2, wherein the label comprises a fluorophore.

4. The method of claim 1, further comprising comparing the form of the second biologic used to contact the polypeptide in vitro to a known amount of the second biologic.

5. The method of claim 1, wherein the sample is serum.

6. The method of claim 1, wherein the polypeptide comprises an antigen, wherein the antigen comprises a soluble fragment of a cell surface molecule.

7. The method of claim 1, wherein the polypeptide comprises an antigen, wherein the antigen comprises:
   (i) an α4 integrin polypeptide;
   (ii) a β7 integrin polypeptide; or
   (iii) an α4β7 polypeptide, wherein the α4β7 polypeptide comprises the α4 integrin polypeptide and the β7 integrin polypeptide.

8. The method of claim 7, wherein the α4 integrin polypeptide comprises an amino acid sequence having at least 80% identity to SEQ ID NO:1 or SEQ ID NO:3, and the β7 integrin polypeptide comprises an amino acid sequence having at least 80% identity to SEQ ID NO: 2 or SEQ ID NO: 4.

9. The method of claim 7, wherein the α4 integrin polypeptide comprises an ACID peptide.

10. The method of claim 7, wherein the β7 integrin polypeptide comprises a BASE peptide.

11. The method of claim 7, wherein the α4 integrin polypeptide or the β7 integrin polypeptide comprises a linker.

12. The method of claim 7, wherein the α4 integrin polypeptide or the β7 integrin polypeptide comprises an affinity tag.

13. The method of claim 7, wherein the α4 integrin polypeptide or the β7 integrin polypeptide comprises a protease cleavage site.

14. The method of claim 7, wherein the first biologic and the second biologic are vedolizumab.

15. The method of claim 1, wherein the polypeptide comprises an antigen, wherein the antigen comprises a p40 subunit of IL-12 or IL-23.

16. The method of claim 15, wherein the p40 subunit comprises an amino acid sequence having at least 80% identity to SEQ ID NO: 6, 7, 11, 12, or 13.

17. The method of claim 15, wherein the antigen further comprises an affinity tag.

18. The method of claim 15, wherein the first biologic and the second biologic are ustekinumab.

19. The method of claim 1, wherein the first biologic and the second biologic are the same type of biologic.

* * * * *